(12) United States Patent
Schwartz

(10) Patent No.: US 11,867,696 B2
(45) Date of Patent: Jan. 9, 2024

(54) ANTIGEN-COUPLED IMMUNOREAGENTS

(71) Applicant: CELL IDX, INC., San Diego, CA (US)

(72) Inventor: David A. Schwartz, Encinitas, CA (US)

(73) Assignee: CELL IDX, INC., San Diego, CA (US)

( * ) Notice: Subject to any disclaimer, the term of this patent is extended or adjusted under 35 U.S.C. 154(b) by 577 days.

(21) Appl. No.: 15/017,626

(22) Filed: Feb. 6, 2016

(65) Prior Publication Data
US 2016/0258956 A1   Sep. 8, 2016

Related U.S. Application Data

(60) Provisional application No. 62/247,415, filed on Oct. 28, 2015, provisional application No. 62/113,141, filed on Feb. 6, 2015.

(51) Int. Cl.
*G01N 33/00* (2006.01)
*G01N 33/535* (2006.01)
(Continued)

(52) U.S. Cl.
CPC ......... *G01N 33/5743* (2013.01); *C07K 16/00* (2013.01); *C07K 16/44* (2013.01);
(Continued)

(58) Field of Classification Search
USPC .................................................. 436/532, 540
See application file for complete search history.

(56) References Cited

U.S. PATENT DOCUMENTS

| | | |
|---|---|---|
| 4,703,004 A | 10/1987 | Hopp et al. |
| 5,206,370 A | 4/1993 | Schwartz et al. |

(Continued)

FOREIGN PATENT DOCUMENTS

| | | |
|---|---|---|
| WO | WO 1991/018020 A1 | 11/1991 |
| WO | WO 1997/044469 A2 | 11/1997 |

(Continued)

OTHER PUBLICATIONS

US 9,005,993 B2, 04/2015, Sheehan et al. (withdrawn)
(Continued)

*Primary Examiner* — Ellen J Marcsisin
(74) *Attorney, Agent, or Firm* — Frost Brown Todd LLP

(57) ABSTRACT

The present disclosure provides high-performance immunoreagents for use in a variety of immunologic assays and other related techniques. The immunoreagents comprise a primary antibody and a bridging antigen, wherein the bridging antigen is recognized by a detectable secondary antibody with high affinity. Also provided are compositions comprising panels of immunoreagents specific for multiple different target antigens and compositions comprising pairs of primary immunoreagents and their complementary detectable secondary antibodies. The paired primary immunoreagents and secondary antibodies are useful in a variety of immunologic assays, particularly in highly multiplexed assays, where the structure of the bridging antigen is varied in tandem with variation in the detectable secondary antibody, such that a multiplicity of immunoreagents are provided that are capable of simultaneously detecting a multiplicity of target antigens in a single assay. Also provided are kits comprising the immunoreagents, methods of immunologic assay using the immunoreagents of the disclosure, and methods of preparation of the immunoreagents.

28 Claims, 29 Drawing Sheets
(22 of 29 Drawing Sheet(s) Filed in Color)
Specification includes a Sequence Listing.

(51) Int. Cl.
*G01N 33/574* (2006.01)
*G01N 33/533* (2006.01)
*C07K 16/44* (2006.01)
*C07K 16/00* (2006.01)
*G01N 33/543* (2006.01)

(52) U.S. Cl.
CPC ......... *G01N 33/533* (2013.01); *G01N 33/535* (2013.01); *G01N 33/54306* (2013.01); *G01N 33/574* (2013.01); *G01N 2474/20* (2021.08); *G01N 2800/60* (2013.01)

(56) References Cited

U.S. PATENT DOCUMENTS

| | | | |
|---|---|---|---|
| 5,420,285 A | | 5/1995 | Schwartz et al. |
| 5,747,036 A * | | 5/1998 | Brenner ............ C07K 16/2809 424/144.1 |
| 5,753,450 A | | 5/1998 | Baylink |
| 5,753,520 A | | 5/1998 | Schwartz et al. |
| 6,268,222 B1 | | 7/2001 | Chandler et al. |
| 6,403,309 B1 | | 6/2002 | Iris et al. |
| 6,686,461 B1 | | 2/2004 | Schwartz et al. |
| 6,709,596 B1 | | 3/2004 | Reinhold |
| 6,800,728 B2 | | 10/2004 | Schwartz |
| 7,102,024 B1 | | 9/2006 | Schwartz et al. |
| 7,173,125 B2 | | 2/2007 | Schwartz et al. |
| 7,704,962 B1 | | 4/2010 | Tari et al. |
| 7,999,098 B2 | | 8/2011 | Schwartz et al. |
| 8,541,555 B2 | | 9/2013 | Schwartz et al. |
| 8,700,335 B2 | | 4/2014 | Von Hoff et al. |
| 8,768,629 B2 | | 7/2014 | Von Hoff et al. |
| 8,831,890 B2 | | 9/2014 | Von Hoff et al. |
| 8,880,350 B2 | | 11/2014 | Von Hoff et al. |
| 8,914,239 B2 | | 12/2014 | Von Hoff et al. |
| 9,086,407 B2 | | 4/2015 | Sheehan et al. |
| 9,053,224 B2 | | 6/2015 | Von Hoff et al. |
| 9,058,418 B2 | | 6/2015 | Von Hoff et al. |
| 9,064,045 B2 | | 6/2015 | Von Hoff et al. |
| 9,092,392 B2 | | 7/2015 | Von Hoff et al. |
| 9,261,500 B2 | | 2/2016 | Sheehan et al. |
| 9,476,874 B2 | | 10/2016 | Sheehan et al. |
| 9,663,818 B2 | | 5/2017 | Flor et al. |
| 9,778,252 B2 | | 10/2017 | Sheehan et al. |
| 2002/0081617 A1 | | 6/2002 | Buranda et al. |
| 2002/0115113 A1 | | 8/2002 | Lawman et al. |
| 2002/0193572 A1* | | 12/2002 | Leung ..................... B82Y 5/00 530/387.3 |
| 2003/0143636 A1* | | 7/2003 | Simonson ............ G01N 33/558 435/7.9 |
| 2003/0152962 A1 | | 8/2003 | Price |
| 2003/0161826 A1 | | 8/2003 | Arnason et al. |
| 2003/0175828 A1 | | 9/2003 | Azar |
| 2004/0048395 A1 | | 3/2004 | Lee et al. |
| 2004/0142400 A1* | | 7/2004 | Xia .................... C07K 16/2869 435/7.92 |
| 2005/0208589 A1 | | 9/2005 | Stupp et al. |
| 2005/0239142 A1* | | 10/2005 | Lowery ................ G01N 33/542 435/7.1 |
| 2006/0194222 A1 | | 8/2006 | Sorge et al. |
| 2006/0263836 A1 | | 11/2006 | Connelly et al. |
| 2007/0037967 A1 | | 2/2007 | Offord et al. |
| 2007/0087404 A1* | | 4/2007 | Stahl ..................... C07D 205/08 435/68.1 |
| 2007/0148718 A1 | | 6/2007 | Medghalchi et al. |
| 2007/0154958 A1 | | 7/2007 | Hamann et al. |
| 2008/0214408 A1 | | 9/2008 | Chatterjee et al. |
| 2008/0306001 A1* | | 12/2008 | Liik ..................... C07K 14/475 514/1.1 |
| 2009/0035216 A1* | | 2/2009 | Svenson ................ G01N 33/564 424/9.1 |
| 2009/0041717 A1 | | 2/2009 | MacDonald et al. |
| 2010/0003239 A1* | | 1/2010 | Scales ................ G01N 33/57496 424/130.1 |
| 2010/0104589 A1 | | 4/2010 | Govindan et al. |
| 2010/0159446 A1 | | 6/2010 | Haff et al. |
| 2010/0285490 A1* | | 11/2010 | Dees ................ G01N 33/54373 435/7.1 |
| 2011/0052525 A1 | | 3/2011 | Grunewald et al. |
| 2011/0111406 A1 | | 5/2011 | Igawa et al. |
| 2011/0159605 A1 | | 6/2011 | Whitten et al. |
| 2011/0172115 A1 | | 7/2011 | Thompson |
| 2012/0121613 A1 | | 5/2012 | Tang et al. |
| 2012/0258881 A1† | | 10/2012 | Schwartz |
| 2013/0034853 A1 | | 2/2013 | Kelly et al. |
| 2013/0115593 A1 | | 5/2013 | Kelly et al. |
| 2013/0115630 A1 | | 5/2013 | Shore et al. |
| 2013/0123121 A1 | | 5/2013 | Schwartz et al. |
| 2013/0164310 A1* | | 6/2013 | Annathur .................. A61P 3/04 424/178.1 |
| 2013/0184439 A1 | | 7/2013 | Spitali et al. |
| 2013/0195909 A1 | | 8/2013 | Fischer et al. |
| 2013/0237930 A1 | | 9/2013 | Mulvihill et al. |
| 2013/0260379 A1 | | 10/2013 | Alexander et al. |
| 2013/0331297 A1 | | 12/2013 | Fan |
| 2013/0344508 A1 | | 12/2013 | Schwartz et al. |
| 2014/0065634 A1 | | 3/2014 | Walker et al. |
| 2014/0127719 A1 | | 5/2014 | Sheehan et al. |
| 2014/0323336 A1 | | 10/2014 | Kosmeder, II et al. |
| 2015/0182596 A1 | | 7/2015 | Lee et al. |
| 2015/0293073 A1 | | 10/2015 | Murphy et al. |
| 2016/0002701 A1 | | 1/2016 | Farrell et al. |
| 2016/0095938 A1 | | 4/2016 | Fishkin et al. |
| 2016/0258956 A1 | | 9/2016 | Schwartz |
| 2017/0356902 A1 | | 12/2017 | Ukekawa |
| 2018/0003718 A1† | | 1/2018 | Fogelstrand |
| 2019/0112356 A1 | | 4/2019 | Schwartz et al. |
| 2019/0233876 A1 | | 8/2019 | Schwartz |
| 2019/0265235 A1 | | 8/2019 | Schwartz et al. |
| 2021/0032285 A1 | | 2/2021 | Schwartz |
| 2021/0132067 A1 | | 5/2021 | Schwartz |

FOREIGN PATENT DOCUMENTS

| | | | | |
|---|---|---|---|---|
| WO | WO 1999/004042 A1 | 1/1999 | | |
| WO | WO 2005/083802 A1 | 9/2005 | | |
| WO | 2012071428 A2 | 5/2012 | | |
| WO | 2012129610 A1 | 10/2012 | | |
| WO | 2012129611 A1 | 10/2012 | | |
| WO | WO 2013/177046 A1 | 11/2013 | | |
| WO | 2013188756 A1 | 12/2013 | | |
| WO | WO-2014006123 A1 * | 1/2014 | ......... A61K 47/6835 | |
| WO | WO 2014/071531 A1 | 5/2014 | | |
| WO | WO 2014/139979 A1 | 9/2014 | | |
| WO | WO 2015/086549 A1 | 6/2015 | | |
| WO | 2015116868 A2 | 8/2015 | | |
| WO | WO 2015/184144 A1 | 12/2015 | | |
| WO | WO 2016/073833 A1 | 5/2016 | | |

OTHER PUBLICATIONS

Stubenrauch et al., Journal of Pharmaceutical and Biomedical Analysis, 72, (2013), p. 208-215 (Year: 2013).*
MDDI Online, Monoclonal antibodies, (2013) web: https://www.mddionline.com/news/rabbit-monoclonal-antibody-new-diagnostics-technology [Accessed Sep. 8, 2021] (16 pages) (Year: 2013).*
Adams et al. (2015) Nature Rev. Drug Discov. 14:603-22.
Baskin et al. (2007) Proc. Natl Acad. Sci. U.S.A. 104:16793-97.
Coons et al. (1941) Proc Soc Exp Biol. 47:2002.
Dirksen et al. (2006) Angew. Chem. 45:7581-7584 (DOI: 10.1002/anie.200602877).
Evans (2007) Aus. J. Chem. 60:384.
Flor et al. (2013) Chembiochem. 15:267-75.
Frisch et al. (2011) Methods Mol. Biol. 717:233-244 (DOI: 10.1007/978-1-61779-024-9_13).
Serdes et al. (2013) PNAS 110:11982-7 (DOI: 10.1073/pnas.1300136110).
Härtig and Fritschy (2009) Encyclopedia of Life Sciences (ELS), John Wiley & Sons (DOI: 10.1002/9780470015902.a0002626.pub2).
Hollman-Hewgley et al. (2014) Am. J. Path. Surg. 38:1193-1202.

(56) References Cited

OTHER PUBLICATIONS

Kaneko et al. (1991) Bioconj. Chem. 2:133-41.
Karver et al. (2011) Bioconjugate Chem. 22:2263.
Kolb et al. (2001) Angew. Chem. Int. Ed. Engl. 40:2004.
Lamm et al. (1972) Proc. Nat'l Acad. Sci. USA 69:3732-36.
Leriche et al. (2012) Bioorg. Med. Chem. 20:571-582 (DOI:10.1016/j.bmc.2011.07.048).
Ma et al. (2015) Chem. Soc. Rev. (DOI: 10.1039/C4CS00357H).
Mahoney et al. (2015) Nature Rev. Drug Discov. 14:561-84.
Moriya et al. (2006) Med. Mol. Morphol. 39:8-13.
Ortiz de Montellano et al. (1988) Biochemistry 27:5470-5476 (DOI: 10.1021/bi00415a013).
Payne et al. (2008) Histopathology 52:82-90.
Pirici et al. (2009) J. Histochem. Cytochem. 57:567-575 (DOI: 10.1369/jhc.2009.953240).
Sharma et al. (2015) Science 348:56-61.
Shin et al. (2015) Curr. Opin. Immunol. 33:23-35.
Stack et al. (2014) Methods 70:46-58 (DOI: 10.1016/j.ymeth.2014.08.016).
Stöckmann et al. (2011) Org. Biomol. Chem. 9:7303.
Tanenbaum et al. (2014) Cell 159:635646.
Tumeh et al. (2014) Nature 515: 568571 (DOI:10.1038/nature13954).
Wang et al. (2011) Curr. Med. Chem. 18:41754184.
Wang et al. (2013) Proc. Nat'l Acad. Sci. USA 110:4261-66.
Wu et al. (2005) Nature Biotechnol. 23:1137-46.
Yeh et al. (2008) Arch. Pathol. Lab. Med. 132:349-57.
Wallace et al. (1979) J. Immunol. Meth. 25:283-289.
Behringer et al. (1991) J. Histochem. Cytochem. 39:761-770.
Patten et al. (1996) Science 271:1086-1091.
Heinrich et al. (2010) Journal Of Immunological Methods 352:13-22.
Estep et al. (2013) mAbs 5:270-278.
Fujii et al (2014) Protein Expression And Purification 95:240-247.
Cho et al., Relationship between the expressions of PD-L 1 and tumor-infiltrating lymphocytes in oral squamous cell carcinoma, Oral Oncology, 47, (2011 ), p. 1148-1153 (Year: 2011).
Buchwalow et al., A multicolor fluorescence immunostaining technique for simultaneous antigen targeting, Acta Histochemica, 107, (2005), p. 143-148 (Year: 2005).
Stubenrauch et al., (Characterization of murine anti-human Fab antibodies for use in an immunoassay for generic quantification of X human Fab fragments in non-human serum samples including cynomolgus monkey samples, Journal of Pharmaceutical and Biomedical Analysis, 72, (2013), p. 208-215 (Year: 2013).
Einhauer and Jungbauer (2001) J. Chromatog. 921:25-30.
Einhauer and Jungbauer (2001) J. Biochem. Biohys. Methods 49:455-465.
Härtig et al. (1995) Histochem. Cell. Biol. 104:467-472.
Flow Cytometry/Cell Sorting & Confocal Microscopy Core Facility, EOHSI, 848, (2007), (2 pages) (Online accessed at: https://flowcyt.rutgers.edu/wp-content/uploads/2017/10/Intracellular-Innnnunofluorescence-Staining-Protocol.pdf on Jul. 28, 2021) (Year: 2007).
Khan, Saleem A., and T. M. Jacob. "Antibodies specific to two deoxyribotrinucleotide sequences." *Nucleic Acids Research* 4.9 (1977): 3007-3016.
Minamihata, Kosuke, Masahiro Goto, and Noriho Kamiya. "Site-specific protein cross-linking by peroxidase-catalyzed activation of a tyrosine-containing peptide tag." *Bioconjugate chemistry* 22.1 (2011): 74-81.
Nakane, Paul K., and Akira Kawaoi. "Peroxidase-labeled antibody a new method of conjugation." *Journal of Histochemistry & Cytochemistry* 22.12 (1974): 1084-1091.
Spänkuch, Birgit, et al. "Downregulation of Plk1 expression by receptor-mediated uptake of antisense oligonucleotide-loaded nanoparticles." *Neoplasia* 10.3 (2008): 223-234.
Villain, Matteo, Jean Vizzavona, and Keith Rose. "Covalent capture: a new tool for the purification of synthetic and recombinant polypeptides." *Chemistry & biology* 8.7 (2001): 673-679.
Wilson, M. Barbara, and Paul K. Nakane. "The covalent coupling of proteins to periodate-oxidized sephadex: a new approach to immunoadsorbent preparation." *Journal of Immunological Methods* 12.1-2 (1976): 171-181.

\* cited by examiner
† cited by third party

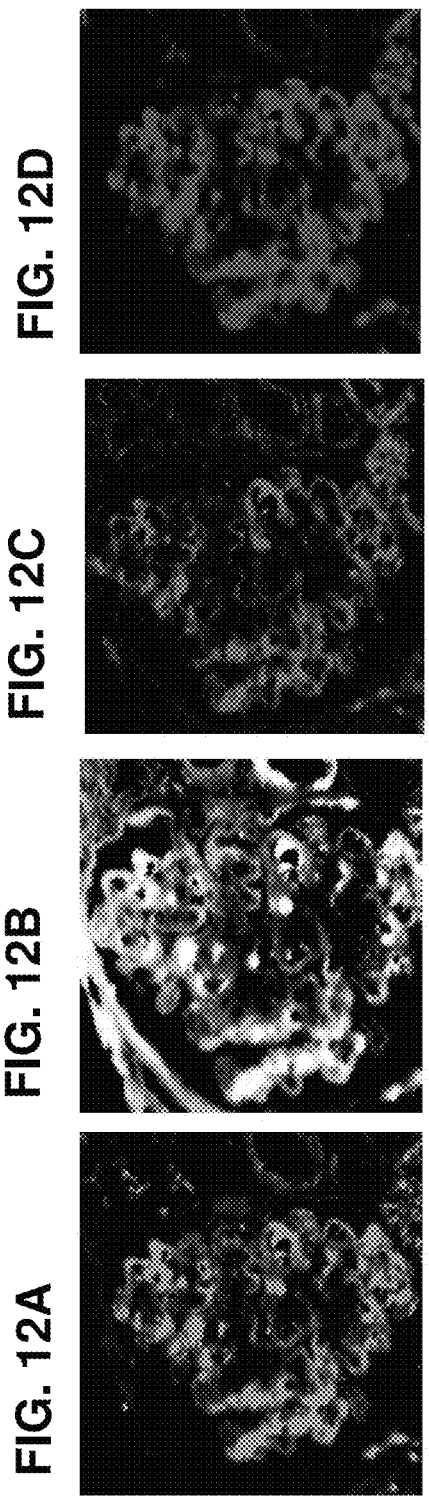

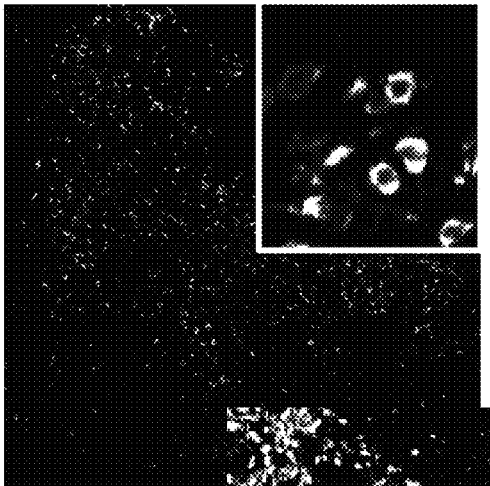
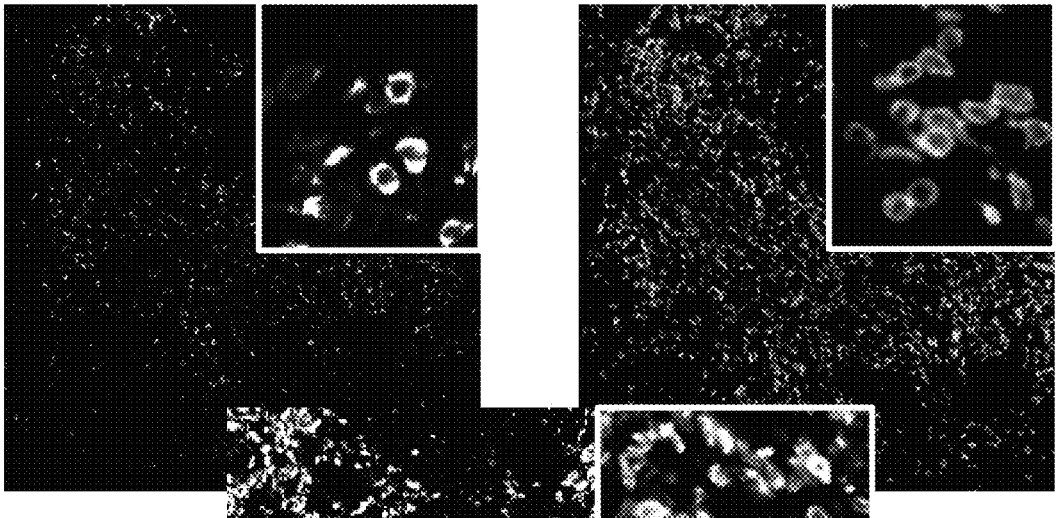
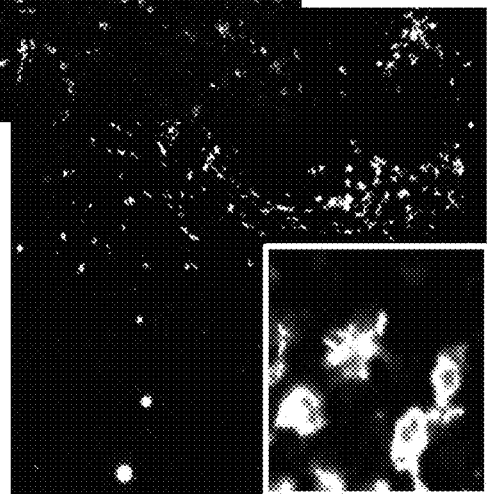
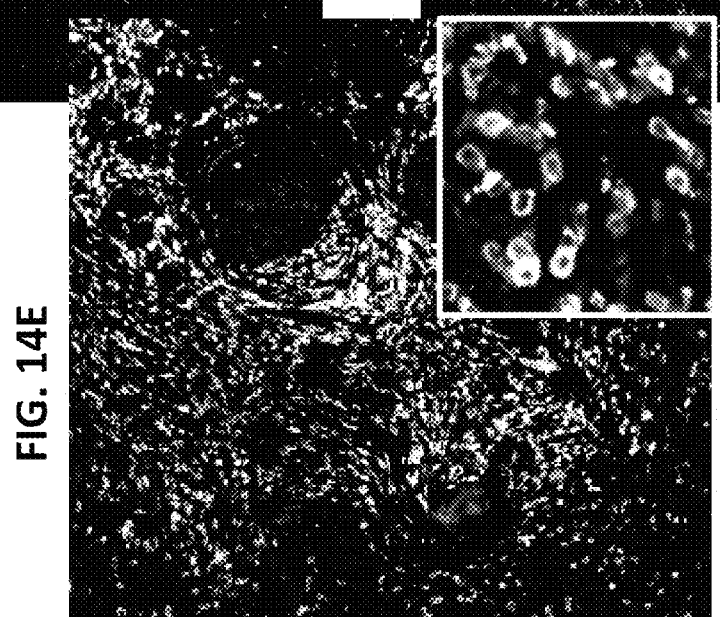
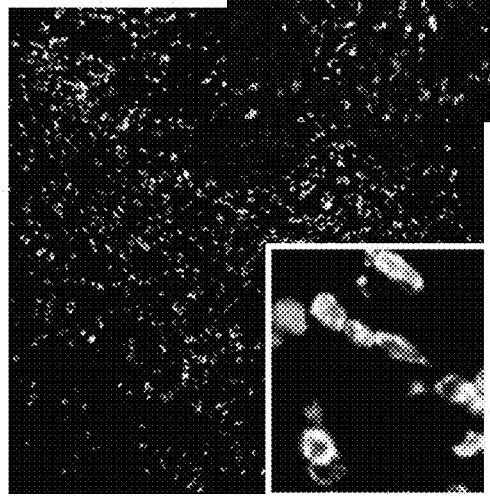

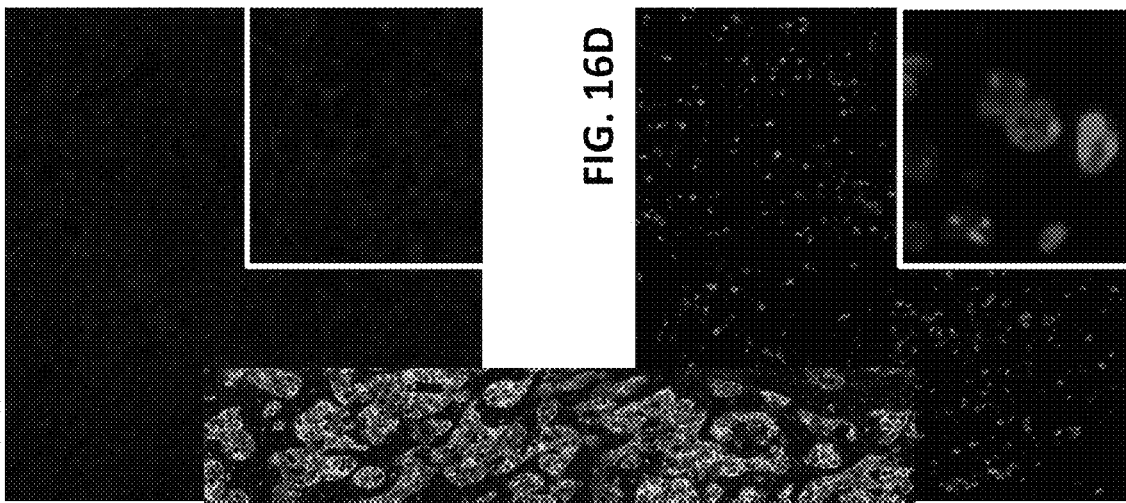
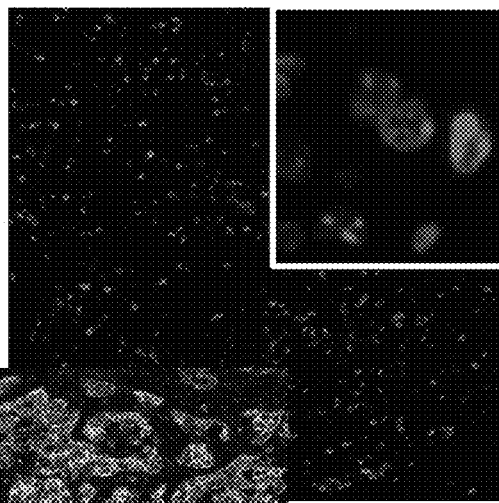
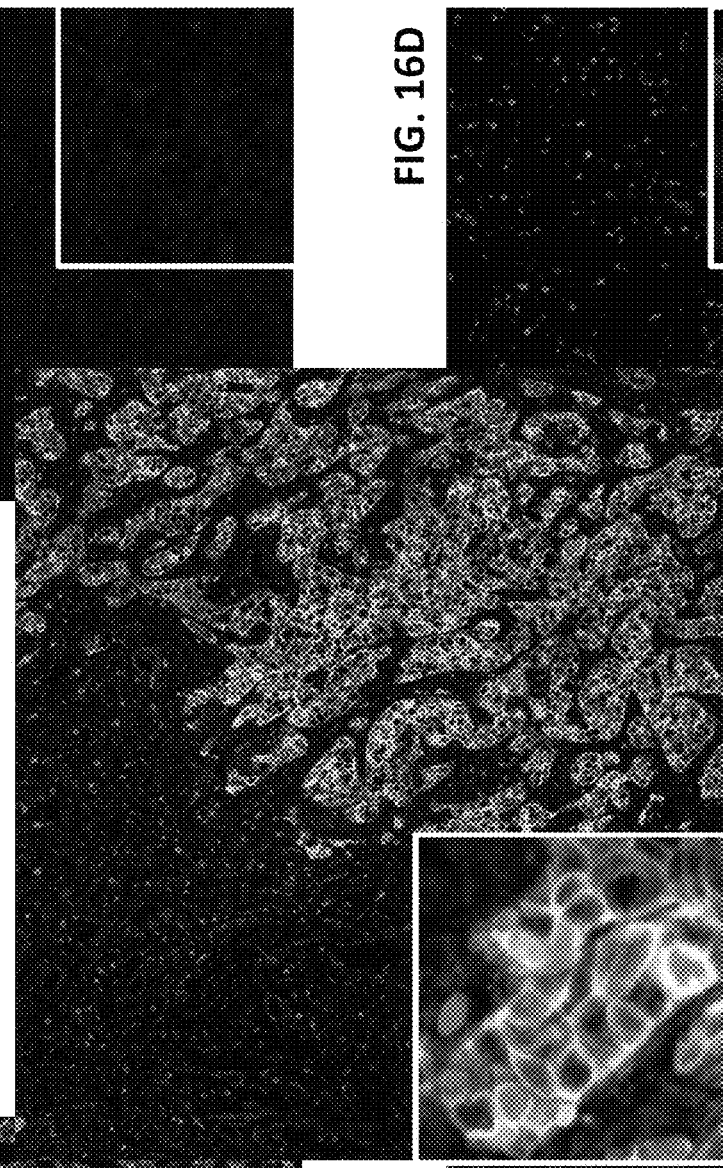
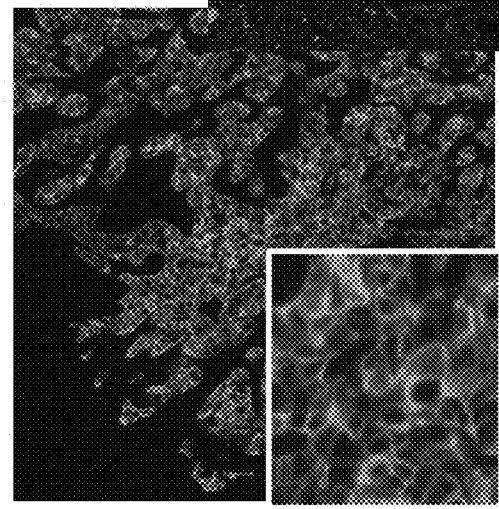
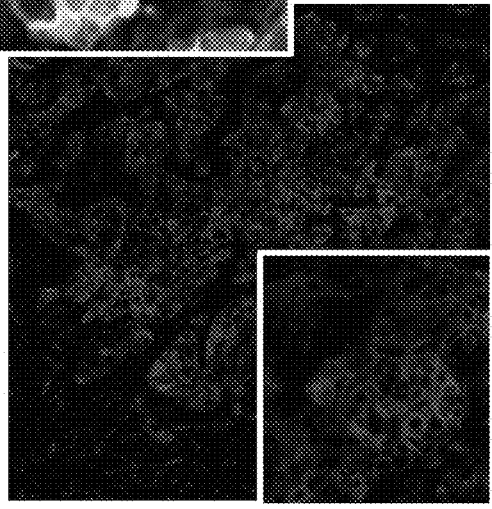

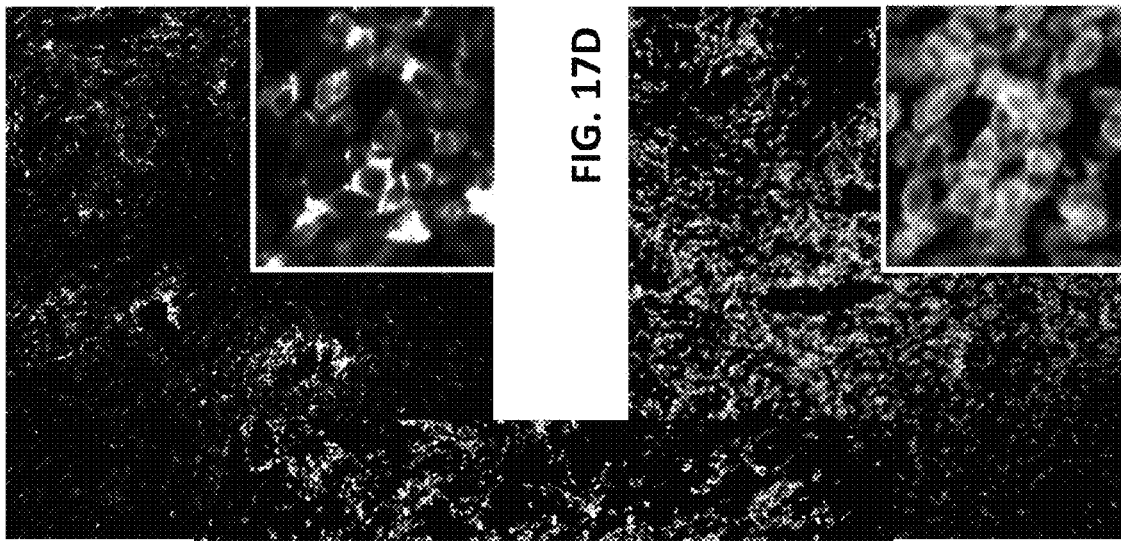
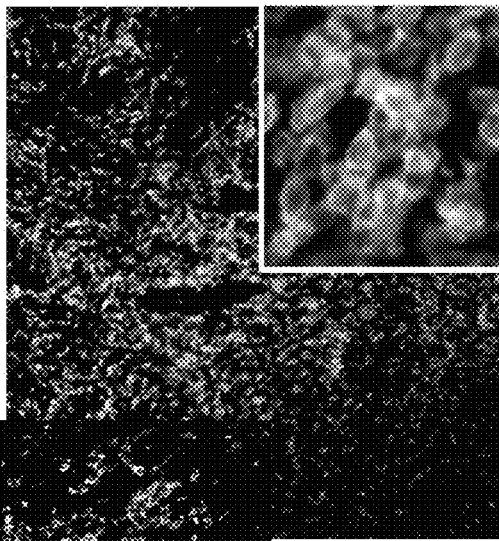
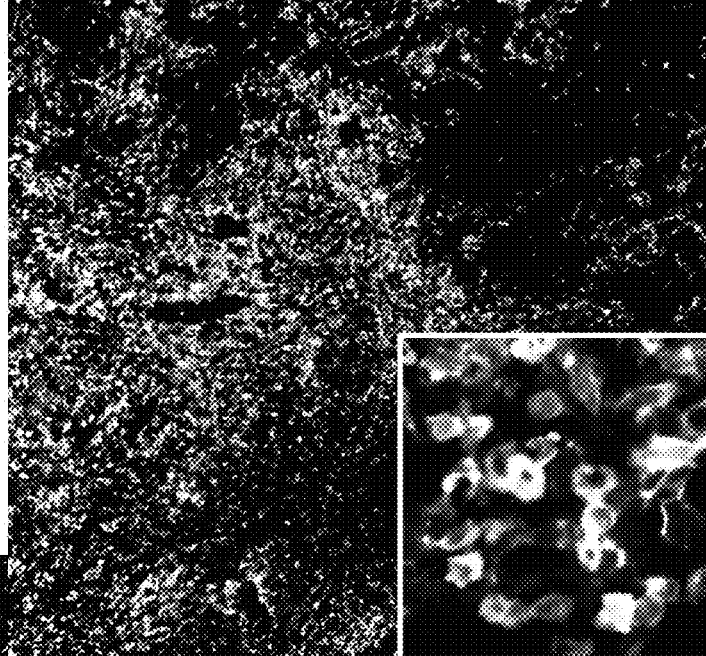
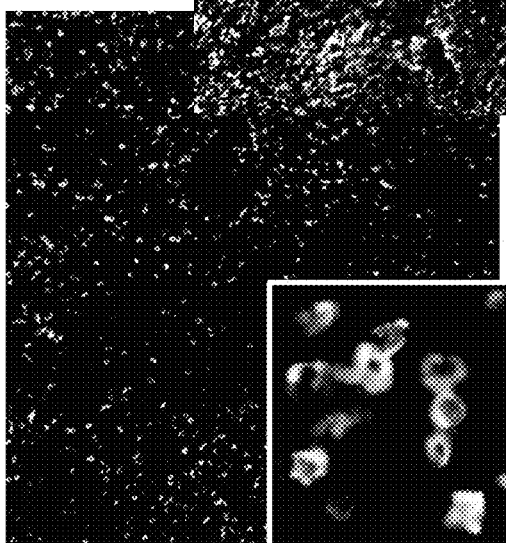
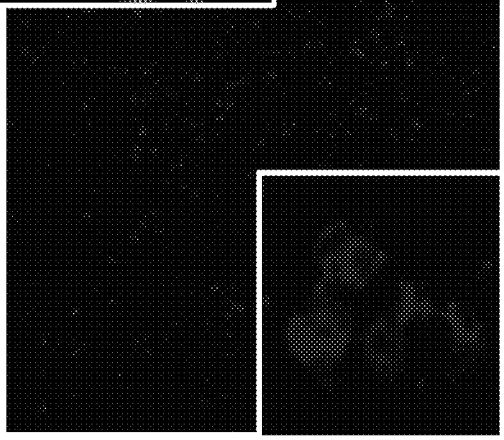
FIG. 17A
FIG. 17B
FIG. 17C
FIG. 17D
FIG. 17E

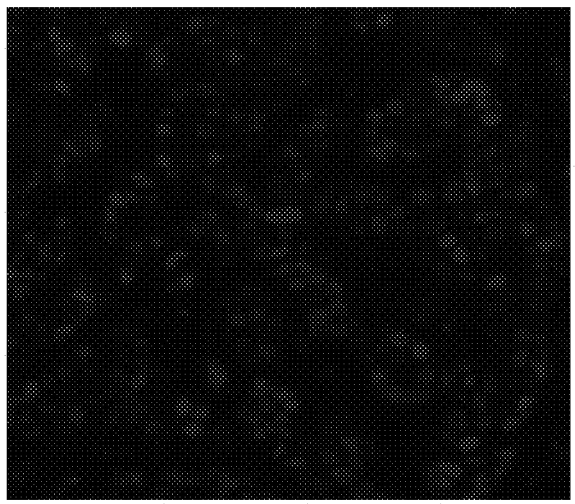
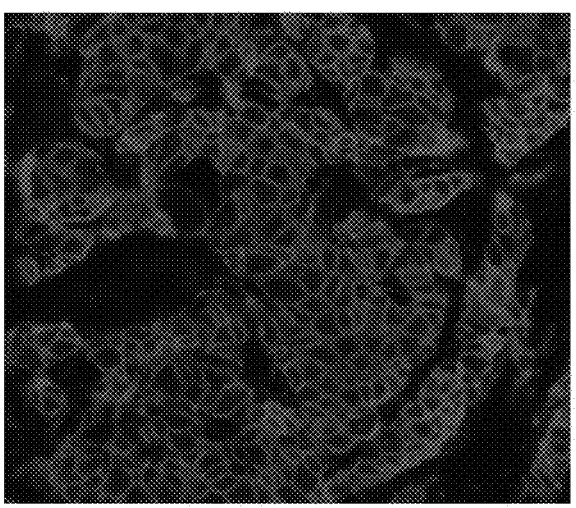
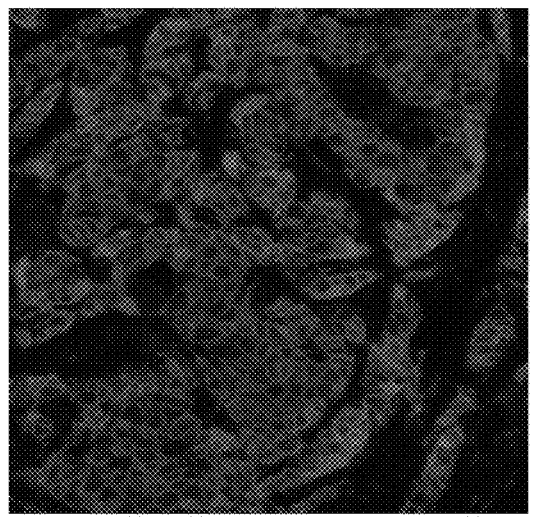
FIG. 24A
FIG. 24B
FIG. 24C

STRIP

ANTIGEN-COUPLED IMMUNOREAGENTS

CROSS-REFERENCE TO RELATED APPLICATIONS

This application claims the benefit of U.S. Provisional Application No. 62/113,141, filed on Feb. 6, 2015, and U.S. Provisional Application No. 62/247,415, filed on Oct. 28, 2015, the disclosures of which are incorporated herein by reference in their entireties.

STATEMENT REGARDING FEDERALLY-SPONSORED RESEARCH

This invention was made with government support under HHSN261201200089C awarded by the National Institutes of Health. The government has certain rights in the invention.

SEQUENCE LISTING

This application includes a Sequence Listing, as set forth in an ASCII-compliant text file named "2068-00-002U01 ST25", created on May 24, 2016, and containing 3,279 bytes, which is incorporated by reference herein.

BACKGROUND OF THE INVENTION

The use of immunologic assays, in particular the use of immunohistochemical (IHC) staining, is of critical importance in the analysis of pathological conditions, such as the analysis of abnormal cells, including cancerous tumor cells. In IHC, an immunoglobulin or antibody that recognizes a specific antigen that may be present in a diseased tissue is applied to a thin section of that tissue obtained by biopsy. The binding of the antibody to its cognate antigen is then detected within the tissue section, typically by imaging the distribution of a chromogenic enzymatic product that is produced by an enzyme, such as a peroxidase, that is co-localized with the immunoglobulin. Examining the distribution of enzymatic product in comparison to the distribution of histological stain enables evaluation of the distribution of the antigen in the tissue section. In other immunologic assays, the antibody binding to the antigen may be detected by other means including optical, electrical, or chemical signals. Specific antigens may characterize particular cellular events, for example infection, injury, cell proliferation, inflammation, or drug response. Immunologic assays are also widely used in basic research to understand the distribution and localization of antigens that serve as biomarkers, such as proteins differentially expressed in different parts of a cell or biological tissue, and to identify and quantify those antigens in biochemical assays. Immunologic assays are thus of use, for example, in blots, sandwich assays, immunosorbent assays, immunocytochemical assays, and other related methods. All of these methods could benefit from improved immunochemical reagents.

Current methods of tissue analysis in clinical pathology are essentially restricted to single-antigen determinations performed on a single microscope slide. Importantly, there is a one-to-one correspondence between an antibody and its antigen, allowing ready determination of the antigen by binding or lack of binding of an antibody. Where each antibody is linked to a peroxidase or other enzyme, the presence of an antigen can be determined by the amount and distribution of enzyme product on the respective tissue section as a proxy. However, there is frequently more than one antigen that must be evaluated to complete a particular analysis. For example, in breast cancer, to optimally match a therapy to each patient, a minimum antigenic profile of a biopsy specimen would include evaluation of the presence and abundance of at least three antigens in the malignant cells of the tumor: Her2/neu receptor (HER2), estrogen receptor (ER), and progesterone receptor (PR). Performing the analysis would thus require an assay for each of the three distinct immunoglobulins, each of which is typically a monospecific monoclonal antibody that is capable of detecting only one of the three antigens. To examine the degree of binding of the three different immunoglobulins to the malignant cells using traditional assays, three different IHC tests would thus need to be performed on three different tissue sections derived from the same block of tumor material. In addition, with traditional enzyme-based assays, as are typically now used in routine tissue analysis, each slide must be evaluated by a pathologist using a qualitative scoring system to determine the presence or absence and the level of expression of a given antigen. The results from the three tests must then be combined to determine the profile, which will offer prognostic information and aid in selection of therapy. Improving the efficiency, accuracy, and reliability of such assays is of major importance in the field.

Because of the need for high levels of reproducibility across laboratories, immunohistochemical analysis typically relies on standard methods, such as enzymatic detection, and a few well-studied antigens, as recognized by well-characterized antibodies (Moriya et al. (2006) *Med. Mol. Morphol.* 39:8-13; Payne et al. (2008) *Histopathology* 52:82-90; Yeh and Mies (2008) *Arch. Pathol. Lab. Med.* 132:349-57). Although direct detection of a peroxidase associated with a primary antibody is used in some cases, indirect detection by peroxidase-linked secondary antibodies or through primary antibodies tagged with high-affinity small-molecule/binding protein pairs, such as biotin and avidin, can be used to amplify the signal and thus to improve sensitivity of the assays. In each of these cases, intensity of signal is typically judged subjectively, however, thus limiting the diagnostic and prognostic value of the assays.

About 1.6 million breast biopsies a year are performed in the United States, typically in women who have developed a breast lump. A biopsy entails sampling the tissue of the lump by fine needle aspiration or core needle through the skin or an open procedure. The resulting tissue is then examined to detect the presence of malignant cells. The majority of such biopsies are considered benign based on examination of the tissue using histology techniques. In 2010, histological analysis determined that 260,000 biopsies displayed malignancy. Of these, some 200,000 women had invasive breast cancer, and others were described as ductal carcinoma in situ (DCIS), in which cancer cells have not invaded the surrounding tissue. Advances in early detection and definitive treatment of primary tumors have dramatically improved breast cancer survival statistics. Yet, many tumors escape early detection or, in spite of effective primary therapy, go on to develop distant metastases, the leading cause of breast cancer mortality. Much of the current effort in molecular analysis of breast cancer is directed at identifying new biomarkers and defining the mechanistic determinants of prognosis and prediction. It would be helpful if any such novel disease markers could be readily incorporated into the routine immunohistochemical staining of tissue biopsies.

As mentioned above, because of the limitations of detection using enzyme conjugates, each target antigen is often evaluated on a separate histological section, and internal controls are not readily implemented. As a result, quantitation, evaluation of co-localization, and subcellular resolution are problematic. A well-established alternative to enzyme conjugates for detection in immunohistochemistry makes use of fluorescently-labeled probes. The principal advantage of this approach lies in the potential for multiplexing. In short, either the antibody itself, or more typically, a secondary antibody or other indirect detection reagent, is labeled with a fluorescent group, protein, or other material of known spectroscopic properties. Upon illumination of the sample with light at the excitation wavelength of the fluorescent label, the presence of a fluorescent signal at a specific emission wavelength, and the localization of that signal at sites within a tissue section are observed. The fluorescence signal thus serves the same purpose as the chromogenic enzyme product in providing information regarding the amount and distribution of the antigen.

Covalent modification of immunoglobulins with chemically-reactive fluorescent reagents to form fluorescent antibodies, and the use of the fluorescent antibodies in the detection of antigens is now well-established, having been demonstrated by Coons' modification of specific immunoglobulins with fluorescein isothiocyanate in 1941. Coons et al. (1941) *Proc Soc Exp Biol.* 47:200-2. Simultaneous detection of two antigens by antibodies labeled with distinct fluorescent colors, fluorescein and rhodamine, followed soon thereafter. Modern chemistry has provided a broad range of chemically-reactive fluorophores, with excitation and emission spectra that range from the ultraviolet to infrared. In turn, modern coating methods have produced interference filters that can readily distinguish four or more different fluorophores over the visible light spectrum, with signal-to-noise ratios much greater than 10, by selecting specific excitation and emission bands.

Fluorescence-based immunologic assays are of growing importance in the staining of pathological sections and in cytometry, at least in part because of the ability to distinguish multiple antigens through the use of multiple, differentially-labeled, fluorescent antibodies. In these approaches, the different antibodies are distinguishable, for example, by measuring fluorescence emitted at different wavelengths. Other spectroscopic properties of the different fluorophores may also potentially be used to distinguish the bound antibodies. While it has been recognized that fluorescence-based assays could potentially be used to detect >3 antigens on a single tissue, current methods with fluorescently-labeled primary antibodies do not provide sufficient sensitivity. In particular, only 3-5 fluorophores can be conjugated to a single antibody due to fluorescence quenching or reduced immunoreactivity upon incorporation of >5 fluorophores into the antibody. Furthermore, monoclonal antibodies bind to a single epitope on any target antigen and thus further limit any possible amplification of signal by the binding of multiple antibodies to multiple sites on the antigen.

By contrast, fluorescently-labeled polyclonal secondary antibodies can produce a stronger signal than fluorescently-labeled primary antibodies, because multiple secondary antibodies can bind to distinct epitopes presented on each primary antibody molecule. This approach is typically limited to the detection of only one or two targets, however, as the majority of primary antibodies have been produced in only two species, mouse and rabbit.

One approach to enable multiplexing using antibodies from one species has been the use of hapten-modified antibodies and fluorescently labeled anti-hapten antibodies. However, using conventional reagents, this method yields a signal that is significantly less intense than that generated by a fluorescently-labeled secondary antibody, probably because of the relatively low affinity of commercial antibodies for small-molecule haptens.

To further advance immunohistochemistry there thus remains a need for a technology that is able to produce a panel of reagents that can satisfy some or all of the following criteria: 1) ability to analyze multiple antigens simultaneously within a single tissue sample and within the context of tissue morphology with greater sensitivity and specificity than currently available, 2) ability to analyze the spatial distribution of multiple antigens in relationship to each other, 3) ability to quantify each antigen individually and to determine ratios of one antigen to another with greater sensitivity and specificity, 4) ability to identify objects of interest (cell types) based on their staining patterns, 5) ability to numerically quantify objects of interest and 6) ability to be incorporated in automated staining and image analysis paradigms that will allow complete automation of the analyses of multiple antigens on a single tissue. Further, there remains a need for user-friendly kits enabling rapid, standardized multiple-antigen detection and quantification for diagnostic or research purposes. The present disclosure is directed to addressing these needs, as well as other problems in immunologic assays that are not currently being addressed.

For example, Härtig and Fritschy (2009) Encyclopedia of Life Sciences (ELS), John Wiley & Sons (DOI: 10.1002/9780470015902.a0002626.pub2) disclose the labeling of tissue sections with a primary antibody that was haptenlyated with biotin, with a primary antibody that was haptenlyated with digoxigenin, and with a lectin that was fluoresceinated. The labeled sample was then stained using fluorescently-labeled streptavidin, anti-digoxigenin, and anti-fluorescein. The level of multiplexing possible using these haptens is limited, however, and the low affinity of antibodies available against the haptens further limits the sensitivity of these assays.

Frisch et al. (2011) *Methods Mol. Biol.* 717:233-244 (DOI: 10.1007/978-1-61779-024-9_13) disclose a multicolor immunofluorescence technique using primary antibodies derived from a single host source. As with Härtig and Fritschy, the primary antibodies were haptenlyated with biotin and digoxigenin, and the secondary stain contained fluorescently-labeled streptavidin and anti-digoxigenin. Samples were additionally labeled with a traditional fluorescently-labeled cross-species secondary antibody/primary antibody pair prior to treatment with the haptenlyated primary antibodies to provide triplex staining. Although the technique minimizes cross-reactivity between irrelevant primary and secondary antibodies and allows for limited simultaneous multiplexing, the approach is limited in sensitivity and cannot be easily scaled to greater levels of multiplexing.

Gerdes et al. (2013) *PNAS* 110:11982-7 (DOI: 10.1073/pnas.1300136110) describe the use of the MultiOmyx™ (GE Healthcare) hyperplexing technology to detect 61 protein biomarkers in formalin-fixed, paraffin-embedded (FFPE) cancer tissue. This assay uses pairs of fluorescently-labeled antibodies in each round of staining followed by peroxide bleaching of the dyes before each subsequent round. (See also www.multiomyx.com.) The technology is significantly limited, however by its ability to detect only highly-expressed targets with fluorescently-labeled primary antibodies, and the need to use indirect detection to image low-expressed targets with fluorescently-labeled secondary antibodies. This technique also requires optimization of pairing of antibodies for each round. The method is also extremely labor intensive, as there are 31 rounds of staining, imaging and bleaching. It is further recognized that multiple peroxide incubations could adversely affect the sensitivity of detection of each target in subsequent rounds of staining and imaging.

Hollman-Hewgley et al. (2014) *Am. J. Path. Surg.* 38:1193-1202 similarly describe use of the MultiOmyx™ (GE Healthcare) hyperplexing technology to detect 10 protein biomarkers in FFPE Hodgkin Lymphoma tissue.

Stack et al. (2014) *Methods* 70:46-58 (DOI: 10.1016/j.ymeth.2014 . . . 08.016) describe a different iterative multiplexed approach that requires a separate singleplexed IHC assay for each marker. The initial labeling is followed by a series of steps to image a single biomarker by peroxidase/tyramide detection, followed by antibody stripping using a microwave antigen retrieval step. This procedure is repeated 5-6 times as required by the number of biomarkers being interrogated. The procedure requires two days to complete.

Despite the above attempts, there continues to be a need for the development of improved immunologic assay reagents, methods, and kits that are more sensitive, more specific, and more able to detect multiple antigens in a single assay.

SUMMARY OF THE INVENTION

The present disclosure addresses these and other needs by providing in one aspect an immunoreagent composition that finds utility in a variety of immunologic assays. Specifically, according to this aspect of the invention, the immunoreagent composition comprises:
  a primary antibody coupled to a bridging antigen; and
  a detectable secondary antibody;
  wherein the detectable secondary antibody is specific for the bridging antigen with high affinity.

In some embodiments, the bridging antigen is a peptide or small-molecule hapten.

In some embodiments, the bridging antigen comprises a plurality of antigenic determinants. In specific embodiments, each antigenic determinants in the plurality of antigenic determinants is the same. In other specific embodiments, the plurality of antigenic determinants comprises a linear repeating structure. More specifically, the linear repeating structure is a linear repeating peptide structure.

In other specific embodiments, the plurality of antigenic determinants comprises at least three antigenic determinants or the bridging antigen comprises a branched structure.

In some embodiments, the bridging antigen is a peptide comprising a non-natural residue. Specifically the non-natural residue may be a non-natural stereoisomer or a β-amino acid.

In some embodiments, the primary antibody and the bridging antigen are coupled by a chemical coupling reaction through a conjugation moiety. In specific embodiments, the primary antibody and the bridging antigen are coupled by a high-efficiency conjugation moiety. In some of these embodiments, the high-efficiency conjugation moiety is a Schiff base, such as a hydrazone or an oxime. In some embodiments, the high-efficiency conjugation moiety is formed by a click reaction. In some embodiments, the conjugation moiety comprises a cleavable linker.

In certain embodiments, the primary antibody is specific for a cellular marker. Specifically, the cellular marker may be selected from the group consisting of: 4-1BB, AFP, ALK1, Amyloid A, Amyloid P, Androgen Receptor, Annexin A1, ASMA, BCA225, BCL-1, BCL-2, BCL-6, BerEP4, Beta-Catenin, Beta-HCG, BG-8, BOB-1, CA19-9, CA125, Calcitonin, Caldesmon, Calponin-1, Calretinin, CAM 5.2, CD1a, CD2, CD3, CD4, CD5, CD7, CD8, CD10, CD15, CD19, CD20, CD21, CD22, CD23, CD25, CD30, CD31, CD33, CD34, CD38, CD42b, CD43, CD45 LCA, CD45RO, CD56, CD57, CD61, CD68, CD79a, CD99, CD117, CD138, CD163, CDX2, CEA, Chromogranin A, CMV, c-kit, c-MET, c-MYC, Collagen Type IV, Complement 3c (C3c), COX-2, CXCR5, CK1, CK5, CK6, CK7, CK8, CK14, CK18, CK17, CK19, CK20, CK903, CK AE1, CK AE1/AE3, D2-40, Desmin, DOG-1, E-Cadherin, EGFR, EMA, ER, ERCC1, Factor VIII-RA, Factor XIIIa, Fascin, FoxP1, FoxP3, Galectin-3, GATA-3, GCDFP-15, GCET1, GFAP, Glycophorin A, Glypican 3, Granzyme B, HBME-1, *Helicobacter Pylori*, Hemoglobin A, Hep Par 1, HER2, HHV-8, HMB-45, HSV 1/11, ICOS, IFNgamma, IgA, IgD, IgG, IgM, IL17, IL4, Inhibin, iNOS, Kappa Ig Light Chain, Ki67, LAG-3, Lambda Ig Light Chain, Lysozyme, Mammaglobin A, MART-1/Melan A, Mast Cell Tryptase, MLH1, MOC-31, MPO, MSA, MSH2, MSH6, MUC1, MUC2, MUM1, MyoD1, Myogenin, Myoglobin, Napsin A, Nestin, NSE, Oct-2, OX40, OX40L, p16, p21, p27, p40, p53, p63, p504s, PAX-5, PAX-8, PD-1, PD-L1, PHH3, PIN-4, PLAP, PMS2, *Pneumocystis jiroveci (carinii)*, PR, PSA, PSAP, RCC, S-100, SMA, SMM, Smoothelin, SOX10, SOX11, Surfactant Apoprotein A, Synaptophysin, TAG 72, TdT, Thrombomodulin, Thyroglobulin, TIA-1, TIM3, TRAcP, TTF-1, Tyrosinase, Uroplakin, VEGFR-2, Villin, Vimentin, and WT-1. In other embodiments, the primary antibody is specific for an immunoglobulin from a different species.

In embodiments, the detectable secondary antibody comprises a detectable label. In some embodiments, the detectable label is a fluorophore, an enzyme, an upconverting nanoparticle, a quantum dot, or a detectable hapten. In specific embodiments, the detectable label is a fluorophore. In other specific embodiments, the enzyme is a peroxidase, such as a horseradish peroxidase or a soybean peroxidase, is an alkaline phosphatase, or is a glucose oxidase.

According to some embodiments, the detectable secondary antibody is specific for the bridging antigen with a dissociation constant of at most 100 nM, at most 30 nM, at most 10 nM, at most 3 nM, at most 1 nM, at most 0.3 nM, at most 0.1 nM, at most 0.03 nM, at most 0.01 nM, at most 0.003 nM, or even lower.

Some composition embodiments comprise a plurality of bridging antigen-coupled primary antibodies and a plurality of detectable secondary antibodies, including compositions comprising three, five, ten, or even more reagent pairs.

In another aspect, the disclosure provides immunoreagents comprising:
  a primary antibody coupled to a bridging antigen.

In specific embodiments, the immunoreagents include one or more of the features of the immunoreagents of the above-described immunoreagent compositions.

According to another aspect, the disclosure provides multiplexed immunoreagent compositions comprising a plurality of any of the above-described immunoreagents. In specific embodiments, the compositions comprise at least three, at least five, at least ten, or even more of the immunoreagents.

In another aspect, the disclosure provides methods for immunologic assay comprising:
  providing a first sample comprising a first target antigen;
  reacting the first target antigen with a first immunoreagent, wherein the first immunoreagent is any of the above immunoreagents specific for the first target antigen;
  reacting the first immunoreagent with a first detectable secondary antibody, wherein the first detectable secondary antibody is specific for the bridging antigen of the first immunoreagent with high affinity; and
  detecting the first detectable secondary antibody that is associated with the bridging antigen of the first immunoreagent.

In embodiments, the first target antigen is a cellular marker, for example ER, HER2, PR, Ki67, EGFR, CK1, CK5, CK6, CK7, CK14, CK17, cytokeratin AE1/AE3, nestin, vimentin, ASMA, Ber-EP4, p16, p40, p53, p63, c-kit, a CD marker, or any of the above-described markers. In other embodiments, the first target antigen is an immunoglobulin from a different species.

In specific embodiments, the first detectable secondary antibody comprises a detectable label. More specifically, the detectable label may be a fluorophore, an enzyme, an upconverting nanoparticle, a quantum dot, or a detectable hapten. In some embodiments, the detectable label is a fluorophore, and in some embodiments, the enzyme is a peroxidase, an alkaline phosphatase, or a glucose oxidase. In specific embodiments, the peroxidase is a horseradish peroxidase or a soybean peroxidase.

In some embodiments, the first target antigen is within a tissue section. In these embodiments, the detecting step may be a fluorescence detection step or an enzymatic detection step.

In some embodiments, the first target antigen may be in or on a cell. In these embodiments, the first target antigen may be on the surface of the cell, in the cytoplasm of the cell, or in the nucleus of the cell.

In some embodiments, the detecting step is a fluorescence detection step, and in specific embodiments, the method may further comprise the step of sorting cells that have bound the first detectable secondary antibody.

In some embodiments, the methods further comprise
  reacting a second target antigen on the first sample with a second immunoreagent, wherein the second immunoreagent is any of the above immunoreagents specific for the second antigen;
  reacting the second immunoreagent with a second detectable secondary antibody, wherein the second detectable secondary antibody is specific for the bridging antigen of the second immunoreagent with high affinity; and
  detecting the second detectable secondary antibody that is associated with the bridging antigen of the second immunoreagent.

More specific method embodiments further comprise detecting at least three target antigens in the sample, at least five target antigens in the sample, or even at least ten target antigens in the sample.

Some method embodiments further comprise the steps of:
  reacting a second target antigen on a second sample with a second immunoreagent, wherein the second immunoreagent is any of the above immunoreagents specific for the second target antigen;
  reacting the second immunoreagent with a second detectable secondary antibody, wherein the second detectable secondary antibody is specific for the bridging antigen of the second immunoreagent with high affinity; and
  detecting the second detectable secondary antibody that is associated with the bridging antigen of the second immunoreagent; wherein the first sample and the second sample are serial sections of a tissue sample.

Other method embodiments comprise the steps of:
  providing a sample comprising a first target antigen;
  reacting the first target antigen with a first immunoreagent, wherein the first immunoreagent is any of the above immunoreagents specific for the first target antigen;
  reacting the first immunoreagent with a first reactive secondary antibody, wherein the first reactive secondary antibody binds to the bridging antigen of the first immunoreagent with high affinity; and
  reacting the first reactive secondary antibody with a first detectable reagent, wherein the first detectable reagent is bound to the sample in proximity to the first target antigen.

In some embodiments, these methods further comprise the step of:
  dissociating the first reactive secondary antibody from the sample.

In some embodiments, these methods still further comprise the steps of:
  reacting a second target antigen on the sample with a second immunoreagent, wherein the second immunoreagent is any of the of the above immunoreagents specific for the second target antigen;
  reacting the second immunoreagent with a second reactive secondary antibody, wherein the second reactive secondary antibody binds to the bridging antigen of the second immunoreagent with high affinity; and
  reacting the second reactive secondary antibody with a second detectable reagent, wherein the second detectable reagent is bound to the sample in proximity to the second target antigen.

In some embodiments, these methods comprised the step of:
  detecting the first detectable reagent and the second detectable reagent on the sample.

Other methods for immunologic assay comprise
  providing a sample comprising a first target antigen;
  reacting the first target antigen with a first primary antibody, wherein the first primary antibody is specific for the first target antigen;
  reacting the first primary antibody with a first immunoreagent, wherein the first immunoreagent is any of the above immunoreagents specific for the first primary antibody;
  reacting the first immunoreagent with a first detectable secondary antibody, wherein the first detectable secondary antibody is specific for the bridging antigen of the first immunoreagent with high affinity; and
  detecting the first detectable secondary antibody that is associated with the bridging antigen of the first immunoreagent.

According to another aspect, the disclosure provides kits for immunologic assay. In embodiments, the kits comprise any of the above immunoreagents, a detectable secondary antibody specific for the bridging antigen of the immunoreagent with high affinity, and instructions for using the kit. In specific embodiments, the kits comprise at least three, at least five, or even at least ten of any of the above immunoreagents; at least three, at least five, or even at least ten detectable secondary antibodies specific for the bridging antigens of the immunoreagents with high affinity; and instructions for using the kit.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 12A-FIG. 12D: Staining of a renal cancer core biopsy section with pairs of peptide-coupled primary and fluorescent high-affinity anti-peptide secondary antibodies. (A) Emission from the anti-IgA pair, where the secondary antibody is labeled with Dy491; (B) Emission from the anti-C3c pair, where the secondary antibody is labeled with Dy550; (C) Emission from the anti-COL4A5 pair, where the secondary antibody is labeled with Dy650; and (D) Emission from the anti-IgG pair, where the secondary antibody is labeled with Dy755.

FIG. 14A-FIG. 14E: Four-plex staining of triple-positive breast cancer markers in a single tissue section, detecting (A) CD3, (B) CD4, (C) CD8, and (D) CD20. Shown in (E) is an overlay of the four images.

FIG. 16A-FIG. 16E: Four-plex staining of triple-negative breast cancer tissue, detecting (A) CK5, (B) vimentin, (C) EGFR, (D) Ki-67, and (E) an overlay of the four images.

FIG. 17A-FIG. 17E: Four-plex staining of triple-negative breast cancer tissue detecting (A) CD8, (B) CD4, (C) CD20, (D) CD3, and (E) an overlay of the four images.

FIG. 24A-FIG. 24C: Results of a sequential tyramide staining amplification protocol. Two targets are identified on a single tissue section using the tyramide signal amplification protocol by peptide stripping of anti-peptide secondary antibody-HRP conjugates. Sequential staining of HER2 and ER by (1) rabbit anti-HER1-PEP5/anti-PEP5-HRP/tyramide-Dy490 (FIG. 24A), (2) stripping of the anti-PEP5-HRP with excess PEP5, and (3) staining of ER with rabbit-anti-ER-PEP-2/anti-PEP2-HRP/tyramide-Dy550 (FIG. 24B). FIG. 24C presents the overlay of the images of FIGS. 24A and 24B.

FIG. 29A shows an initial four-plex staining using a cocktail of immunoreagents targeting the immune markers CD8 (red in original), CD4 (blue in original), CD20 (green in original) and CD3 (magenta in original). After imaging, the immunoreagents were stripped by microwave heating. FIG. 29B shows the same section subsequently stained and imaged using a cocktail of immunoreagents targeting breast cancer markers HER2 (red in original), ER (blue in original), PR (green in original) and Ki-67 (magenta in original). The breast cancer panel signals were normalized to the signals generated by the immune marker panel signals.

DETAILED DESCRIPTION OF THE INVENTION

Antigen-Coupled Immunoreagents

Figure 1A:
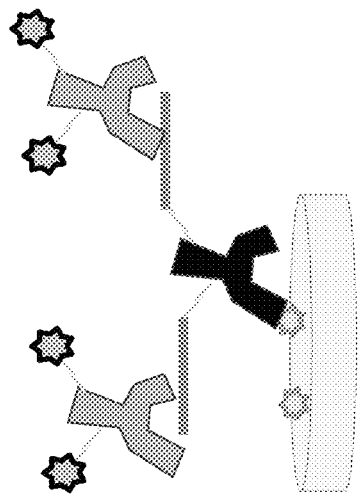
FIG. 1A-FIG. 1C: Schematic representation of an exemplary immunohistochemical assay using a bridging antigen-coupled primary antibody and a fluorescent secondary antibody specific for the bridging antigen. (A) Target antigen, represented as two gray stars, on the surface of a tissue or other sample of interest; (B) bridging antigen-coupled primary antibody bound to the target antigen; and (C) fluorescent secondary antibodies bound to the bridging antigen-coupled primary antibody, where the fluorophores on the secondary antibodies are represented as two black stars.

The instant disclosure provides in one aspect high-performance immunoreagents comprising a primary antibody and a bridging antigen, wherein the primary antibody and the bridging antigen are coupled, and wherein the bridging antigen is recognizable by a high-affinity detectable secondary antibody.

As is well known in the art, antibodies are glycoproteins belonging to the immunoglobulin superfamily. Antibodies typically comprise two large heavy chains and two small light chains, but various alternative or modified antibody structures may be suitably employed in the immunoreagents and compositions of the instant disclosure. For example, the antibodies may be natural antibodies, artificial antibodies, genetically engineered antibodies, monovalent antibodies, polyvalent antibodies, monoclonal antibodies, polyclonal antibodies, camelids, monobodies, single-chain variable fragments (scFvs) and/or fragments or derivatives thereof, including Fab fragments and F(ab')2 fragments. In certain applications, the antibodies may be monospecific, polyspecific, humanized, single-chain, chimeric, camelid single domain, shark single domain, synthetic, recombinant, hybrid, mutated, CDR-grafted antibodies, and/or fragments or derivatives thereof. In certain embodiments, the antibodies may be derived from any suitable mammalian species. For example, the antibodies may be derived from human, rat, mouse, goat, guinea pig, donkey, rabbit, horse, llama, or camel. In other embodiments, the antibodies may be derived from an avian species, such as, for example, chicken or duck. The origin of the antibody is defined by the genomic sequence, irrespective of the method of production. The antibodies of the instant immunoreagents may be of various isotypes, e.g., IgG, IgM, IgA, IgD, IgE or subclasses, e.g., IgG1, IgG2, IgG3, IgG4. The antibodies may be produced recombinantly, or by other means, which may include antibody fragments that are still capable of binding an antigen, for example, an Fab, an $F(ab)_2$, Fv, scFv, VhH, and/or V-NAR.

Suitable polyclonal antibodies for use in the instant immunoreagents may be produced through a variety of methods. For example, various animals may be immunized for this purpose by injecting them with an antigen of interest, for example a target biological molecule, or another molecule sharing an epitope of the target biological molecule. Such antigen molecules may be of natural origin or may be obtained by DNA recombination or synthetic methods, or fragments thereof, and the desired polyclonal antibodies may be obtained from the resulting sera and may be purified. Alternatively, intact cells that array the target biological molecule, or a suitable epitope of the target molecule, may be used. Various adjuvants may also be used for increasing the immune response to the administration of antigen, depending on the animal selected for immunization. Examples of these adjuvants include Freund's adjuvant, mineral gels such as aluminum hydroxide, surfactant substances such as polyanions, peptides, oil emulsions, haemocyanins, dinitrophenol, or lysolecithin.

Suitable monoclonal antibodies for use in the instant immunoreagents are typically obtained from hybridoma cells, which are prepared by the fusion of spleen cells from an animal that has been immunized with the desired antigen and myeloma cells. Cells expressing the desired antibody are then identified by their ability to bind the desired antigen. Stable hybridoma clones that produce significant amounts of the desired antibody may then be cultured to generate the antibody in useful amounts. These techniques are well known in the art.

The instant immunoreagents may be used in immunologic assays to identify and bind to a target antigen of interest in the assay, where the specificity of target binding is determined by the specificity of the antibody used to prepare the immunoreagent. In particular, the primary antibodies of the instant immunoreagents may be directed to a target antigen representing a protein or other antigenic molecule of interest, either within a cell or on the surface of a cell. The target antigen may in some cases be found within a subcellular organelle, for example within the nucleus of a cell or within the mitochondria. The target antigen may alternatively be displayed on a surface of interest, such as, for example, on an immunoblot or other type of two-dimensional medium. The target antigen may in some cases be in impure form, in partly purified form, or in purified form. In general, the target antigen may be on or in any suitable surface, or may even be free in solution, so long as it is available to interact specifically with the immunoreagent.

Moreover, the target antigen of interest may be any protein or other molecule of interest. In some embodiments, the target antigen may be a cellular marker that provides information about the disease state of a cell or tissue in an animal. For example, the target antigen may be the estrogen receptor (ER), the HER2/neu receptor (HER2), the progesterone receptor (PR), Ki67, EGFR, cytokeratin 1 (CK1), cytokeratin 5 (CK5), cytokeratin 6 (CK6), cytokeratin 7 (CK7), cytokeratin 14 (CK14), cytokeratin 17 (CK17), cytokeratin AE1/AE3, nestin, vimentin, ASMA, Ber-EP4, p16, p40, p53, p63, c-kit, various CD markers, including those listed below, or any other target antigen specifically recognizable by the primary antibody of the instant immunoreagents. In some embodiments, multiple cellular markers may be targeted. For example, in some embodiments, the target antigens may be ER and PR. In other embodiments, the target antigens may be HER2, ER, and PR or HER2, ER, and Ki67. In still other embodiments, the target antigens may be HER2, ER, PR, and Ki67. In yet still other embodiments, the target antigens may be Ki67, EGFR, and CK5. In even other embodiments, the target antigens may be Ki67, EGFR, CK5, and CK6.

Other specific target antigens include, without limitation, 4-1BB, AFP, ALK1, Amyloid A, Amyloid P, Androgen Receptor, Annexin A1, ASMA, BCA225, BCL-1, BCL-2, BCL-6, BerEP4, Beta-Catenin, Beta-HCG, BG-8, BOB-1, CA19-9, CA125, Calcitonin, Caldesmon, Calponin-1, Calretinin, CAM 5.2, CD1a, CD2, CD3, CD4, CD5, CD7, CD8, CD10, CD15, CD19, CD20, CD21, CD22, CD23, CD25, CD30, CD31, CD33, CD34, CD38, CD42b, CD43, CD45 LCA, CD45RO, CD56, CD57, CD61, CD68, CD79a, CD99, CD117, CD138, CD163, CDX2, CEA, Chromogranin A, CMV, c-kit, c-MET, c-MYC, Collagen Type IV, Complement 3c (C3c), COX-2, CXCR5, CK1, CK5, CK6, CK7, CK8, CK14, CK18, CK17, CK19, CK20, CK903, CK AE1, CK AE1/AE3, D2-40, Desmin, DOG-1, E-Cadherin, EGFR, EMA, ER, ERCC1, Factor VIII-RA, Factor XIIIa, Fascin, FoxP1, FoxP3, Galectin-3, GATA-3, GCDFP-15, GCET1, GFAP, Glycophorin A, Glypican 3, Granzyme B, HBME-1, *Helicobacter Pylori*, Hemoglobin A, Hep Par 1, HER-2, HHV-8, HMB-45, HSV 1/11, ICOS, IFNgamma, IgA, IgD, IgG, IgM, IL17, IL4, Inhibin, iNOS, Kappa Ig Light Chain, Ki-67, LAG-3, Lambda Ig Light Chain, Lysozyme, Mammaglobin A, MART-1/Melan A, Mast Cell Tryptase, MLH1, MOC-31, MPO, MSA, MSH2, MSH6, MUC1, MUC2, MUM1, MyoD1, Myogenin, Myoglobin, Napsin A, Nestin, NSE, Oct-2, OX40, OX40L, p16, p21, p2'7, p40, p53, p63, p504s, PAX-5, PAX-8, PD-1, PD-L1, PHH3, PIN-4, PLAP, PMS2, *Pneumocystis jiroveci (carinii)*, PgR, PSA, PSAP, RCC, S-100, SMA, SMM, Smoothelin, SOX10, SOX11, Surfactant Apoprotein A, Synaptophysin, TAG 72, TdT, Thrombomodulin, Thyroglobulin, TIA-1, TIM3, TRAcP, TTF-1, Tyrosinase, Uroplakin, VEGFR-2, Villin, Vimentin, WT-1, and the like.

In some embodiments, the primary antibody of the instant immunoreagents may be a cross-species reactive antibody that is directed against one or more sequences in an immunoglobulin molecule that do not vary significantly between different immunoglobulins within the same species. Such sequences are typically found within the so-called "constant region" of the immunoglobulin sequence. Recognition of these sequences is possible because the antibodies to be used in the immunoreagent are generated by immunization of a particular animal species, for example a goat, with isolated immunoglobulins from a different animal species, for example a mouse or a rabbit. An antibody generated in a goat against a mouse immunoglobulin is thus referred to as a "goat anti-mouse" antibody, and an antibody raised in a goat against a rabbit immunoglobulin is thus referred to as a "goat anti-rabbit" antibody. Polyclonal antibodies directed against a cross-species immunoglobulin can be useful in signal amplification in an immunologic assay due to their ability to recognize multiple epitopes in the cross-species primary antibody, as illustrated in the Examples section.

The bridging antigen of the instant immunoreagents is chosen to be recognizable by a secondary antibody, ideally at high affinity. The structure of the bridging antigen is therefore limited only by molecules that are capable of eliciting an immune response in a suitable animal or that can be used to generate suitable secondary antibodies by another means.

In some embodiments, the bridging antigen is a separate molecular entity from the primary antibody and is attached to the primary antibody by a chemical coupling reaction. In these embodiments, the bridging antigen is designed to contain at least one group capable of chemically coupling the bridging antigen to the primary antibody of the immunoreagent. That group may also be useful in chemically coupling the bridging antigen to a carrier protein or other suitable molecule in the preparation of the immunogen used to generate the secondary antibody. As described in more detail below, the coupling group may be chosen, in specific embodiments, so that the bridging antigen is conjugated to the primary antibody or carrier protein with high specificity and efficiency. In addition, coupling of the bridging antigen to the primary antibody should not significantly affect the ability of the bridging antigen to be recognized by the detectable secondary antibody. It is also desirable that the bridging antigen and coupling group not themselves have interfering absorbance or fluorescence, so as to avoid any background signals. Furthermore, bridging antigens and coupling groups should be available at high purity and ideally at low cost.

In some embodiments, the bridging antigen of the instant disclosure is a synthetic bridging antigen. In some embodiments, the bridging antigen is a natural product. In specific embodiments, the bridging antigen is a peptide.

Peptides, either synthetic or isolated from natural sources, have been used extensively to generate specific, high-affinity antibodies by various means, as is widely known and understood by those of ordinary skill in the art. The range of structural variation possible with peptides is nearly limitless, thus making them ideally suited for use as bridging antigens in the instant immunoreagents. Furthermore, synthetic peptides can be designed to include reactive groups to facilitate their coupling to primary antibodies, for example by including amino acid residues or other linking moieties incorporated on the C- or N-termini or internally during solid phase peptide synthesis or post-synthetically with desirable reactive properties within the peptide sequence. Peptidic bridging antigens may be of any size and may contain any suitable amino acids or other residue, both natural and artificial. They may be linear or circular. The peptidic bridging antigens are limited in these embodiments only by their ability to be conjugated to an antibody of interest and to be recognizable by a detectable secondary antibody.

In some embodiments, the bridging antigen is a peptide comprising a non-natural residue. For example, the bridging antigen may comprise a non-natural stereoisomer, such as a D-amino acid. In some embodiments, the non-natural residue may be a non-natural amino acid, such as a β-amino acid or the like. In some embodiments, the residues of the bridging antigen may be coupled using non-peptidic bonding, as would be understood by those of ordinary skill in the art.

In some embodiments, the bridging antigen is a peptide antigen that is engineered to be expressed as part of the protein sequence of the primary antibody itself. Examples of antigens that may be engineered into an antibody's primary sequence and thus serve as a bridging antigen include without limitation a Myc tag, a FLAG tag, an HA tag, an S tag, a Streptag, a His tag, or a V5 tag.

Other suitable bridging antigens usefully included in the instant immunoreagents include non-peptidic small-molecule antigens. As was true with peptidic bridging antigens, such antigens are limited only by their ability to be coupled to a primary antibody and to be recognizable by a detectable secondary antibody. Exemplary non-peptidic, small-molecule antigens, which may also be referred to herein as "haptens", include without limitation molecules such as nitrophenyl, dinitrophenyl, trinitrophenyl, digoxygenin, biotin, 5-bromodeoxyuridine, 3-nitrotyrosine, small-molecule drugs, and any other similar chemical tag.

In order to increase the number of binding sites per immunoreagent, it may be advantageous in some cases for a single bridging antigen to comprise a plurality of antigenic determinants or epitopes. Multiplicity of antigenic determinants in a bridging antigen may increase the number of secondary antibodies able to bind to the immunoreagent and thus the sensitivity of assays using the immunoreagent. In some embodiments, the plurality of antigenic determinants may comprise multiple copies of the same antigenic determinant, whereas in some embodiments, the plurality of antigenic determinants may comprise different antigenic determinants. In some embodiments, the plurality of antigenic determinants may comprise a linear repeating structure. More specifically, the linear repeating structure may be a linear repeating peptide structure. In some embodiments, the plurality of antigenic determinants may comprise at least two antigenic determinants, at least three antigenic determinants, at least four antigenic determinants, at least six antigenic determinants, or even more antigenic determinants.

In some embodiments, the bridging antigen may comprise a branched structure. For example, the branched structure may comprise a dendrimeric structure or the like, such as, for example, other polymerized constructs, as would be understood by those of ordinary skill in the art.

Furthermore, it should be understood that a bridging antigen comprising a plurality of antigenic determinants may comprise one or more polyethylene glycol linkers, and the like, between the antigenic determinants, for example between peptide antigenic determinants.

In some embodiments, the peptide antigenic determinants comprise at least four, at least six, at least eight, at least ten, at least 15, at least 20, or even more amino acid residues per antigenic determinant.

Where the primary antibody and bridging antigen are prepared from separate molecular entities, it should be understood that the coupling of the primary antibody and the bridging antigen may be achieved in a wide variety of ways, depending on the desired outcome. If control of the location and degree of coupling of the bridging antigen to the primary antibody is not important, non-specific chemical cross-linkers may be used to achieve the coupling. It is generally desirable, however, for the bridging antigen to be coupled to the primary antibody in a controlled and specific manner, and the choice of coupling method and agent can affect the location, degree, and efficiency of the coupling. For example, since reactive thiol groups are relatively uncommon on the surface of an antibody protein, the use of a thiol-reactive conjugation reagent will typically result in a relatively lower level of protein modification. Reactive amino groups are much more common on the surface of an antibody, so the use of amine-reactive conjugating reagents therefore typically results in a relatively higher level of protein modification by the bridging antigen. Additionally, the extent of modification of the antibody by the conjugating reagent may be titrated to some extent, for example by using a limited amount of the conjugating reagent relative to the number of reactive groups on the antibody.

In some immunoreagent embodiments, the primary antibody and the bridging antigen are coupled by a chemical coupling reaction through a conjugation moiety. In specific embodiments, the primary antibody and the bridging antigen are coupled by a high-efficiency conjugation moiety. Because the immunoreagents are preferably synthesized with relatively low molar concentrations of starting materials, and because those starting materials, for example primary antibodies, are expensive and are available in relatively small chemical quantities, it is highly desirable that formation of the conjugation moiety be as efficient and specific as possible and that its formation is complete, or nearly complete, at low molar concentrations of reactants. Specifically, it is desirable that the conjugation moiety be capable of coupling a primary antibody and a bridging antigen with rapid kinetics and/or high association constants and that the association reaction therefore be as efficient as possible in terms of its completion.

The high-efficiency conjugation moieties of the instant immunoreagents are typically formed, as described in more detail below, by separate modification of each component of the immunoreagent with complementary conjugating reagents. The complementary conjugating reagents additionally include a further reactive moiety, for example a thiol-reactive or an amino-reactive moiety, that allows the conjugating reagents to be attached to the relevant immunoreagent component, for example to the antibody and to the bridging antigen. After the antibody and the bridging antigen have been modified by the respective complementary conjugating reagents, typically at multiple locations on the antibody but at a single location on the bridging antigen, the complementary conjugating features on the modified components associate with one another in a highly efficient and specific manner to form the conjugation moiety.

Depending on the situation, the high-efficiency conjugation moiety of the instant immunoreagents may be a covalent or non-covalent conjugation moiety. In specific embodiments, the high-efficiency conjugation moiety is a covalent conjugation moiety, for example, a hydrazone, an oxime, or another suitable Schiff base moiety. Non-limiting examples of such conjugation moieties may be found, for example, in U.S. Pat. No. 7,102,024, which is incorporated by reference herein in its entirety for all purposes. These conjugation moieties may be formed by reaction of a primary amino group on the conjugating reagent attached to one component of the immunoreagent (e.g., a primary antibody) with a complementary carbonyl group on the conjugating reagent attached to the other component of the immunoreagent (e.g., a bridging antigen).

For example, hydrazone conjugation moieties may be formed by the reaction of a hydrazino group, or a protected hydrazino group, with a carbonyl moiety. Exemplary hydrazino groups include aliphatic, aromatic, or heteroaromatic hydrazine, semicarbazide, carbazide, hydrazide, thiosemicarbazide, thiocarbazide, carbonic acid dihydrazine, or hydrazine carboxylate groups. See U.S. Pat. No. 7,102,024. Oxime conjugation moieties may be formed by the reaction of an oxyamino group, or a protected oxyamino group, with a carbonyl moiety. Exemplary oxyamino groups are described below. The hydrazino and oxyamino groups may be protected by formation of a salt of the hydrazino or oxyamino group, including but not limited to, mineral acid salts, such as but not limited to hydrochlorides and sulfates, and salts of organic acids, such as but not limited to acetates, lactates, malates, tartrates, citrates, ascorbates, succinates, butyrates, valerates and fumarates, or any amino or hydrazino protecting group known to those of skill in the art (see, e.g., Greene et al. (1999) Protective Groups in Organic Synthesis (3rd Ed.) (J. Wiley Sons, Inc.)). The carbonyl moiety used to generate a Schiff base conjugation moiety is any carbonyl-containing group capable of forming a hydrazone or oxime linkage with one or more of the above hydrazino or oxyamino moieties. Preferred carbonyl moieties include aldehydes and ketones, in particular aromatic aldehydes and ketones. In preferred embodiments of the instant disclosure, the high-efficiency conjugation moiety is formed by the reaction of an oxyamino-containing component and an aromatic aldehyde-containing component in the presence of aniline catalysis (Dirksen et al. (2006) *Angew. Chem.* 45:7581-7584 (DOI: 10.1002/anie.200602877).

The high-efficiency conjugation moiety of the instant immunoreagents may alternatively be formed by a "click" reaction, for example the copper-catalyzed reaction of an azide-substituted component with an alkyne-substituted component to form a triazole conjugation moiety. See Kolb et al. (2001) *Angew. Chem. Int. Ed. Engl.* 40:2004; Evans (2007) *Aus. J. Chem.* 60:384. Copper-free variants of this reaction, for example the strain-promoted azide-alkyne click reaction, may also be used to form the high-efficiency conjugation moiety. See, e.g., Baskin et al. (2007) *Proc. Natl Acad. Sci. U.S.A.* 104:16793-97. Other click reaction variants include the reaction of a tetrazine-substituted component with either an isonitrile-substituted component (Stockmann et al. (2011) *Org. Biomol. Chem.* 9:7303) or a strained alkene-substituted component (Karver et al. (2011) *Bioconjugate Chem.* 22:2263).

The basic features of a click reaction are well understood by those of ordinary skill in the art. See Kolb et al. (2001) *Angew. Chem. Int. Ed. Engl.* 40:2004. Useful click reactions include generally but are not limited to [3+2] cycloadditions, such as the Huisgen 1,3-dipolar cycloaddition, and in particular the Cu(I)-catalyzed stepwise variant, thiol-ene click reactions, Diels-Alder reactions and inverse electron demand Diels-Alder reactions, [4+1] cycloadditions between isonitriles (isocyanides) and tetrazines, nucleophilic substitutions, especially to small strained rings like epoxy and aziridine compounds, carbonyl-chemistry-like formation of ureas, and some addition reactions to carbon-carbon double bonds. Any of the above reactions may be used without limitation to generate a covalent high-efficiency conjugation moiety in the instant immunoreagents.

In some embodiments, the conjugation moiety of the instant immunoreagents comprises a cleavable linker. Exemplary cleavable linkers usefully included in the instant high-efficiency conjugation moiety are known in the art. See, e.g., Leriche et al. (2012) *Bioorg. Med. Chem.* 20:571-582 (doi:10.1016/j.bmc.2011.07.048). Inclusion of a cleavable linker in the high-efficiency conjugation moiety allows for the selective cleavage of the bridging antigen from the primary antibody in the instant immunoreagents. Such selective cleavage may be advantageous in some immunoassay methods, for example where release of a bridging antigen and its associated secondary antibody.

In other embodiments, the high-efficiency conjugation moiety is a non-covalent conjugation moiety. Non-limiting examples of a non-covalent conjugation moiety include an oligonucleotide hybridization pair or a protein-ligand binding pair. In specific embodiments, the protein-ligand binding pair is an avidin-biotin pair, a streptavidin-biotin pair, or another protein-biotin binding pair (see generally *Avidin-Biotin Technology, Meth. Enzymol.* (1990) volume 184, Academic Press; *Avidin-Biotin Interactions: Methods and Applications* (2008) McMahon, ed., Humana; *Molecular Probes® Handbook*, Chapter 4 (2010)), an antibody-hapten binding pair (see generally *Molecular Probes® Handbook*, Chapter 4 (2010)), an S-peptide tag-S-protein binding pair (Kim and Raines (1993) *Protein Sci.* 2:348-56), or any other high-affinity peptide-peptide or peptide-protein binding pair. Such high-affinity non-covalent conjugation moieties are well known in the art. Reactive versions of the respective conjugating pairs, for example thiol-reactive or amino-reactive versions, are also well known in the art. These conjugating reagents may be used to modify the respective antibody and bridging antigen, in some cases at multiple locations on the antibody. The modified antibody and bridging antigen may then be mixed in order to allow the complementary features, for example the oligonucleotide hybridization pair or the protein-ligand binding pair, to associate with one another and form a non-covalent high-efficiency conjugation moiety. All of the above-described covalent and non-covalent linking groups are capable of highly efficient association reactions and are thus well suited for use in generation of the instant immunoreagents.

In some embodiments, the high-efficiency conjugation moiety is at least 50%, 80%, 90%, 93%, 95%, 97%, 98%, 99%, or even more efficient in coupling the antibody and the bridging antigen. In more specific embodiments, the high-efficiency conjugation moiety is at least 50%, 80%, 90%, 93%, 95%, 97%, 98%, 99%, or even more efficient at a protein concentration of no more than 0.5 mg/mL. In some embodiments, the efficiencies are achieved at no more than 0.5 mg/mL, no more than 0.2 mg/mL, no more than 0.1 mg/mL, no more than 0.05 mg/mL, no more than 0.02 mg/mL, no more than 0.01 mg/mL, or even lower protein concentrations. Since bridging antigens are typically used in excess of antibodies in the preparation of the instant immunoreagents, the efficiency of a linking reaction is typically judged by the extent of conversion of the antibody component of the association reaction to immunoreagent product. For example, a high-efficiency conjugation moiety that is at least 50% efficient in coupling an antibody and a bridging antigen is a moiety that results in at least 50% of the starting antibody being converted to an immunoreagent with the desired number of bridging antigens per antibody in the association reaction.

In another aspect, the disclosure provides immunoreagent compositions, also referred to as immunoreagent panels, comprising a plurality of the above-described immunoreagents. In embodiments, the composition comprises at least 3, 5, 10, 20, 30, 50, 100, or even more of the immunoreagents. In some embodiments, the primary antibodies of the included immunoreagents are specific for cellular markers. In specific embodiments, the cellular markers are at least ER and PR. In other specific embodiments, the cellular markers are at least HER2, ER, and PR or at least HER2, ER, and Ki67. In still other specific embodiments, the cellular markers are at least HER2, ER, PR, and Ki67. In yet still other specific embodiments, the cellular markers are at least Ki67, EGFR, and CK5. In even other specific embodiments, the cellular markers are at least Ki67, EGFR, CK5, and CK6, or are at least CK5, CK6, and Ki-67. In still other specific embodiments, the cellular markers are at least CK5, EGFR, p40, and Ki-67, or are at least IgA, complement 3c (C3c), collagen IV alpha chain 5 (COL4A5), and IgG. In some embodiments, the bridging antigens of the included immunoreagents are peptides.

In some embodiments, the immunoreagent compositions of the instant disclosure are specific for cellular markers on immune cells, for example, CD3, CD4, CD8, CD20, CD68, and/or FoxP3, in any combination, and any of the cellular markers listed above. In some embodiments, the immunoreagent compositions are specific for markers relating to checkpoint pathways, such as, for example, CTLA-4, CD152, PD-1, PD-L1, and the like.

Detectable Secondary Antibodies

As noted above, the bridging antigens of the instant immunoreagents are recognizable by detectable secondary antibodies. In order to increase sensitivity and decrease background in immunologic assays using the instant immunoreagents, it is generally desirable to maximize the affinity and/or specificity of each detectable secondary antibody for its corresponding bridging antigen. As is understood by those of ordinary skill in the art, affinities of antibodies for antigens are typically assessed using an equilibrium parameter, the dissociation constant or "$K_D$". For a given concentration of antibody, the dissociation constant roughly corresponds to the concentration of antigen at which half the antibody is bound to an antigen and half the antibody is not bound to an antigen. Accordingly, a lower dissociation constant corresponds to a higher affinity of an antibody for the antigen.

The dissociation constant is also related to the ratio of the kinetic rate constants for dissociation and association of the antibody and the antigen. Dissociation constants may therefore be estimated either by equilibrium binding measurements or by kinetic measurements. Such approaches are well known in the art. For example, antibody-antigen binding parameters are routinely determined from the kinetic analysis of sensorgrams obtained using a Biacore surface plasmon resonance-based instrument (GE Healthcare, Little Chalfont, Buckinghamshire, UK), an Octet bio-layer interferometry system (Pall ForteBio Corp., Menlo Park, CA), or the like. See, for example, U.S. Patent Application Publication No. 2013/0331297 for a description of the determination of dissociation constants for a series of antibody clones and their corresponding peptide antigen binding partners.

Typical antibodies have equilibrium dissociation constants in the range from micromolar to high nanomolar (i.e., $10^{-6}$ M to $10^{-8}$ M). High affinity antibodies generally have equilibrium dissociation constants in the lower nanomolar to high picomolar range (i.e., $10^{-8}$ M to $10^{-10}$ M). Very high affinity antibodies generally have equilibrium dissociation constants in the picomolar range (i.e., $10^{-10}$ M to $10^{-12}$ M). Antibodies against peptides or other large molecules typically have higher affinities (lower $K_D$s) for their antigens than antibodies against small-molecule haptens, which may display dissociation constants in the micromolar range or even higher.

The secondary antibodies of the instant immunoreagents may be optimized in order to increase their affinity for antigen-coupled primary antibodies. For example, U.S. Patent Application Publication No. 2013/0331297 discloses methods for identifying antibody clones with high affinities that may be suitably modified to generate the detectable secondary antibodies utilized in the instant immunoreagents. In these methods, a short DNA fragment encoding a synthetic peptide is fused to the heavy chains of the gene pool encoding an antibody library of interest, and yeast cells are transformed to generate a yeast display antibody library. The yeast cells are screened with a high-speed fluorescence-activated cell sorter (FACS) to isolate high-affinity antibody clones with high specificity. Compared to other yeast display systems such as Aga2, this system has an added advantage that the transformed yeast cells secrete sufficient amounts of antibodies into the culture medium to allow the culture media of the individual yeast clones to be assayed directly to determine specificity and affinity of the expressed antibodies, without requiring the additional steps of cloning and antibody purification for identification of candidate clones with the desired specificity and affinity.

The above-described yeast display library system makes use of antibody libraries generated from immunized rabbits to produce rabbit monoclonal antibodies with high specificity and affinity, thus harnessing the superior ability of the rabbit immune system to generate antibodies against small haptens or peptides with the efficiency of yeast display to isolate antibody clones with superior affinity and specificity. Using this approach, a panel of rabbit monoclonal antibodies against small molecules, peptides, and proteins was generated with antibody affinities in the range of <0.01 to 0.8 nM. These affinities surpass the affinities of most monoclonal antibodies from rodents generated using traditional hybridoma technology. The approach also overcomes inherent issues of low fusion efficiency and poor stability encountered with rabbit hybridoma technology.

While the above-described yeast display library system is one approach for optimizing binding affinities of the secondary antibodies used in the instant immunoreagent compositions, it should be understood that any suitable approach may be used to optimize the affinities without limitation. In some cases, suitable high-affinity antibodies may be available without optimization.

Accordingly, in some embodiments, the detectable secondary antibody is specific for the bridging antigen with a dissociation constant of at most 100 nM, at most 30 nM, at most 10 nM, at most 3 nM, at most 1 nM, at most 0.3 nM, at most 0.1 nM, at most 0.03 nM, at most 0.01 nM, at most 0.003 nM, or even lower. In more specific embodiments, the detectable secondary antibody is specific for the bridging antigen with a dissociation constant of at most 1 nM, at most 0.3 nM, at most 0.1 nM, at most 0.03 nM, at most 0.01 nM, at most 0.003 nM, or even lower. In even more specific embodiments, the detectable secondary antibody is specific for the bridging antigen with a dissociation constant of at most 100 pM, at most 30 pM, at most 10 pM, at most 3 pM, or even lower.

The secondary antibody of the instant immunoreagents is a detectable secondary antibody, and in embodiments it therefore comprises a detectable label. As would be understood by those of ordinary skill in the art, the detectable label of the detectable secondary antibody should be capable of suitable attachment to the antibody, and the attachment should be carried out without significantly impairing the interaction of the antibody with the bridging antigen.

In some embodiments, the detectable label may be directly detectable, such that it may be detected without the need for any additional components. For example, a directly detectable label may be a fluorescent dye, a biofluorescent protein, such as, for example, a phycoerythrin, an allophycocyanin, a peridinin chlorophyll protein complex ("PerCP"), a green fluorescent protein ("GFP") or a derivative thereof (for example, a red fluorescent protein, a cyan fluorescent protein, or a blue fluorescent protein), luciferase (e.g., firefly luciferase, *renilla* luciferase, genetically modified luciferase, or click beetle luciferase), or coral-derived cyan and red fluorescent proteins (as well as variants of the red fluorescent protein derived from coral, such as the yellow, orange, and far-red variants), a luminescent species, including a chemiluminescent species, an electrochemiluminescent species, or a bioluminescent species, a phosphorescent species, a radioactive substance, a nanoparticle, a SERS nanoparticle, a quantum dot or other fluorescent crystalline nanoparticle, a diffracting particle, a Raman particle, a metal particle, including a chelated metal, a magnetic particle, a microsphere, an RFID tag, a microbarcode particle, or a combination of these labels.

In other embodiments, the detectable label may be indirectly detectable, such that it may require the employment of one or more additional components for detection. For example, an indirectly detectable label may be an enzyme that effects a color change in a suitable substrate, as well as other molecules that may be specifically recognized by another substance carrying a label or that may react with a substance carrying a label. Non-limiting examples of suitable indirectly detectable labels include enzymes such as a peroxidase, an alkaline phosphatase, a glucose oxidase, and the like. In specific embodiments, the peroxidase is a horseradish peroxidase or a soybean peroxidase. Other examples of indirectly detectable labels include haptens such as, for example, a small molecule or a peptide. Non-limiting exemplary haptens include nitrophenyl, dinitrophenyl, digoxygenin, biotin, a Myc tag, a FLAG tag, an HA tag, an S tag, a Streptag, a His tag, a V5 tag, a ReAsh tag, a FlAsh tag, a biotinylation tag, an Sfp tag, or another chemical or peptide tag.

In specific embodiments, the detectable label is a fluorescent dye. Non-limiting examples of suitable fluorescent dyes may be found in the catalogues of Life Technologies/Molecular Probes (Eugene, OR) and Thermo Scientific Pierce Protein Research Products (Rockford, IL), which are incorporated by reference herein in their entireties. Exemplary dyes include fluorescein, rhodamine, and other xanthene dye derivatives, cyanine dyes and their derivatives, naphthalene dyes and their derivatives, coumarin dyes and their derivatives, oxadiazole dyes and their derivatives, anthracene dyes and their derivatives, pyrene dyes and their derivatives, and BODIPY dyes and their derivatives. Preferred fluorescent dyes include the DyLight fluorophore family, available from Thermo Scientific Pierce Protein Research Products.

In some embodiments, the detectable label may not be attached directly to the secondary antibody, but may be attached to a polymer or other suitable carrier intermediate that allows larger numbers of detectable labels to be attached to the secondary antibody than could normally be bound.

In specific embodiments, the detectable label is an oligonucleotide barcode tag, for example the barcode tags disclosed in PCT International Patent Publication No. WO2012/071428A2, the disclosure of which is incorporated herein by reference in its entirety. Such detectable labels are particularly advantageous in immunoassays involving the isolation and/or sorting of targeted samples, for example in flow cytometry-based multiplexed immunodetection assays, and the like. These labels are also advantageous in immunoassays where the levels of target antigen in a sample are low, and extreme sensitivity of detection is required.

In some embodiments, the detectable secondary antibodies of the instant disclosure may comprise multiple detectable labels. In these embodiments, the plurality of detectable labels associated with a given secondary antibody may be multiple copies of the same label or may be a combination of different labels that result in a suitable detectable signal.

In some immunoreagent embodiments, it may be advantageous for purposes of increasing the signal output from the reagent to attach one or more detectable labels to the bridging antigen of the primary antibody. The detectable labels usefully attached to the bridging antigen can be any of the above-described detectable labels. Such detectable labels should ideally overlap in detectability with the detectable label of the secondary antibody, so that the signals from a primary antibody and secondary antibody pair will be additive. Furthermore, the attachment of a detectable label to a bridging antigen should ideally not significantly affect the binding of the secondary antibody to the bridging antigen on the primary antibody. Likewise, the binding of the secondary antibody to the bridging antigen should ideally not significantly affect the detectability of the detectable label.

In preferred embodiments, the detectable label of the bridging antigen is a fluorophore. In more preferred embodiments, the detectable label of the bridging antigen and the detectable label of the secondary antigen are both fluorophores. In other preferred embodiments, the detectable label of the bridging antigen and the detectable label of the secondary antibody are both detectable by fluorescence at the same wavelength. In still other preferred embodiments, the detectable label of the bridging antigen and the detectable label of the secondary antibody are the same.

It should be understood in the context of the instant disclosure, that the terms "primary antibody" and "secondary antibody" may be used in a somewhat different way than the terms are sometimes applied in the art of immunologic assays. Accordingly, the instant primary antibodies should be broadly interpreted as targeting any molecule of interest, including other antibodies, and the instant secondary antibodies should be broadly interpreted as targeting a bridging antigen, where the bridging antigen is coupled to the primary antibody. In other contexts, an antibody that targets another antibody, for example from another species, may be considered to be a secondary antibody, whereas that antibody here could be a primary antibody. The terms "primary antibody" and "secondary antibody" in the instant disclosure should therefore be considered limiting only as the terms are used in the claims to distinguish one antibody from the other.

Immunoreagent Composition Pairs

According to another aspect, the instant disclosure provides immunoreagent compositions comprising a primary antibody coupled to a bridging antigen, and a detectable secondary antibody specific for the bridging antigen. In these compositions, the detectable secondary antibody and the antigen-conjugated primary antibody are paired due to the high affinity of the secondary antibody for the bridging antigen. It is understood that the paired composition will form whenever the separate components of the composition are mixed together in aqueous solution, for example whenever the reagents are used together in an immunologic assay.

Immunoreagents comprising a primary antibody and coupled bridging antigen are described in detail above, as are detectable secondary antibodies suitable for use in the instant immunoreagent pairs. As would be understood by those of ordinary skill in the art, a composition comprising these components finds utility in the practice of immunologic assays, including IHC, cytometry, flow cytometry, such as fluorescence-activated cell sorting, microscopic imaging, pretargeting imaging, and other types of in vivo tumor and tissue imaging, high content screening (HCS), immunocytochemistry (ICC), immunomagnetic cellular depletion, immunomagnetic cell capture, sandwich assays, general affinity assays, enzyme immuno-assay (EIA), enzyme linked immuno-assay (ELISA), ELISpot, mass cytometry (CyTOF), arrays including microsphere arrays, multiplexed microsphere array, microarray, antibody array, cellular array, solution phase capture, lateral flow assays, chemiluminescence detection, infrared detection, blotting methods, including Western blots, Southwestern blot, dot blot, tissue blot, and the like, or combinations thereof.

Multiplexed Immunoreagent Pairs

As noted above, current immunologic assays are severely limited in their ability to detect multiple antigens in a single sample due to the limited functionality of traditional secondary antibodies. As is understood by those of ordinary skill in the art, antibodies directed against a cross-species immunoglobulin are often used in such immunologic assays to label primary antibodies in a sample of interest. The use of such cross-species secondary antibodies to detect primary antibodies in an immunologic assay provides some flexibility in the assay, because a single detectable cross-species secondary antibody can be used to stain a wide variety of unlabeled primary antibodies, so long as the primary antibodies are available from the same species. The use of cross-species secondary antibodies may in some situations also provide increased sensitivity in the assays by amplifying the detectable signal: a single primary antibody may bind multiple secondary antibodies, particularly when the secondary antibodies are polyclonal antibodies and can bind to multiple epitopes, and the secondary antibodies may be polymerized and/or carry multiple detectable labels. Such signal amplification may thereby increase the sensitivity of the assay for a given primary antibody. The use of a single detectable secondary antibody against multiple primary antibodies is also relatively convenient and inexpensive, because each primary antibody does not need to be individually labeled with a detectable agent.

Although the use of cross-species secondary antibodies provides some advantages in performing immunologic assays, such use can be disadvantageous if primary antibodies are not available from the same species for all target antigens of interest. In addition, the use of cross-species secondary antibodies also severely limits the multiplexing capabilities of a traditional immunologic assay, because only a single primary antibody at a time can be detected in such assays. While it is possible to sequentially label the same tissue section or other sample of interest by sequential treatment with a first primary antibody, staining with the secondary antibody, bleaching or washing the sample to remove the detectable agent, repeating the treatment with a second primary antibody, and so on, and it is possible to stain sequential tissue sections separately with singleplexed reagents in order to assess multiple cellular markers, such procedures are unwieldy, unreliable, and severely limited in the scale of multiplexing possible. The limitations of current multiplexing capabilities have been recently reviewed by Stack et al. (2014) *Methods* 70:46-58 (DOI: 10.1016/j.ymeth.2014.08.016).

The immunoreagents of the instant disclosure overcome the above limitations by eliminating the need to use cross-species secondary antibodies in a multiplexed immunologic assay. Instead, a multiplicity of the instant immunoreagent composition pairs, each pair having a different bridging antigen and a correspondent different secondary antibody, may be used simultaneously in a single immunologic assay to achieve a high level of multiplexing with high sensitivity, high specificity, and low background. The bridging antigen effectively substitutes functionally for the cross-species recognition of the primary antibody by the detectable secondary antibody. It should be understood that the choice of bridging antigen is limited only by the requirement that it be capable of being coupled to the primary antibody of interest and that it be recognizable by the secondary antibody, ideally at high affinity. Because there are virtually limitless bridging antigen structures that meet these criteria, the level of multiplexing possible using the instant immunoreagents is likewise virtually limitless. The only other limitation is that the different detectable secondary antibodies be detectably distinguishable from one another, and from any other background signals in the sample, in order to differentiate target antigens in the assay. With the wide array of detectable labels now available for use in immunologic assays, however, this requirement is not a significant limitation. Examples of fluorescent dyes useful in achieving high levels of multiplexing in fluorescence-based assays are described in Stack et al. (2014) *Methods* 70:46-58 (DOI: 10.1016/j.ymeth.2014.08.016).

Accordingly, in embodiments, the instant disclosure provides immunoreagent compositions comprising a plurality of primary antibodies coupled to a plurality of bridging antigens and a plurality of detectable secondary antibodies. Each bridging antigen in these compositions is coupled to a different primary antibody, and at least one detectable secondary antibody binds to each bridging antigen with high affinity. The plurality of antigen-coupled primary antibodies and detectable secondary antibodies in these compositions may be any of the immunoreagent composition pairs described in the previous section.

In specific embodiments, the composition comprises at least three immunoreagent composition pairs. In more specific embodiments, the composition comprises at least five immunoreagent composition pairs. In still more specific embodiments, the composition comprises at least ten immunoreagent composition pairs. In even more specific embodiments, the composition comprises at least 20, 30, 50, 100, or even more immunoreagent composition pairs.

Immunoreagent Panels

The immunoreagents described above can be combined in pre-defined groups to create diagnostic panels for use in monitoring the expression of specific combinations of cellular markers in certain tissues of interest, in particular in diseased tissues of interest such as in tumor tissues. Such panels are of use in diagnostic assays to identify such diseased tissues and are further of use as companion diagnostics, where the panels are used to monitor levels of cellular markers in the diseased tissues over time during the course of a particular treatment regimen. Such companion diagnostics provide for the timely and reliable assessment of the effectiveness of the treatment regimen and may further allow treatment dosages and frequency to be optimized for a particular patient. As described above, the monitoring of target tissues using current IHC techniques is limited to one or two primary antibodies per tissue section or requires the staining of tissue sections separately or sequentially with different antibodies. In contrast, and as described above, the immunoreagent panels disclosed herein allow high levels of multiplexing, such that the staining of a tissue or other sample of interest can be performed simultaneously with large numbers of primary antibodies in single tissue sections or other samples.

According to this aspect, the invention therefore provides immunoreagent compositions comprising at least three immunoreagents of the instant disclosure. In specific embodiments, the immunoreagent compositions comprise at least five, at least at least ten, at least 15, at least 20, at least 30, or even more immunoreagents of the instant disclosure, as described in detail above.

Of particular interest is the use of the instant immunoreagent panels to profile tissue samples in patients being treated using immunotherapeutic regimens, for example in the treatment of autoimmune diseases and cancer. Recent advances in the blockade of checkpoint pathways, for example using antibodies targeting the cytotoxic T lymphocyte-associated antigen-4 (CTLA-4, CD152) (e.g., ipilimumab) or antibodies targeting the programed death receptors or their ligands (PD-1 or PD-L1) (e.g., pembrolizumab, nivolumab, pidilizumab, and the like), have been shown to be especially effective. See, e.g., Adams et al. (2015) *Nature Rev. Drug Discov.* 14:603-22; Mahoney et al. (2015) *Nature Rev. Drug Discov.* 14:561-84; Shin et al. (2015) *Curr. Opin. Immunol.* 33:23-35.

Other recently approved anticancer agents target other cell-surface proteins or gene products that are upregulated or amplified in tumors and other diseases (see, e.g., rituximab against CD20 in lymphoma cells, trastuzumab against HER2/neu in breast cancer cells, cetuximab against EGFR in various tumor cells, bevacizumab against VEGF in a variety of cancer cells and in the eye, and denosumab against osteoclasts in bone). The profiling of tissue samples from patients being treated with these agents is thus also of great current interest in clinical medicine.

Likewise, tissue samples obtained from patients either prior to or during treatment with anticancer agents may also benefit from molecular profiling. For example, patients being treated with imatinib, lenalidomide, pemetrexed, bortezomib, leuprorelin, abiraterone acetate, ibrutinib, capecitabine, erlotinib, everolimus, sirolimus, nilotinib, sunitinib, sorafenib, and the like can be advantageously monitored by the profiling of tissues, in particular diseased tissues, using the instant immunoreagent panels.

Methods and systems for the molecular profiling of tissues, including the analysis of immune modulators, and the use of those profiles to assess and monitor disease treatments have also been reported. See, e.g., U.S. Pat. Nos. 8,700,335 B2; 8,768,629 B2; 8,831,890 B2; 8,880,350 B2; 8,914,239 B2; 9,053,224 B2; 9,058,418 B2; 9,064,045 B2; 9,092,392 B2; PCT International Patent Publication No. WO 2015/116868. Such approaches are advantageously performed using suitable panels of the instant immunoreagents.

Exemplary panels target combinations of tumor cell, immune cell, and various disease-related marker antigens, including the following markers:

4-1BB, AFP, ALK1, Amyloid A, Amyloid P, Androgen Receptor, Annexin A1, ASMA, BCA225, BCL-1, BCL-2, BCL-6, BerEP4, Beta-Catenin, Beta-HCG, BG-8, BOB-1, CA19-9, CA125, Calcitonin, Caldesmon, Calponin-1, Calretinin, CAM 5.2, CD1a, CD2, CD3, CD4, CD5, CD7, CD8, CD10, CD15, CD19, CD20, CD21, CD22, CD23, CD25, CD30, CD31, CD33, CD34, CD38, CD42b, CD43, CD45 LCA, CD45RO, CD56, CD57, CD61, CD68, CD79a, CD99, CD117, CD138, CD163, CDX2, CEA, Chromogranin A, CMV, c-kit, c-MET, c-MYC, Collagen Type IV, Complement 3c (C3c), COX-2, CXCR5, CK1, CK5, CK6, CK7, CK8, CK14, CK18, CK17, CK19, CK20, CK903, CK AE1, CK AE1/AE3, D2-40, Desmin, DOG-1, E-Cadherin, EGFR, EMA, ER, ERCC1, Factor VIII-RA, Factor XIIIa, Fascin, FoxP1, FoxP3, Galectin-3, GATA-3, GCDFP-15, GCET1, GFAP, Glycophorin A, Glypican 3, Granzyme B, HBME-1, *Helicobacter Pylori*, Hemoglobin A, Hep Par 1, HER-2, HHV-8, HMB-45, HSV 1/11, ICOS, IFNgamma, IgA, IgD, IgG, IgM, IL17, IL4, Inhibin, iNOS, Kappa Ig Light Chain, Ki-67, LAG-3, Lambda Ig Light Chain, Lysozyme, Mammaglobin A, MART-1/Melan A, Mast Cell Tryptase, MLH1, MOC-31, MPO, MSA, MSH2, MSH6, MUC1, MUC2, MUM1, MyoD1, Myogenin, Myoglobin, Napsin A, Nestin, NSE, Oct-2, OX40, OX40L, p16, p21, p27, p40, p53, p63, p504s, PAX-5, PAX-8, PD-1, PD-L1, PHH3, PIN-4, PLAP, PMS2, *Pneumocystis jiroveci (carinii)*, PgR, PSA, PSAP, RCC, 5-100, SMA, SMM, Smoothelin, SOX10, SOX11, Surfactant Apoprotein A, Synaptophysin, TAG 72, TdT, Thrombomodulin, Thyroglobulin, TIA-1, TIM3, TRAcP, TTF-1, Tyrosinase, Uroplakin, VEGFR-2, Villin, Vimentin, WT-1, and the like.

Preferably, the panels target one or more of the following markers: CD4, CD8, CD20, CD68, PD-1, PD-L1, FoxP3, SOX10, Granzyme B, CD3, CD163, IL17, IL4, IFNgamma, CXCR5, FoxP1, LAG-3, TIM3, CD34, OX40, OX40L, ICOS, and 4-1BB.

The panels are provided either in kit form or as a group of the different immunoreagents provided separately for use in the methods for immunological assay described in detail below. In particular, the panels are used in multiplexed methods, where samples are reacted with multiple immunoreagents for simultaneous detection. The immunoreagents are any of the above-described immunoreagents, in particular those comprising a primary antibody specific for any of the above-defined target antigens, and a bridging antigen, wherein the primary antibody and the bridging antigen are coupled, and wherein the bridging antigen is recognized by a detectable secondary antibody with high affinity.

In specific embodiments, the panels target the following exemplary combinations of cellular markers:
CD4, CD8, CD68, and PD-L1;
CD4, CD8, FoxP3, and CD68 (for any solid tumor);
CD8, CD68, PD-L1, plus tumor associated marker (for head and neck and pancreatic tumors);
SOX10, CD8, PD-1, and PD-L1 (for melanoma);
CD4, CD8, CD20, and cytokeratin (for breast cancer TIL);
CD8, CD34, FoxP3, and PD-L1 (for melanoma immunology);
CD8, CD34, PD-L1, and FoxP1 (for cancer immunology);
CD3, PD1, LAG-3, and TIM3 (for T cell exhaustion);
CD4 and FoxP3 (for Treg);
CD4 and IL17 (for Th17);
CD8 and Granzyme B (for activated CD8);
CD4 and CXCR5 (for TFh);
CD4 and IL4 (for Th2);
CD4 and IFNg (for Th1);
CD4, CD8, CD3, and CD20 (for general lymphocytes);
CD4, CD8, CD68, and CD20 (for lymphocytes and macrophages);

CD4, FoxP3, CD8, and CD20 (for Treg and lymphocytes);

CD4, FoxP3, CD8, and Granzyme B (for Treg and Act CTL);

CD68 (for macrophages);

CD68 and CD163 (for M2 macrophages);

CD20 (for B cells); and

OX40, OX40L, ICOS, and 41BB (for other molecules of interest)

Methods of Immunologic Assay

In another aspect, the instant disclosure provides methods of immunologic assay, comprising reacting an immunoreagent with a target antigen, reacting a detectable secondary antibody with the immunoreagent, wherein the detectable secondary antibody binds to the bridging antigen of the immunoreagent with high affinity, and detecting the bound detectable secondary antibody. The immunoreagent and detectable secondary antibody in these methods may usefully be any of the above-described immunoreagents and detectable secondary antibodies, in any suitable combination.

In embodiments, the method of detection is an immunohistochemical method. As described above, immunohistochemical staining is widely used technique that is applied frequently to the diagnosis of abnormal cells, such as tumor cells. Specific molecular markers are characteristic of a particular tumor cell, for example a breast cancer cell. IHC is also frequently used to understand the distribution and localization of biomarkers and differentially expressed proteins in different parts of a biological tissue.

In specific embodiments, the target antigen is present within a tissue section. Detection of antigens within tissue sections is well understood by those of skill in the clinical pathology arts. Exemplary methods of detecting antigens within a tissue section are provided, for example, in *Immunohistochemical Staining Methods*, 6$^{th}$ ed. (Dako/Agilent Technologies). It should be understood that solid tissue samples, typically following a fixation process, can be sectioned in order to expose one or more target antigens of interest on the surface of the sample. The analysis of consecutive tissue sections, i.e., sections that had been adjacent, or nearly adjacent, to one another in the original tissue sample, enables the recreation of a three-dimensional model of the original tissue sample, or the increased capability for multiplexing of target antigens, as will be described in more detail below. In preferred embodiments, the first target antigen is a target antigen within a tissue section of a tumor sample.

In other specific embodiments, the antigen detected by the method is in or on a cell. Such detection is well understood, for example, by those of skill in the art of cytometry. In some embodiments, the antigen may be on the surface of a cell. In other embodiments, the antigen may be in the cytoplasm of a cell. In still other embodiments, the antigen may be in the nucleus of a cell. In some embodiments, the antigen may be in more than one location in the cell.

The tissue analyzed according to the above methods may be any suitable tissue sample. For example, in some embodiments, the tissue may be connective tissue, muscle tissue, nervous tissue, or epithelial tissue. Likewise, the tissue analyzed may be obtained from any organ of interest. Non-limiting examples of suitable tissues include breast, colon, ovary, skin, pancreas, prostate, liver, kidney, heart, lymphatic system, stomach, brain, lung, and blood.

In some embodiments, the detecting step is a fluorescence detection step. Suitable fluorescence detection labels are described in detail above.

In some embodiments, the method of detection further comprises the step of sorting cells that have bound the detectable secondary antibody. Cell sorting is a well understood technique within the art of flow cytometry. Exemplary flow cytometry methods of detection are provided, for example, in *Practical Flow Cytometry*, 4$^{th}$ ed., Shapiro, Wiley-Liss, 2003; *Handbook of Flow Cytometry Methods*, Robinson, ed., Wiley-Liss, 1993; and *Flow Cytometry in Clinical Diagnosis*, 4$^{th}$ ed., Carey et al., eds, ASCP Press, 2007. The use of hydrazone-linked antibody-oligonucleotide conjugates in quantitative multiplexed immunologic assays, in particular, in quantitative flow cytometric assays, is described in PCT International Publication No. WO 2013/188756 and in Flor et al. (2013) *Chembiochem.* 15:267-75.

In some embodiments, the method of immunologic assay comprises reacting additional immunoreagents with additional target antigens in multiplexed assays, wherein the additional immunoreagents are any of the above-defined immunoreagents specific for the additional target antigens, reacting the additional immunoreagents with additional detectable secondary antibodies, wherein the additional detectable secondary antibodies bind to the bridging antigens of the additional immunoreagents with high affinity, and detecting the bound detectable additional secondary antibodies. It should be understood that the order of reaction of the additional immunoreagents and secondary antibodies in the multiplexed methods may be varied in any suitable way in order to achieve desired results, as would be understood by those of ordinary skill in the art. In some embodiments, all of the different immunoreagents may be added simultaneously to a target sample containing multiple target antigens. In other embodiments, the different immunoreagents may be added sequentially, in any order. Likewise with the secondary antibodies, which may be added either simultaneously or sequentially, in any order. In the multiplexed assays, the methods may detect 2, 3, 5, 10, 20, 30, 50, 100, or even more different target antigens in a single assay. As described in detail above, the ability of the instant immunoreagents to be used in such higher-level multiplexed immunologic assays is a major advantage of the instant immunoreagents. In particular, and as illustrated in the Examples, these immunoreagents enable immunologic assays with exquisite sensitivity, selectivity, and extremely low levels of background signal.

In some embodiments, the instant methods of immunologic assay comprise the analysis of adjacent or nearly adjacent sections of a fixed tissue sample in order to increase the level of multiplexing of detectable antigens possible for a given tissue sample or to recreate a three-dimensional image of the sample. For example, in some embodiments the methods further comprise the step of reacting a second immunoreagent with a second target antigen on a second sample. In some of these methods, the first sample and the second sample may be serial sections of a tissue sample (i.e., sections that are adjacent, or nearly adjacent, to one another in the sample), and the second immunoreagent is any of the above immunoreagents specific for the second antigen. The methods further comprise the step of reacting a second detectable secondary antibody with the second immunoreagent, wherein the second detectable secondary antibody is specific for the bridging antigen of the second immunoreagent with high affinity, and the step of detecting the second detectable secondary antibody that is associated with the bridging antigen of the second immunoreagent.

It will be understood that the immunoassay of serial sections of a given tissue sample provides for the greatly increased multiplexing of antigen detection in view of current hardware and software limitations. For example, although the immunoreagents and methods described herein in principle allow unlimited multiplexing due to the unlimited variation in bridging antigens and secondary antibodies, such assays are nevertheless limited by the number of fluorescent dyes that can currently be distinguished simultaneously on a single tissue section with available detection devices. Serial sections of the same tissue sample can, however, be stained with different panels of primary antibodies to identify different sets of target antigens by the reuse of the same panel of detectable labels, for example fluorescent labels, on the different sections. The detectable labels may be attached to the same set of secondary antibodies used in labeling the first sample section, in which case the second panel of primary antibodies would be labeled with the same set of bridging antigens as used with the first panel of antibodies. Alternatively and optionally, the detectable labels may be attached to a different set of secondary antibodies used in labeling the first sample section, in which case the second panel of primary antibodies would be labeled with a different set of bridging antigens than were used with the first panel of antibodies.

It will also be understood that the immunoassay of serial sections of a given tissue sample enable the analysis of target tissue antigens in a third dimension, thus providing further information regarding the overall structure of the sample tissue, for example by tomographic techniques. In some embodiments, the first sample and the second sample may not be serial sections of the sample but may instead be separated in space within the original tissue, thus providing still further information about the relative spatial positioning of target antigens in the third dimension. Those of ordinary skill in the art will understand the utility of serial section images in the reconstruction of three-dimensional tissue structures.

In some embodiments, a plurality of target antigens are detected on each of the samples. In specific embodiments, at least two target antigens, at least three target antigens, at least five target antigens, at least ten target antigens, at least 15 target antigens, at least 25 target antigens, or even more target antigens are detected on each of the samples. In some embodiments, one or more target antigens are detected on at least three samples, at least four samples, at least five samples, at least ten samples, at least 15 samples, at least 25 samples, or even more.

In another aspect, the instant disclosure provides methods of immunologic assay where a plurality of target antigens in a sample are labeled by an initial treatment with primary antibodies comprising bridging antigens and subsequent sequential treatments with reactive secondary antibodies specific for the bridging antigens. Specifically, a sample comprising a first target antigen and a second target antigen is reacted with a first immunoreagent specific for the first target antigen and a second immunoreagent specific for the second target antigen, wherein the first immunoreagent and the second immunoreagent are any of the above-described immunoreagents. The first immunoreagent is reacted with a first reactive secondary antibody, wherein the first reactive secondary antibody binds to the bridging antigen of the first immunoreagent with high affinity. The location of the first antigen in the sample is then highlighted by reacting the first reactive secondary antibody with a first detectable reagent, wherein the first detectable reagent is thereby bound to the sample in proximity to the first antigen. The first reactive secondary antibody is then selectively dissociated from the sample, and the second immunoreagent is reacted with a second reactive secondary antibody, wherein the second reactive secondary antibody binds to the bridging antigen of the second immunoreagent with high affinity. The location of the second antigen in the sample is then highlighted by reacting the second reactive secondary antibody with a second detectable reagent, wherein the second detectable reagent is thereby bound to the sample in proximity to the second antigen. The first detectable reagent and the second detectable reagent are then detected, thus identifying the locations of the first target antigen and the second target antigen on the sample.

In specific embodiments of these methods, the first reactive secondary antibody and the second reactive secondary antibody each comprise an enzyme activity, more specifically a peroxidase activity such as a horse radish peroxidase activity. In other specific embodiments, either the first detectable reagent or the second detectable reagent comprises a tyramide, or each of the first detectable reagent and the second detectable reagent comprises a tyramide. In still other specific embodiments, either the first detectable reagent or the second detectable reagent comprises a fluorophore or a chromophore, or each of the first detectable reagent and the second detectable reagent comprises a fluorophore or a chromophore.

In preferred embodiments, the first reactive secondary antibody is dissociated from the sample by a selective treatment. Specifically, the selective treatment may dissociate the first reactive secondary antibody from the sample without dissociating the primary antibodies from the sample. More specifically, the selective treatment may comprise treatment with a soluble bridging antigen. Such a treatment may involve the use of relatively high concentrations of the soluble bridging antigen, for example at least 1 μM, at least 10 μM, at least 100 μM, at least 1 mM, at least 10 mM, or even higher concentrations of the soluble bridging antigen, as would be understood by those of ordinary skill in the art.

It should also be understood that in the above methods, the steps of dissociating the reactive secondary antibody from the sample, reacting an additional immunoreagent with an additional target antigen on the sample, reacting an additional reactive secondary antibody with the additional immunoreagent, and reacting the additional reactive secondary antibody with an additional detectable reagent, so that the additional detectable reagent is bound to the sample in proximity to the additional target antigen, may be repeated as many times as necessary in order to detect the locations of as many target antigens on the sample as desired. In some embodiments, the steps are repeated so as to detect the location of at least three target antigens, at least four target antigens, at least five target antigens, at least ten target antigens, or even more target antigens on the sample.

It should also be understood that the order of the steps used in these assay methods may depend on the particular reaction conditions used, and that additional reaction steps may also be necessary to complete the assays in some cases. For example, if a non-selective method is used to dissociate the reactive secondary antibody from the sample (e.g., heat, denaturation, etc.), it may be necessary to include additional reaction steps in the assays. Specifically, if the dissociation conditions also remove primary antibodies from the sample, a further reaction with an additional immunoreagent prior to reaction with an additional reactive secondary antibody and an additional detectable reagent may be included in the process. In other words, the reaction of a new immunoreagent with a new target antigen will be included in the process for each target antigen. In preferred embodiments, however, where the reactive secondary antibodies are dissociated selectively, all of the desired immunoreagents for reaction with all of the desired target antigens may be added in an initial reaction step, and only the reactive secondary antibodies are added in subsequent cycles. Use of selective treatments to dissociate reactive secondary antibodies from the sample minimizes damage to the sample from harsh treatments and therefore improves outcomes from the assays.

The immunoreagents of the instant disclosure may be usefully employed in a variety of immunochemical methods of detection, including without limitation microscopic imaging, pretargeting imaging, and other types of in vivo tumor and tissue imaging, high content screening (HCS), immunocytochemistry (ICC), immunomagnetic cellular depletion, immunomagnetic cell capture, sandwich assays, general affinity assays, enzyme immuno-assay (EIA), enzyme linked immuno-assay (ELISA), ELISpot, mass cytometry (CyTOF), arrays including microsphere arrays, multiplexed microsphere array, microarray, antibody array, cellular array, solution phase capture, lateral flow assays, chemiluminescence detection, infrared detection, blotting methods, including Western blots, Southwestern blot, dot blot, tissue blot, and the like, or combinations thereof. Each of these assays may benefit from the high level of multiplexing achieved using the instant immunoreagents.

The target antigens recognized by the antibodies of the instant immunoreagents may be either polypeptide antigens, such as, for example, cellular proteins of interest or other antibodies, or small-molecule antigens, such as haptens. Other antigens may also be usefully targeted by the instant immunoreagents, as would be understood by those of ordinary skill in the art. For example, targets of the instant immunoreagents include proteins, microorganisms, viruses, bacteria, drugs, hormones, toxins, biomolecules, lipids, carbohydrates, nucleic acids, synthetic molecules, modified proteins, and the like.

The above methods find use in research and clinical settings, without limitation. They may be used for diagnostic purposes, including predictive screening and in other types of prognostic assays, for example in a diagnostic laboratory setting or for point of care testing. The instant multiplexed antibody technology is also well-suited for use in high-throughput screens.

Methods of Preparation

In another aspect, the instant disclosure provides novel methods of preparing antigen-coupled immunoreagents such as the immunoreagents described above. In some embodiments, the methods comprise the step of coupling a primary antibody to a bridging antigen using a chemical coupling reaction. In specific embodiments, the primary antibody and the bridging antigen are coupled by a high-efficiency conjugation moiety. In some embodiments the methods comprise the steps of modifying an antibody with a first conjugating reagent, modifying a bridging antigen with a second conjugating reagent, and reacting the modified antibody with the modified bridging antigen to generate an antigen-coupled immunoreagent. In specific embodiments, the first conjugating reagent and the second conjugating reagent associate with one another at high efficiency.

By high-efficiency, it is meant that the efficiency of conversion of antibody to antigen-coupled antibody is at least 50%, 70%, 90%, 95%, or 99% complete under the conditions of the conjugation reaction. In some embodiments, these efficiencies are achieved at no more than 0.5 mg/mL, no more than 0.2 mg/mL, no more than 0.1 mg/mL, no more than 0.05 mg/mL, no more than 0.02 mg/mL, no more than 0.01 mg/mL, or even lower protein concentrations.

The antibodies and bridging antigens usefully employed in the methods of preparation include any of the antibodies and bridging antigens described above. The first and second conjugating reagents are chosen according to the desired outcomes. In particular, high-efficiency conjugating reagents capable of specific and selective reaction with amino or thiol groups are of particular utility in the modification of peptides and proteins, such as antibodies and peptidic bridging antigens. In addition, the first and second conjugating reagents are chosen for their ability to associate with one another at high efficiency, and thus to create the high-efficiency conjugation moiety in some of the above-described antigen-coupled immunoreagents.

As described above, the resulting conjugation moiety may be a covalent moiety or a non-covalent moiety, and the first and second conjugating reagents used to prepare the modified antibodies and modified bridging antigens are chosen accordingly. For example, in the case of a non-covalent conjugation moiety, the first conjugating reagent preferably comprises a selectively reactive group to attach the reagent to particular reactive residues of the antibody and a first component of the conjugation pair. Likewise, the second conjugating reagent preferably comprises a selectively reactive group to attach the reagent to particular reactive residues of the bridging antigen and a second component of the conjugation pair. The first and second components of the conjugation pairs are able to associate with one another non-covalently at high efficiency and thus to generate the antigen-coupled immunoreagent.

As previously described, examples of non-covalent conjugation moieties include oligonucleotide hybridization pairs and protein-ligand binding pairs. In the case of an oligonucleotide hybridization pair, for example, the antibody would be reacted with a first conjugating reagent that comprises one member of the hybridization pair, and the bridging antigen would be reacted with a second conjugating reagent that comprises the second member of the hybridization pair. The modified antibody and the modified bridging antigen can thus be mixed with one another, and the association of the two members of the hybridization pair generates the high-efficiency conjugation moiety.

Likewise, when a protein-ligand binding pair is used to generate the non-covalent conjugation moiety of the antigen-coupled immunoreagent, the antibody is reacted with a first conjugating reagent that comprises one or the other of the protein-ligand pair, and the bridging antigen is reacted with a second conjugating reagent that comprises the complementary member of the protein-ligand pair. The so-modified antibody and bridging antigen are then mixed with one another to generate the high-efficiency conjugation moiety.

As was described in detail above, examples of high-efficiency covalent conjugation moieties include hydrazones, oximes, other Schiff bases, and the products of any of the various click reactions. Exemplary hydrazino, oxyamino, and carbonyl conjugating reagents for use in forming the high-efficiency conjugation moieties are illustrated in U.S. Pat. No. 7,102,024 and can be adapted for use in the instant reaction methods. As described therein, the hydrazine moiety may be an aliphatic, aromatic, or heteroaromatic hydrazine, semicarbazide, carbazide, hydrazide, thiosemicarbazide, thiocarbazide, carbonic acid dihydrazine, or hydrazine carboxylate. The carbonyl moiety may be any carbonyl-containing group capable of forming a hydrazine or oxime linkage with one or more of the above-described hydrazine or oxyamino moieties. Preferred carbonyl moieties include aldehydes and ketones. Activated versions of some of these reagents, for use as conjugating reagents in the instant methods, are available commercially, for example from Solulink, Inc. (San Diego, CA) and Jena Bioscience GmbH (Jena, Germany). In some embodiments, the reagents may be incorporated into the bridging antigen during the synthesis of the antigen, for example during the synthesis of a peptidic bridging antigen by solid phase synthesis.

The incorporation of hydrazine, oxyamino, and carbonyl-based monomers into oligonucleotides for use in immobilization and other conjugation reactions is described in U.S. Pat. Nos. 6,686,461; 7,173,125; and 7,999,098. Hydrazine-based and carbonyl-based bifunctional crosslinking reagents for use in the conjugation and immobilization of biomolecules is described in U.S. Pat. No. 6,800,728. The use of high-efficiency bisaryl-hydrazone linkers to form oligonucleotide conjugates in various detection assays and other applications is described in PCT International Publication No. WO 2012/071428. Each of the above references is hereby incorporated by reference herein in its entirety.

In some embodiments, the immunoreagents of the instant disclosure are prepared using novel conjugating reagents and conditions. For example a thiol-reactive maleimido oxyamino (MOA) conjugating reagent useful in the preparation of antigen-coupled immunoreagents may be prepared as shown in Scheme 1:

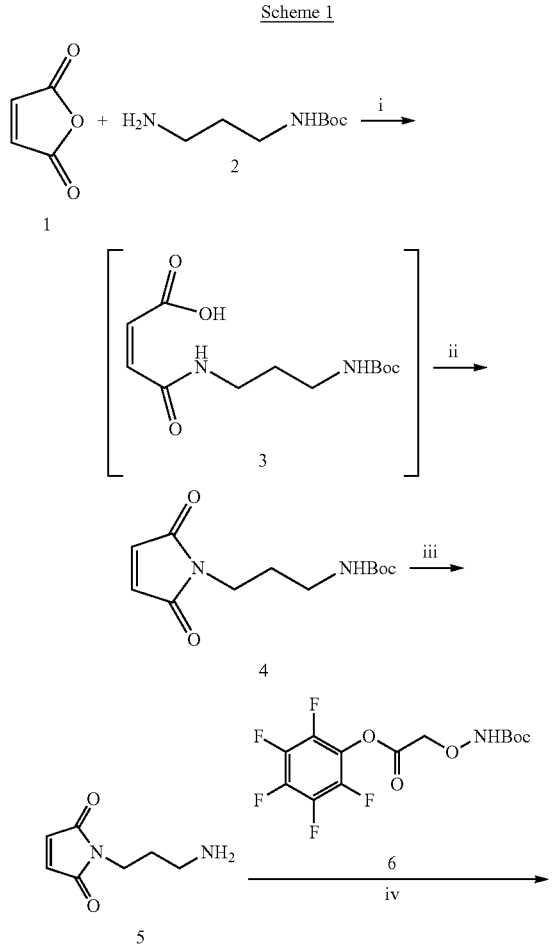

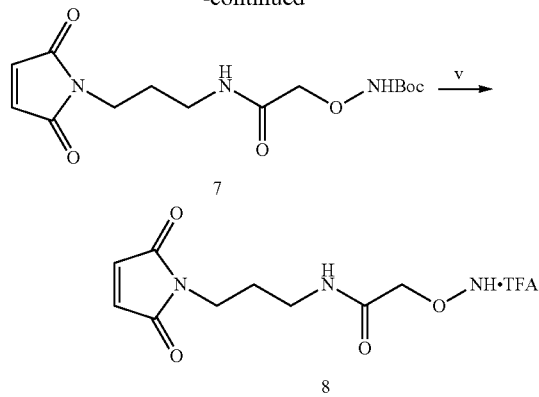

An amino-reactive oxyamino conjugating reagent (AOA) may be prepared as shown in Scheme 2:

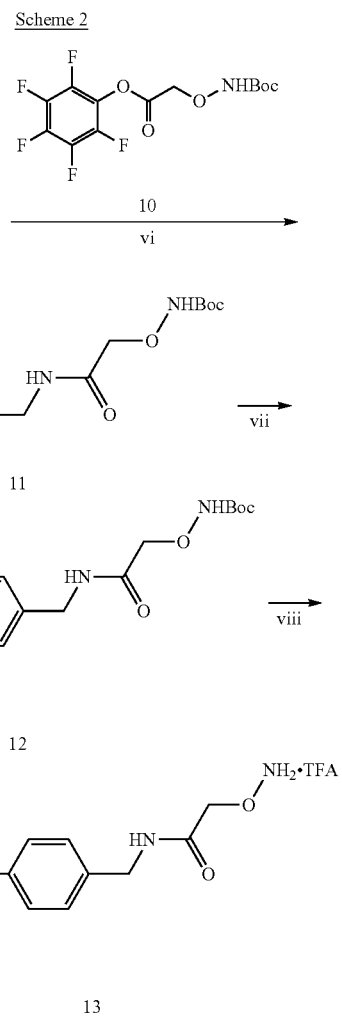

Alternative thiol-reactive and amino-reactive conjugating reagents may be prepared using variants of the above reaction schemes, as would be understood by those of ordinary skill in the art of synthetic chemistry. Such alternative reagents should be considered within the scope of the preparation methods disclosed herein.

Antibodies and bridging antigens modified using one or another of the above oxyamino-containing reagents may usefully be reacted with a complementary antibody or bridging antigen that is itself modified with a carbonyl-containing reagent, for example, an aromatic aldehyde such as a formylbenzoate group. Alternative examples of such a conjugation reactions are shown in Schemes 3 and 4, where the $R_1$ and $R_2$ groups represent independently an antibody or a bridging antigen.

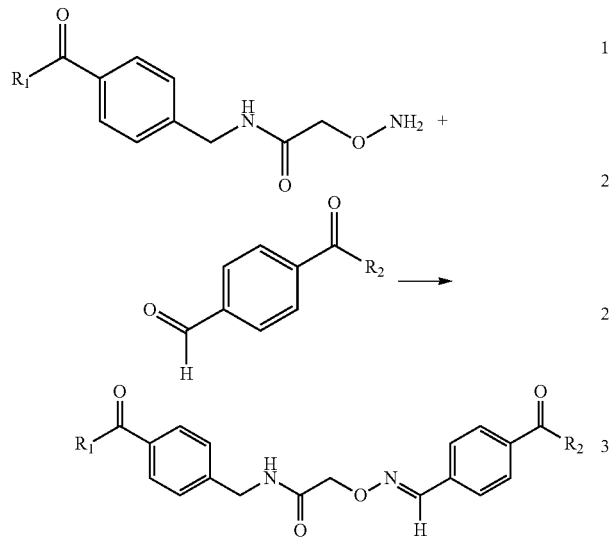

Scheme 3

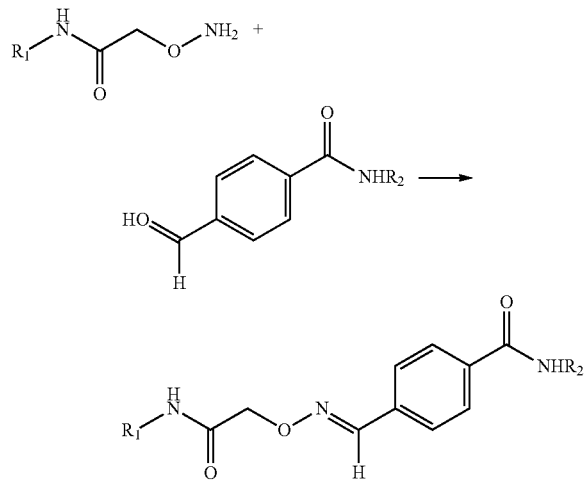

Scheme 4

It should be understood that the relative orientation of the different members of the conjugation moiety-forming groups on the antibody and on the bridging antigen are generally not believed to be important, so long as the groups are able to react with one another to form the high-efficiency conjugation moiety. In other words, in the examples of Schemes 3 and 4, the $R_1$ group could be the antibody and the $R_2$ group could be the bridging antigen, or the $R_1$ group could be the bridging antigen and the $R_2$ group could be the antibody. The same is generally true for all of the above-described conjugating pairs, whether covalent or non-covalent. The peptides shown in Table 1 of the Examples were attached to primary antibodies using the reaction shown in Scheme 4, where the AOA group is attached at the amino terminus of the peptide, the "$R_1$" group corresponds to the peptide, and the "$R_2$" group is the antibody.

The above-described conjugation methods provide several advantages over traditional crosslinking methods, for example methods using bifunctional crosslinking reagents. In particular, the reactions are specific, efficient, and stable. The specificity means that side reactions, such as homoconjugation reactions, do not occur, or occur at extremely low levels. The efficiency means that the reactions run to completion, or near completion, even at low protein concentrations, thus generating products in at or near stoichiometric amounts. The stability of the conjugation moieties formed means that the resultant immunoreagents can be used for a wide variety of purposes without concern that the conjugated products will dissociate during use. In some cases, the above conjugation methods allow the further advantage that the progress of the conjugation reaction may be monitored spectroscopically, since in some of the reactions a chromaphore is formed as the reaction occurs.

The synthesis and stabilities of hydrazone-linked adriamycin/monoclonal antibody conjugates are described in Kaneko et al. (1991) *Bioconj. Chem.* 2:133-41. The synthesis and protein-modifying properties of a series of aromatic hydrazides, hydrazines, and thiosemicarbazides are described in U.S. Pat. Nos. 5,206,370; 5,420,285; and 5,753,520. The generation of conjugationally-extended hydrazine compounds and fluorescent hydrazine compounds is described in U.S. Pat. No. 8,541,555.

Diagnostic Kits

In another aspect, the instant disclosure provides kits for use in immunochemical assays for diagnostic or research purposes. The diagnostic kits comprise one or more immunoreagents of the instant disclosure, together with instructions for use in an immunologic assay. In some embodiments, the kits further comprise a secondary antibody, for example a secondary antibody that is specific for the bridging antigen of the immunoreagent at high affinity. Furthermore, it should be understood that the immunoreagent included in the instant kits will typically comprise an antibody directed at a cellular marker, so that the kit may be used in immunologic assays for the detection of the cellular marker in a tissue sample, in a suspension of cells, on another surface, or in another medium. In some situations, however, it may be useful for the kit to provide an immunoreagent comprising an antibody directed at a cross-species immunoglobulin, for example an anti-mouse antibody, an anti-rabbit antibody, or the like. In these kits, the immunoreagent may be used in immunologic assays for the detection of primary antibodies of the target species.

In further embodiments, the kits may comprise further components such as, for example, buffers of various compositions to enable usage of the kit for staining cells or tissues; and cellular counterstains to enable visualization of sample morphology. Kits may be provided in various formats and include some or all of the above listed components, or may include additional components not listed here.

Alternative Binding Agents

In another aspect of the disclosure, the primary antibody component of the instant immunoreagents may be substituted with another agent capable of binding to target antigens with high affinity. For example, aptamers are single-stranded DNA or RNA oligomers that are capable of forming a variety of tertiary structures and that are capable of binding to targets such as metal ions, small molecules, proteins, viruses, cells, and the like. See Ma et al. (2015) *Chem. Soc. Rev.* (DOI: 10.1039/C4CS00357H). Aptamers with high affinity and high specificity for a given target molecule may be selected from a random library using a procedure known as Sytematic Evolution of Ligands by EXponential enrichment (SELEX), as is understood by those of ordinary skill in the art. Once a suitable aptamer has been identified and characterized, it may be further modified, for example by the attachment of a label or other desired modification. See, e.g., Wang et al. (2011) *Curr. Med. Chem.* 18:4175-4184 for a review of aptamer-based fluorescent biosensors.

The immunoreagents of the instant disclosure may advantageously employ aptamers, or other similar high-affinity and high-selectivity binding agents, by coupling those agents with a bridging antigen, as described above for the immunoreagents prepared from more traditional antibodies. For purposes of this disclosure, it should therefore be understood that aptamers, and other related high-affinity and high-selectivity binding agents, should be considered to fall within the scope of the term "antibody", as used and claimed herein, due to the ability of aptamers to specifically recognize and bind specific target molecules on a sample, as would be understood by those of ordinary skill in the art.

Accordingly, in some embodiments, the immunoreagents of the instant disclosure may comprise:
an aptamer; and
a bridging antigen;
wherein the aptamer and the bridging antigen are coupled; and
wherein the bridging antigen is recognized by a detectable secondary antibody with high affinity. In specific embodiments, the immunoreagents include one or more of the features of the above-described immunoreagents comprising traditional antibodies.

Other Aspects

In other aspects, the disclosure provides the features described in following numbered paragraphs.

1. An immunoreagent composition comprising:
a primary antibody coupled to a bridging antigen; and
a detectable secondary antibody;
wherein the detectable secondary antibody is specific for the bridging antigen with high affinity.
2. The immunoreagent composition of paragraph 1, wherein the bridging antigen is a peptide or a small-molecule hapten.
3. The immunoreagent composition of paragraph 1, wherein the primary antibody and the bridging antigen are coupled by a chemical coupling reaction.
4. The immunoreagent composition of paragraph 1, wherein the primary antibody and the bridging antigen are coupled by a high-efficiency conjugation moiety.
5. The immunoreagent composition of paragraph 4, wherein the high-efficiency conjugation moiety is a Schiff base.
6. The immunoreagent composition of paragraph 5, wherein the Schiff base is a hydrazone or an oxime.
7. The immunoreagent composition of paragraph 4, wherein the high-efficiency conjugation moiety is formed by a click reaction.
8. The immunoreagent composition of paragraph 1, wherein the primary antibody is specific for a cellular marker.
9. The immunoreagent composition of paragraph 8, wherein the cellular marker is selected from the group consisting of: ER, HER2, PR, Ki67, EGFR, CK1, CK5, CK6, CK7, CK14, CK17, cytokeratin AE1/AE3, nestin, vimentin, ASMA, Ber-EP4, p16, p40, p53, p63, c-kit, and a CD marker.
10. The immunoreagent composition of paragraph 1, wherein the primary antibody is specific for an immunoglobulin from a different species.
11. The immunoreagent composition of paragraph 1, wherein the detectable secondary antibody comprises a detectable label.
12. The immunoreagent composition of paragraph 11, wherein the detectable label is a fluorophore, an enzyme, an upconverting nanoparticle, a quantum dot, or a detectable hapten.
13. The immunoreagent composition of paragraph 12, wherein the detectable label is a fluorophore.
14. The immunoreagent composition of paragraph 12, wherein the enzyme is a peroxidase, an alkaline phosphatase, or a glucose oxidase.
15. The immunoreagent composition of paragraph 14, wherein the peroxidase is a horseradish peroxidase or a soybean peroxidase.
16. The immunoreagent composition of paragraph 1, wherein the detectable secondary antibody is specific for the bridging antigen with a dissociation constant of at most 100 nM, at most 30 nM, at most 10 nM, at most 3 nM, at most 1 nM, at most 0.3 nM, at most 0.1 nM, at most 0.03 nM, at most 0.01 nM, or at most 0.003 nM.
17. An immunoreagent composition comprising:
a plurality of primary antibodies coupled to a plurality of bridging antigens; and
a plurality of detectable secondary antibodies;
wherein each bridging antigen is coupled to a different primary antibody; and
wherein at least one detectable secondary antibody is specific for at least one bridging antigen with high affinity.
18. The immunoreagent composition of paragraph 17, wherein each bridging antigen is a peptide or a small-molecule hapten.
19. The immunoreagent composition of paragraph 17, wherein the plurality of primary antibodies and the plurality of bridging antigens are coupled by chemical coupling reactions.
20. The immunoreagent composition of paragraph 17, wherein the plurality of primary antibodies and the plurality of bridging antigens are coupled by high-efficiency conjugation moieties.
21. The immunoreagent composition of paragraph 20, wherein the high-efficiency conjugation moieties are Schiff bases.
22. The immunoreagent composition of paragraph 21, wherein the Schiff bases are hydrazones or oximes.
23. The immunoreagent composition of paragraph 20, wherein the high-efficiency conjugation moieties are formed by click reactions.
24. The immunoreagent composition of paragraph 17, wherein the plurality of primary antibodies are specific for a plurality of cellular markers.
25. The immunoreagent composition of paragraph 24, wherein the cellular markers are selected from the group consisting of: ER, HER2, PR, Ki67, EGFR, CK1, CK5, CK6, CK7, CK14, CK17, cytokeratin AE1/AE3, nestin, vimentin, ASMA, Ber-EP4, p16, p40, p53, p63, c-kit, and a CD marker.
26. The immunoreagent composition of paragraph 17, wherein the plurality of primary antibodies are specific for a plurality of immunoglobulins from different species.
27. The immunoreagent composition of paragraph 17, wherein the plurality of detectable secondary antibodies comprise detectable labels.

28. The immunoreagent composition of paragraph 27, wherein the detectable labels are fluorophores, enzymes, upconverting nanoparticles, quantum dots, or detectable haptens.

29. The immunoreagent composition of paragraph 28, wherein the detectable labels are fluorophores.

30. The immunoreagent composition of paragraph 28, wherein the enzymes are peroxidases, alkaline phosphatases, or glucose oxidases.

31. The immunoreagent composition of paragraph 30, wherein the peroxidases are horseradish peroxidases or soybean peroxidases.

32. The immunoreagent composition of paragraph 17, wherein the at least one detectable secondary antibody is specific for the at least one bridging antigen with a dissociation constant of at most 100 nM, at most 30 nM, at most 10 nM, at most 3 nM, at most 1 nM, at most 0.3 nM, at most 0.1 nM, at most 0.03 nM, at most 0.01 nM, or at most 0.003 nM.

33. The immunoreagent composition of paragraph 17, wherein each detectable secondary antibody is specific for each bridging antigen with high affinity.

34. The immunoreagent composition of paragraph 17, wherein the composition comprises at least three different bridging antigens.

35. The immunoreagent composition of paragraph 34, wherein the composition comprises at least five different bridging antigens.

36. The immunoreagent composition of paragraph 35, wherein the composition comprises at least ten different bridging antigens.

37. An immunoreagent comprising:
    a primary antibody; and
    a bridging antigen;
    wherein the primary antibody and the bridging antigen are coupled; and
    wherein the bridging antigen is recognized by a detectable secondary antibody with high affinity.

38. The immunoreagent of paragraph 37, wherein the bridging antigen is a peptide.

39. The immunoreagent of paragraph 37, wherein the primary antibody and the bridging antigen are coupled by a chemical coupling reaction.

40. The immunoreagent of paragraph 37, wherein the primary antibody and the bridging antigen are coupled by a high-efficiency conjugation moiety.

41. The immunoreagent of paragraph 40, wherein the high-efficiency conjugation moiety is a Schiff base.

42. The immunoreagent of paragraph 41, wherein the Schiff base is a hydrazone or an oxime.

43. The immunoreagent of paragraph 40, wherein the high-efficiency conjugation moiety is formed by a click reaction.

44. The immunoreagent of paragraph 37, wherein the primary antibody is specific for a cellular marker.

45. The immunoreagent of paragraph 44, wherein the cellular marker is selected from the group consisting of: ER, HER2, PR, Ki67, EGFR, CK1, CK5, CK6, CK7, CK14, CK17, cytokeratin AE1/AE3, nestin, vimentin, ASMA, Ber-EP4, p16, p40, p53, p63, c-kit, and a CD marker.

46. The immunoreagent of paragraph 37, wherein the primary antibody is specific for an immunoglobulin from a different species.

47. The immunoreagent of paragraph 37, wherein the bridging antigen is recognized by the detectable secondary antibody with a dissociation constant of at most 100 nM, at most 30 nM, at most 10 nM, at most 3 nM, at most 1 nM, at most 0.3 nM, at most 0.1 nM, at most 0.03 nM, at most 0.01 nM, or at most 0.003 nM.

48. An immunoreagent composition comprising:
    at least three immunoreagents of any one of paragraphs 37-47.

49. The immunoreagent composition of paragraph 48, comprising at least five immunoreagents of any one of paragraphs 37-47.

50. The immunoreagent composition of paragraph 48, comprising at least ten immunoreagents of any one of paragraphs 37-47.

51. The immunoreagent composition of paragraph 48, wherein the primary antibodies are specific for a plurality of cellular markers.

52. The immunoreagent composition of paragraph 51, wherein the cellular markers are selected from the group consisting of: ER, HER2, PR, Ki67, EGFR, CK1, CK5, CK6, CK7, CK14, CK17, cytokeratin AE1/AE3, nestin, vimentin, ASMA, Ber-EP4, p16, p40, p53, p63, c-kit, and a CD marker.

53. The immunoreagent composition of paragraph 48, wherein the bridging antigens are peptides.

54. A method for immunologic assay comprising:
    providing a sample comprising a first target antigen;
    reacting a first immunoreagent with the first target antigen, wherein the first immunoreagent is the immunoreagent of any one of paragraphs 37-47 specific for the first target antigen;
    reacting a first detectable secondary antibody with the first immunoreagent, wherein the first detectable secondary antibody is specific for the bridging antigen of the first immunoreagent with high affinity; and
    detecting the first detectable secondary antibody that is associated with the bridging antigen of the first immunoreagent.

55. The method of paragraph 54, wherein the first target antigen is a cellular marker.

56. The method of paragraph 55, wherein the cellular marker is selected from the group consisting of: ER, HER2, PR, Ki67, EGFR, CK1, CK5, CK6, CK7, CK14, CK17, cytokeratin AE1/AE3, nestin, vimentin, ASMA, Ber-EP4, p16, p40, p53, p63, c-kit, and a CD marker.

57. The method of paragraph 54, wherein the first target antigen is an immunoglobulin from a different species.

58. The method of paragraph 54, wherein the first detectable secondary antibody comprises a detectable label.

59. The method of paragraph 58, wherein the detectable label is a fluorophore, an enzyme, an upconverting nanoparticle, a quantum dot, or a detectable hapten.

60. The method of paragraph 59, wherein the detectable label is a fluorophore.

61. The method of paragraph 59, wherein the enzyme is a peroxidase, an alkaline phosphatase, or a glucose oxidase.

62. The method of paragraph 61, wherein the peroxidase is a horseradish peroxidase or a soybean peroxidase.

63. The method of paragraph 54, wherein the first detectable secondary antibody is specific for the bridging antigen of the first immunoreagent with a dissociation constant of at most 100 nM, at most 30 nM, at most 10 nM, at most 3 nM, at most 1 nM, at most 0.3 nM, at most 0.1 nM, at most 0.03 nM, at most 0.01 nM, or at most 0.003 nM.

64. The method of paragraph 54, wherein the first target antigen is within a tissue section.

65. The method of paragraph 64, wherein the detecting step is a fluorescence detection step.

66. The method of paragraph 64, wherein the detecting step is an enzymatic detection step.
67. The method of paragraph 54, wherein the first target antigen is in or on a cell.
68. The method of paragraph 67, wherein the first target antigen is on the surface of the cell.
69. The method of paragraph 67, wherein the first target antigen is in the cytoplasm of the cell.
70. The method of paragraph 67, wherein the first target antigen is in the nucleus of the cell.
71. The method of paragraph 67, wherein the detecting step is a fluorescence detection step.
72. The method of paragraph 71, further comprising the step of sorting cells that have bound the first detectable secondary antibody.
73. The method of paragraph 54, further comprising
    reacting a second immunoreagent with a second target antigen in the sample, wherein the second immunoreagent is the immunoreagent of any one of paragraphs 37-47 specific for the second antigen;
    reacting a second detectable secondary antibody with the second immunoreagent, wherein the second detectable secondary antibody is specific for the bridging antigen of the second immunoreagent with high affinity; and
    detecting the second detectable secondary antibody that is associated with the bridging antigen of the second immunoreagent.
74. The method of paragraph 73, further comprising detecting at least three target antigens in the sample.
75. The method of paragraph 74, further comprising detecting at least five target antigens in the sample.
76. The method of paragraph 75, further comprising detecting at least ten target antigens in the sample.
77. A method for immunologic assay comprising:
    providing a sample comprising a first target antigen;
    reacting a first primary antibody with the first target antigen, wherein the first primary antibody is specific for the first target antigen;
    reacting a first immunoreagent with the first primary antibody, wherein the first immunoreagent is the immunoreagent of any one of paragraphs 37-47 specific for the first primary antibody;
    reacting a first detectable secondary antibody with the first immunoreagent, wherein the first detectable secondary antibody is specific for the bridging antigen of the first immunoreagent with high affinity; and
    detecting the first detectable secondary antibody that is associated with the bridging antigen of the first immunoreagent.
78. A kit for immunologic assay comprising:
    the immunoreagent of any one of paragraphs 37-47;
    a detectable secondary antibody specific for the bridging antigen with high affinity; and
    instructions for using the kit.
79. The kit of paragraph 78, wherein the detectable secondary antibody comprises a detectable label.
80. The kit of paragraph 79, wherein the detectable label is a fluorophore, an enzyme, an upconverting nanoparticle, a quantum dot, or a detectable hapten.
81. The kit of paragraph 80, wherein the detectable label is a fluorophore.
82. The kit of paragraph 81, wherein the enzyme is a peroxidase, an alkaline phosphatase, or a glucose oxidase.
83. The kit of paragraph 82, wherein the peroxidase is a horseradish peroxidase or a soybean peroxidase.
84. The kit of paragraph 78, wherein the detectable secondary antibody is specific for the bridging antigen with a dissociation constant of at most 100 nM, at most 30 nM, at most 10 nM, at most 3 nM, at most 1 nM, at most 0.3 nM, at most 0.1 nM, at most 0.03 nM, at most 0.01 nM, or at most 0.003 nM.
85. The kit of paragraph 78, comprising:
    at least three immunoreagents of any one of paragraphs 37-47;
    at least three detectable secondary antibodies specific for the bridging antigens with high affinity; and
    instructions for using the kit.
86. The kit of paragraph 78, comprising:
    at least five immunoreagents of any one of paragraphs 37-47;
    at least five detectable secondary antibodies specific for the bridging antigens with high affinity; and
    instructions for using the kit.
87. The kit of paragraph 78, comprising:
    at least ten immunoreagents of any one of paragraphs 37-47;
    at least ten detectable secondary antibodies specific for the bridging antigens with high affinity; and
    instructions for using the kit.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

Examples

Multiplex Labeling of Tissue Sections with Peptide-Labeled Primary Antibodies and Fluorescent Anti-Peptide Secondary Antibodies Materials and Methods Modification Buffer (100 mM phosphate, 150 mM NaCl, pH 7.4-7.6), Conjugation Buffer (100 mM phosphate, 150 mM NaCl, pH 6.0), Aniline Buffer (100 mM, phosphate, 150 mM NaCl, 100 mM aniline, pH 6.0), PBS (10 mM phosphate, 150 mM NaCl, pH 7.0). Zeba desalting columns from ThermoPierce (Rockford, IL).

Amino reactive fluorescent dyes Dy488-OSu, Dy550-OSu and Dy650-OSu were purchased from Dyomics, Inc, Jena, Germany.

Antibodies

Goat anti-mouse and goat anti-rabbit antibodies were purchased from ImmunoReagents, Inc. (Raleigh, NC). Rabbit monoclonal anti-estrogen receptor (ER), anti-progesterone receptor (PR) and anti-HER2/neu receptor (HER2) antibodies were purchased from Epitomics, Inc. (Fremont, CA). Mouse anti-Ki67 was purchased from BD Biosciences, San Diego, CA Rabbit monoclonal anti-peptide antibodies against PEP1, PEP2, PEP3, PEP4, and PEP5 were obtained from AvantGen, Inc. (San Diego, CA).

Fluorescence Staining and Imaging

The following protocols were employed in the below-described immunofluorescence staining experiments. The slides were imaged on a Vala Sciences IC200Hist Imager (Vala Sciences, San Diego, CA). The images were processed using open source ImageJ software and quantified using CyteSeer software (Vala Sciences, San Diego, CA).

Unless otherwise indicated all breast cancer tissue was purchased from Key Biomedical, Ojai, CA Manual Staining Protocol:
1. Slides were dewaxed as follows:

| | |
|---|---|
| Xylene | 5 min |
| Xylene | 5 min |
| 100% Ethanol | 2 min |
| 100% Ethanol | 2 min |
| 95% Ethanol | 2 min |

2. Wash 2× with tap water 2 min each.
3. Wash 1× with distilled water 2 min.
4. Antigen retrieval was accomplished by steaming in 10 mM citric acid pH 6.0 for 15 min.
5. Slides were cooled in pressure cooker for 10 min before releasing pressure.
6. Pressure was released and slides were moved to hot distilled water for 2 min.
7. Slides were washed under running tap water for 5 min.
8. Slides were rinsed in wash buffer for 5 mins.
9. Circles were drawn around the tissue using a hydrophobic pen.
10. Slides were blocked with normal serum (3% goat or rabbit serum, sometimes other serum depending on stain) for 20 min.
11. After removal of previous solution, 150 uL to 200 uL of bridging antigen-labeled primary antibody were added directly onto slide, which can be diluted using antibody diluent, and incubated for 1 hr at room temperature.
12. Slides were washed 3× with wash buffer for 5 min each.
13. To the slide was added the fluorescently-labeled anti-bridging antigen antibody at the desired concentration and incubated at room temperature for 1 h.
14. Slides were washed 3× in wash buffer for 5 min each.
15. Slides were rinsed with distilled water, removing excess water with paper towel.
16. 1-3 drops of Fluoroshield with DAPI (Immunobiosciences, Inc, cat#AR-6501-01) was added to each slide and after 3-5 min in the dark at room temperature the coverslip was applied.

Triplex Staining Protocol Modification:
Alternative step 11. To the slide was added a cocktail of peptide-labeled primary antibodies at optimized concentrations and incubated at room temperature for one hour. In a specific example a cocktail of anti-ER-PEP7 (10 ug/mL) and anti-HER2-PEP5 (5 ug/mL) and anti-Ki67-PEP1 (5 ug/mL) was added to triple positive breast cancer tissue and incubated at room temperature for 1 h.

Alternative step 13. A cocktail of fluorophore-labeled anti-bridging antigen antibodies of desired concentrations was prepared and added to the slide and incubated at room temperature for 1 h. In a specific example a cocktail of anti-PEP7-Dy550, anti-PEP5-Dy490 and anti-PEP1-Dy755 (all at 5 ug/mL) was added and incubated at room temperature for 1 h. The results are presented in FIG. 6.

Pentafluorophenyl Boc-Aminooxyacetate Synthesis

To a solution of Boc-aminooxyacetic acid (5.0 g, 26.2 mmol; EMD Chemicals) in DMF (30 mL) was added pentafluorophenyl (4.57 g, 24.8 mmol; Oakwood Chemicals) and EDC (5.51 g, 2.88 mmol; Oakwood Chemicals). The reaction mixture was stirred at room temperature for 16 h. The DMF was removed on the rotavap and the residue was partitioned between ethyl acetate and saturated sodium bicarbonate. The bicarbonate solution was back extracted with ethyl acetate and the combined organic extracts were washed with brine, dried over anhydrous magnesium sulfate, filtered and concentrated to give 3.2 g of a white solid-single spot by TLC (100% ethyl acetate).

Incorporation of AOA Conjugation Reagent on Peptide:

The AOA linker was incorporated on the N-terminus of the peptide using standard solid-phase peptide synthesis with pentafluorophenyl Boc-aminooxyacetate, except that following FMOC deprotection of the final amino acid, the resin was washed repeatedly with acetonitrile and treated with a solution of pentafluorophenyl Boc-aminooxyacetate in DMF without base, i.e. diisopropylethylamine. All AOA peptides were purified by reverse phase HPLC, and all peptides were shown to have the expected masses.

Antibody-Peptide Conjugation Protocol

To the deprotected N-terminus of the peptides during their respective solid phase peptide syntheses was added a solution of pentafluorophenyl Boc-aminooxyacetate (7.5 mol equiv) in DMF and incubated for 2 h. No base was added to the linker solution. Following incubation and washing the peptide was cleaved from the resin in the presence of TFA (95%)/water (2.5%/triisopropylsilane (2.5%), lyophilized and purified by reverse phase HPLC.

The following protocol was used to conjugate AOA-modified PEP5 to the anti-HER2 primary antibody. Similar protocols were used to conjugate the other peptides to their respective antibodies. To a solution of anti-HER2 (80 uL; 80 ug at 1.0 mg/mL; 0.5 nmol) in Modification Buffer was added a solution of Sulfo-4-formylbenzamide (0.45 uL of a 2.0 mg/mL solution in DMSO; 12.8 nmol; 24 mol equiv; Cell_IDx, Inc. (San Diego, CA)). The reaction was incubated at room temperature for 2 h and desalted into Conjugation Buffer using a 0.5 mL Zeba column pre-equilibrated with Conjugation Buffer. The antibody recovery was assumed to be 90% (72 ug) based on previous Zeba column recovery rates. AOA-modified PEP5 (0.43 uL of a 5 mg/mL solution in DMSO; 1.2 nmol: 5 mol equiv; InnoPep, Inc. (San Diego, CA)) was added to HER2-4FB, followed by addition of aniline buffer (7 uL) and incubated at room temperature for 2 hours. Free peptide and aniline was removed by using a Spin-X UF 30K molecular weight cutoff concentrator (Corning, UK) by adding 3 separate additions of 10 mM phosphate, 150 mM NaCl, pH 7.0 buffer, of at least 5 fold the amount of sample volume in the concentrator to ensure complete removal and buffer exchange. The concentration of the antibody-peptide product was determined spectrophotometrically using antibody extinction coefficient of 1.4.

Table 1 displays the peptide name and amino acid sequence of the peptides that were covalently attached to the primary antibodies in this example. The "AOA" group (aminooxyacetamide) was used to attach the peptide to the 4FB-modified primary antibody. Also shown in Table 1 are the dissociation constants ($K_D$) between peptide and its corresponding antibody. These values were obtained using a ForteBio instrument (www.fortebio.com).

TABLE 1

| Peptide Name | Peptide Sequence | KD (pM) |
|---|---|---|
| PEP1 | AOA-LALQAQPVPDELVTK (SEQ ID NO: 1) | 90 |
| PEP2 | AOA-DITSDTSGDFR (SEQ ID NO: 2) | 160 |

TABLE 1-continued

| Peptide Name | Peptide Sequence | KD (pM) |
|---|---|---|
| PEP3 | AOA-DATNVGDEGGFAPNILENK (SEQ ID NO: 3) | 90 |
| PEP4 | AOA-GLEPGQEYNVLLTAEK (SEQ ID NO: 4) | 90 |
| PEP5 | AOA-RPHFPQF-pY-SASGTA (SEQ ID NO: 5) (pY = phosphotyrosine) | 40 |
| PEP6 | AOA-ETSGLQEQRNHLQGK-NH2 (SEQ ID NO: 6) | 20 |
| PEP7 | AOA-GAPGKKRDMSSDLERD (SEQ ID NO: 7) | Not determined |

Modification of Anti-Peptide Secondary Antibodies with Fluorophores:

High affinity anti-peptide secondary antibodies were modified with fluorophores as follows: To a solution of anti-peptide antibody in Modification Buffer (0.030 mg; 12 uL of a 2.5 mg/mL solution) was added Dy488-NHS ester (0.5 uL of a 5.0 mg/mL solution in anhydrous DMSO; 12 mol equivalents). The reaction mixture was incubated at room temperature for 2 hours and desalted twice using 0.5 mL 40 K MWCO Zeba columns pre-equilibrated with PBS.

Table 2 presents the bridging antigen-coupled primary antibodies and their target antigens, as well as the complementary fluorescently-labeled high-affinity secondary antibody pairs that were prepared in this example, and the results of their staining on triple positive breast cancer tissue.

TABLE 2

| Peptide | Target Antigen | Dy488 | Dy550 | Dy650 | Dy755 |
|---|---|---|---|---|---|
| PEP1 | HER2 | + | + | + | |
| PEP1 | Ki-67 | | + | + | |
| PEP1 | CK5 | + | | | |
| PEP2 | Ki-67 | | | + | |
| PEP3 | Ki-67 | | | + | + |
| PEP4 | Ki-67 | | | + | |
| PEP5 | ER | | | + | |
| PEP5 | Ki-67 | + | | + | + |

Results

Figure 1B:
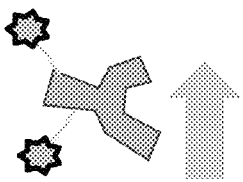
Figure 1C:
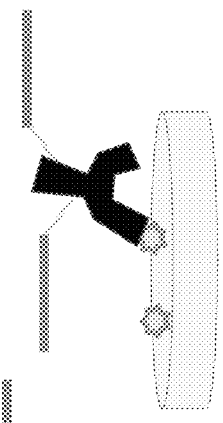

A schematic illustration of the staining of a target antigen with an exemplary immunoreagent of the instant disclosure is shown in FIG. 1A-FIG. 1C. In this drawing, the target antigen, which is represented as two stars outlined in gray on the surface of a sample of interest (A), is labeled with a primary antibody specific for the target antigen (B). As shown in this illustration, the primary antibody was coupled with two bridging antigens (represented by straight lines in the drawing), but it should be understood that higher levels of coupling of bridging antigen to primary antibody could be achieved, if desired. A detectable secondary antibody with high specificity and high affinity for the bridging antigen is then used to stain the sample (C), where the detectable labels are illustrated as stars with dark outlines.

Figure 2B:
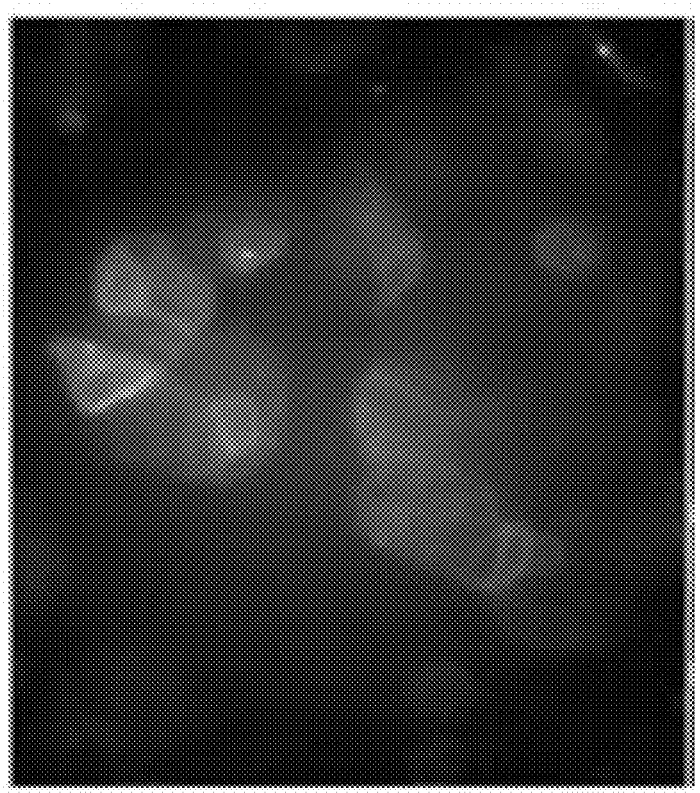
FIG. 2A-FIG. 2B: Immunocytochemical staining of MCF7 cells with a conventional cross-species secondary antibody and with a low-affinity commercial antibody specific for a FLAG tagged primary antibody. Cells were labeled either with an unlabeled human anti-HER2/neu receptor primary antibody (A) or with a FLAG tag-labeled human anti-HER2/neu receptor primary antibody (B). The cells were then stained with a commercial anti-human-Dy488 secondary antibody (A) or with a commercial anti-FLAG-Dy490 secondary antibody (B).
Figure 2A:
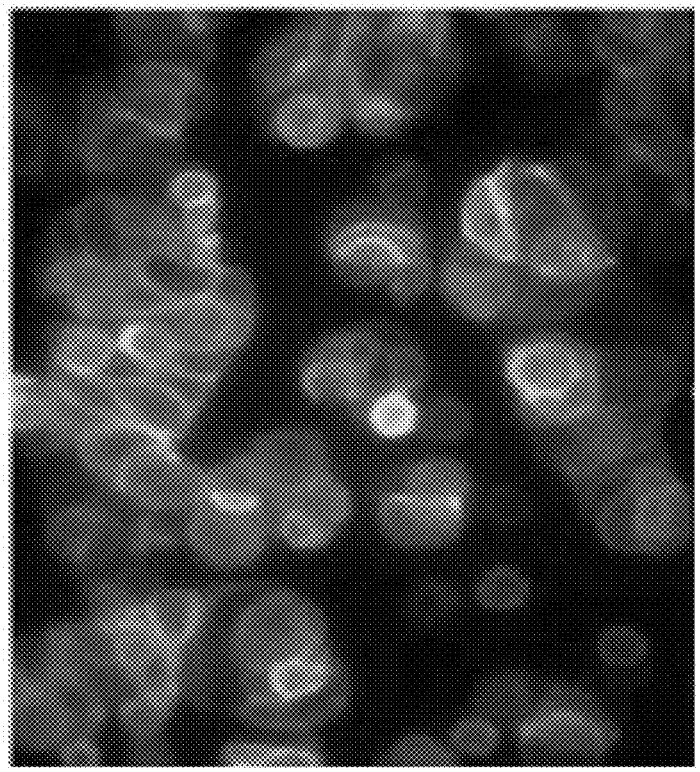

FIG. 2A and FIG. 2B illustrate the poor staining of a peptide-labeled primary antibody using a commercial, low-affinity mouse monoclonal anti-peptide antibody. Specifically, MCF7 cells were subjected to immunocytochemical staining using either a Herceptin antibody (A) or a FLAG tag-labeled Herceptin antibody prepared by the modification of a Herceptin antibody with Sulfo-S-4FB followed by the addition of HyNic-Peg2-Flag-tag (Solulink, Inc., San Diego, CA) in the presence of aniline catalysis (B). The cells were then stained with either a standard fluorescent goat anti-human secondary antibody (A) or a fluorescent anti-FLAG secondary antibody prepared as described above for the fluorophore labeling of anti-peptide antibodies (B). Cells stained with the commercially-available, low-affinity anti-FLAG antibody show significantly lower signal compared to the traditional staining with the labeled cross-species secondary antibody.

Figure 3B:
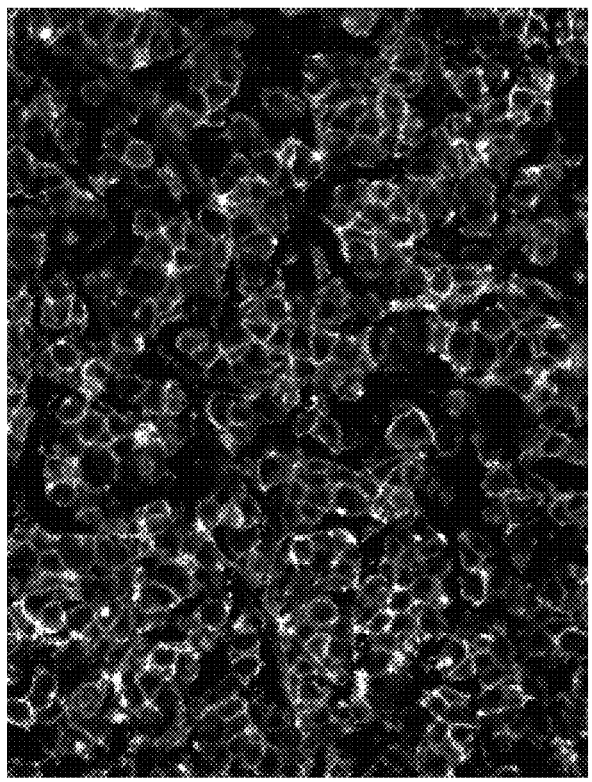
FIG. 3A-FIG. 3B: Immunohistochemical staining of triple-positive human breast cancer cells with a cross-species secondary antibody or with a high-affinity antibody specific for a bridging antigen. Cells were labeled either with an unlabeled rabbit anti-HER2/neu receptor primary antibody (A) or with a peptide-coupled rabbit anti-HER2/neu receptor primary antibody (B). The cells were then stained with a standard fluorescent anti-rabbit secondary antibody (A) or with a fluorescent high-affinity anti-peptide antibody (B).
Figure 3A:
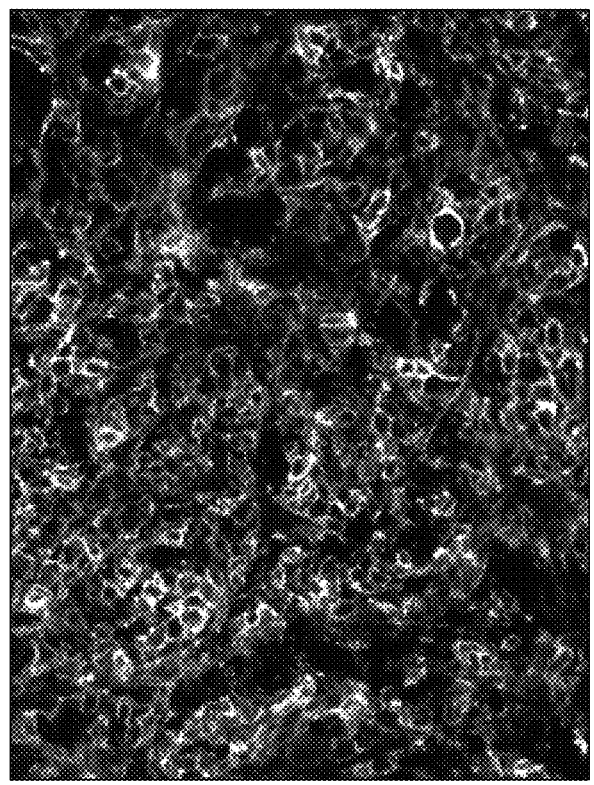
Figure 4A:
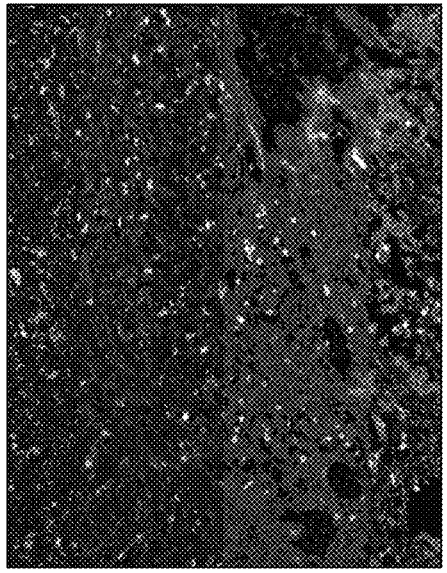
FIG. 4A-FIG. 4D: Comparison of four peptide-coupled primary antibody/fluorophore-labeled anti-peptide secondary antibody pairs. For each of the pairs, an anti-Ki67 primary antibody was conjugated to the subject peptide. Fluorophore-labeled secondary antibodies specific for the subject peptide were applied to visualize the Ki67-positive signal: (A) PEP2, (B) PEP3, (C) PEP4, and (D) PEP5.
Figure 4B:
Figure 4C:
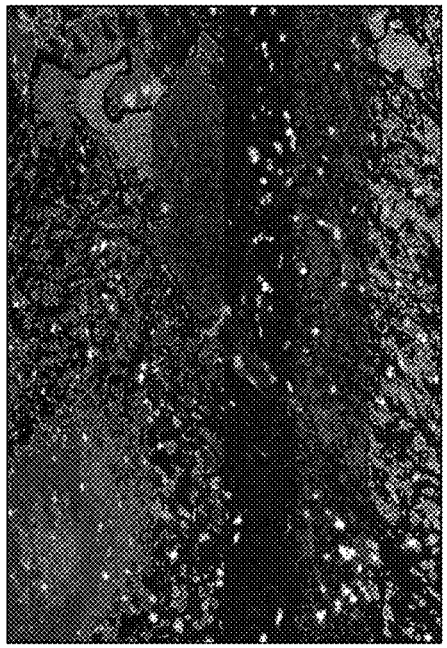
Figure 4D:

The use of a high-affinity anti-peptide antibody to stain a peptide-coupled primary antibody is illustrated in FIG. 3A and FIG. 3B. In this experiment, tissue sections from HER2-positive breast tissue (Key Biomedical, Inc., Ojai, CA) were labeled either with an unlabeled rabbit anti-HER2/neu receptor primary antibody (A) or with a peptide-coupled rabbit anti-HER2/neu receptor primary antibody (B). The samples were then stained either with a Dy488-labeled goat anti-rabbit secondary antibody (A) or with a Dy490-labeled rabbit anti-PEP5 antibody having high affinity for the PEP5 sequence (B). The results show comparable staining for the traditional secondary antibody approach (A) and for the secondary staining with the high-affinity antibody specific for the bridging antigen (B).

The correlation between the staining intensity and affinity of the antibody used to recognize the bridging antigen was demonstrated as shown in FIGS. 4A-4D. Sections of Ki67-positive tissue were first labeled with various peptide-coupled anti-Ki67 primary antibodies. The sections were then stained with fluorophore-labeled secondary antibodies specific for the various coupled peptides but with different affinities. The results show that samples labeled with the highest-affinity peptide-antibody pair (PEP5/anti-PEP5; $K_D$=40 pM) (D) displayed the brightest fluorescence intensity, whereas the peptide-antibody pairs (PEP3/anti-PEP3 and PEP4/anti-PEP4; $K_D$=90 pM) (B) and (C) with intermediate affinity displayed an intermediate fluorescence, and the peptide-antibody pair (PEP2/anti-PEP2; $K_D$=160 pM) (A) with the lowest affinity, had a somewhat lower fluorescence intensity.

Figure 5B:
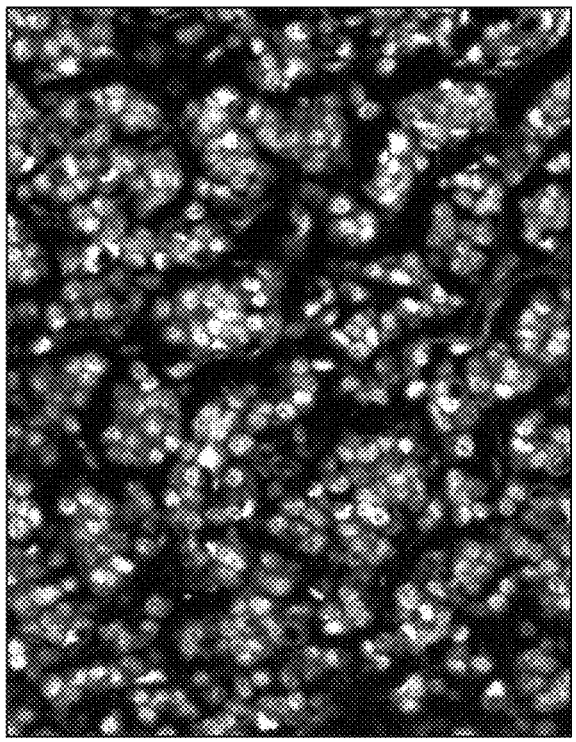
FIG. 5A-FIG. 5B: Comparison of intensity of staining of the estrogen receptor with PEP1 and PEP5 pairs. Anti-ER primary antibodies were coupled with either PEP1 (A) or PEP5 (B) and stained with the corresponding high-affinity anti-peptide antibodies labeled with a fluorophore.
Figure 5A:
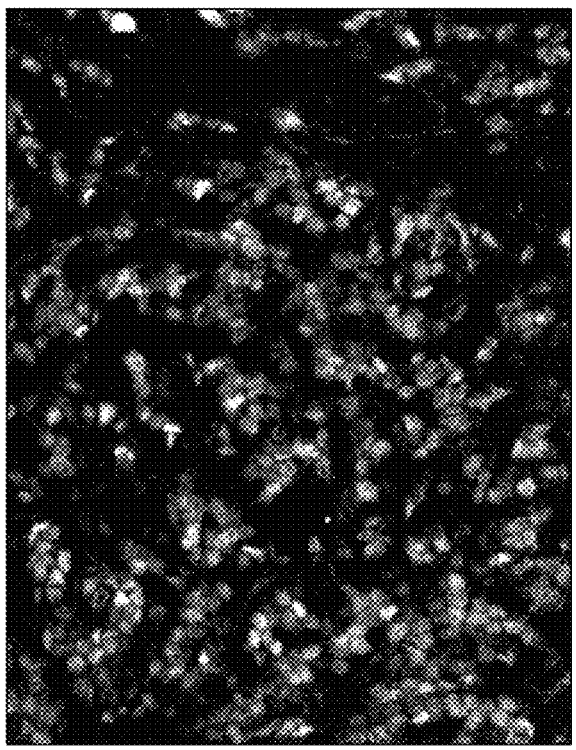

In another comparison of two different peptide/anti-peptide antibody pairs, FIG. 5A and FIG. 5B. show the labeling of ER-positive tissue sections with an anti-ER primary antibody coupled either with PEP1 (A) or PEP5 (B). Samples were subsequently stained with a high-affinity anti-PEP1 antibody (A) or a high-affinity anti-PEP5 antibody (B), each of which was labeled with Dy650.

Figure 6C:
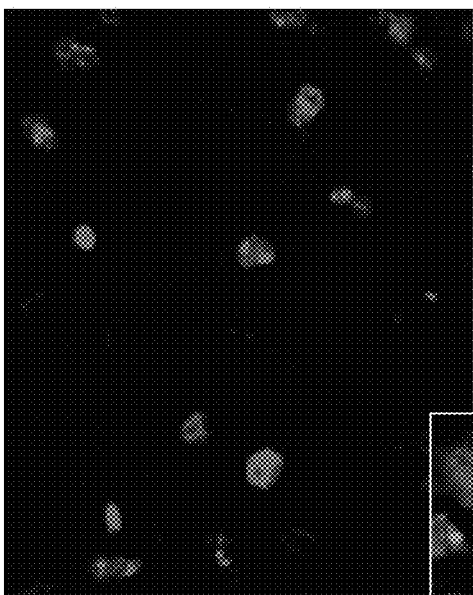
FIG. 6A-FIG. 6D: Multiplexed staining of breast cancer tissue with three different pairs of peptide-coupled primary antibodies and high-affinity fluorescent anti-peptide secondary antibodies: PEP7-coupled anti-ER primary/Dy550-labeled anti-PEP7 secondary; PEP5-coupled anti-HER2 primary/Dy490-labeled anti-PEP5 secondary; and PEP1-coupled anti-Ki67 primary/Dy755-labeled anti-PEP1 secondary. (A) Dy550 emission; (B) Dy490 emission; (C) Dy755 emission; and (D) three-image overlay.
Figure 6B:
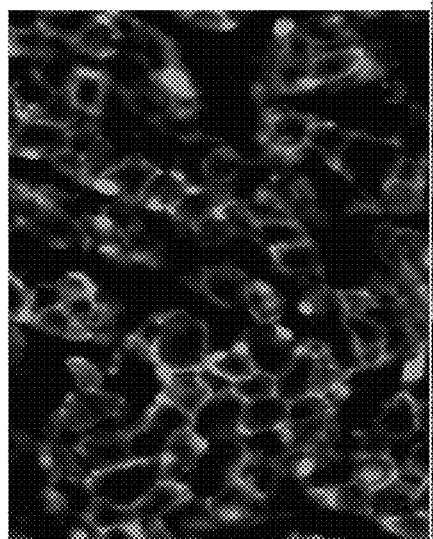
Figure 6A:
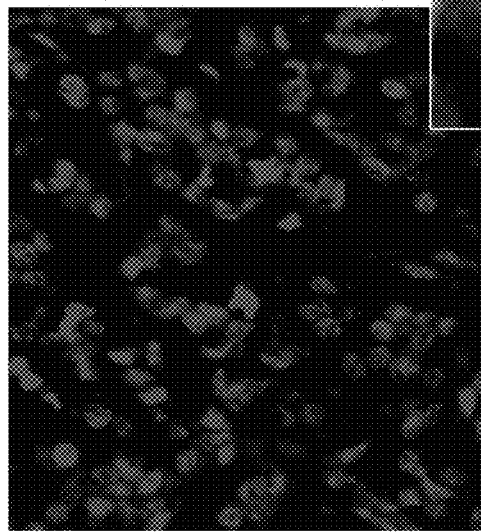
Figure 6D:
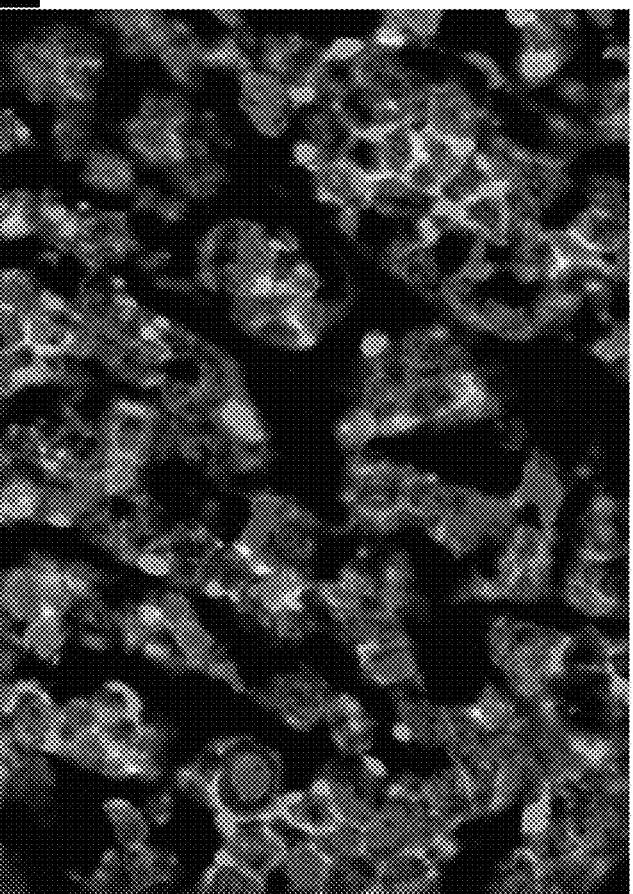

Simultaneous labeling of a single ER-positive, HER2-positive, and Ki-67-positive breast cancer tissue sample with a mixture of three peptide-antibody pairs has also been demonstrated. The sample was treated with a mixture of PEP7-coupled rabbit monoclonal anti-ER primary antibody, PEP5-coupled rabbit monoclonal anti-HER2/neu receptor primary antibody, and PEP1-coupled rabbit monoclonal anti-Ki67 primary antibody. The labeled section was then stained with a mixture of high-affinity Dy550-labeled anti-PEP7, Dy490-labeled anti-PEP5, and Dy755-labeled anti-PEP1. FIGS. 6A-6C show images of the stained tissue section showing emission from (A) the Dy550 channel, (B) the Dy490 channel, and (C) the Dy755 channel. FIG. 6D shows an overlay of images from the three separate channels. The simultaneous labeling of three important diagnostic tumor antigens at high sensitivity and specificity demonstrates the powerful multiplexing capabilities of the instant immunoreagents.

Figure 7:
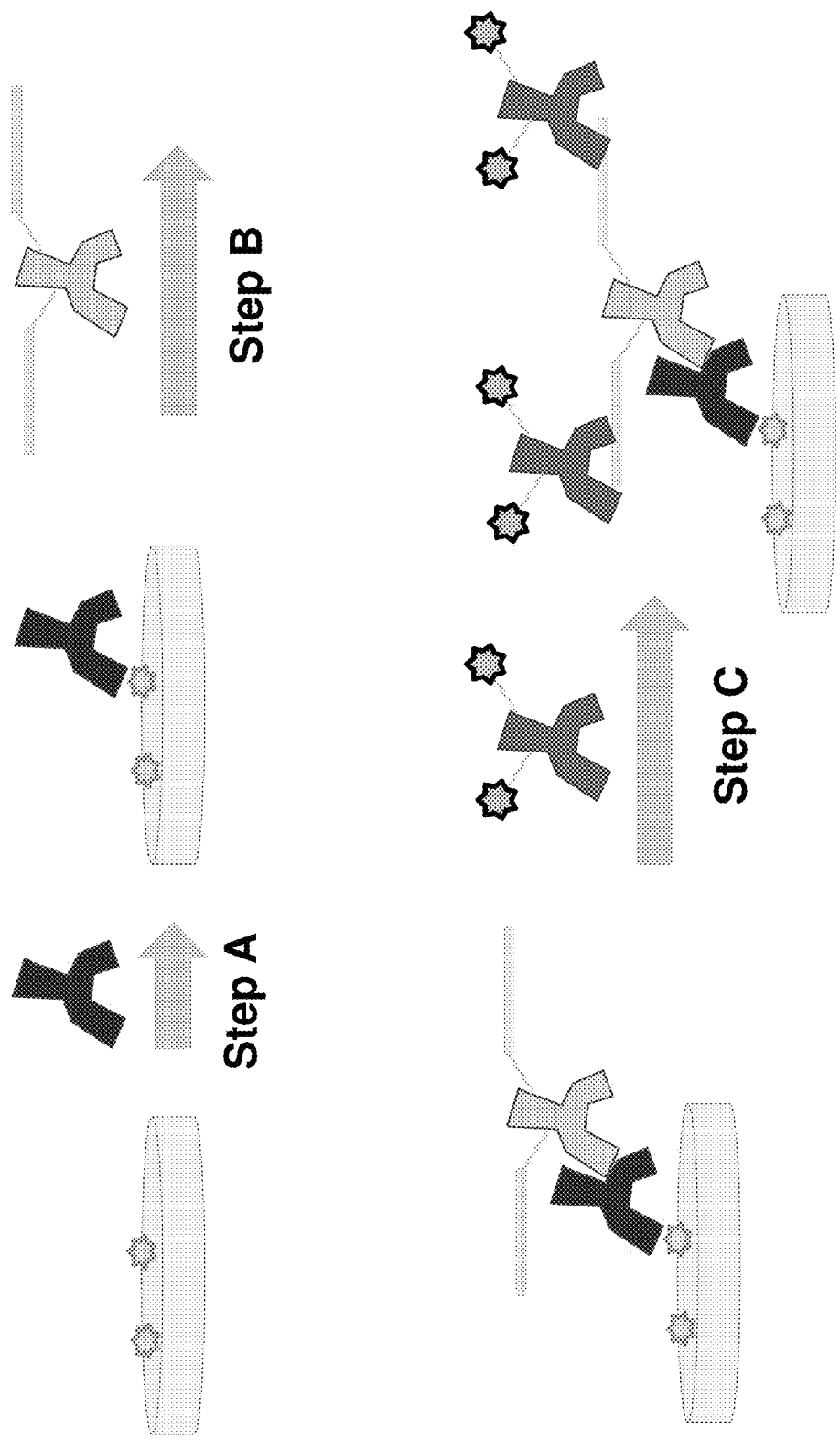
FIG. 7: Schematic representation of an exemplary three-step amplified staining protocol using an antigen-coupled cross-species secondary antibody. Step A: Sample is labeled with an unmodified antibody from a first species; Step B: the bound antibody is labeled with a bridging antigen-coupled cross-species antibody; and Step C: the bridging antigen is stained with a fluorescent antibody specific for the bridging antigen.

The immunoreagents of the instant disclosure may also be used in an amplified three-step staining procedure where the antigen-coupled primary antibody is a cross-species reactive antibody. As shown graphically in FIG. 7, target antigens (gray stars) in a tissue sample of interest are labeled with an unmodified first primary antibody from a first species in step A. The bound antibody is then labeled with an antigen-coupled second primary antibody from a second species that is specific for the constant region of the first antibody in step B. In the FIG. 7 drawing, the coupled bridging antigen is illustrated as two gray lines covalently associated with the second primary antigen. The antigen-coupled second primary antibody is then stained with a detectable secondary antibody that has high affinity for the coupled antigen, as shown in step C.

Figure 8B:
FIG. 8A-FIG. 8B: Results of staining of HER2 (A) and ER (B) in triple-positive breast cancer tissue using a three-step staining procedure with a peptide-coupled cross-species antibody.
Figure 8A:
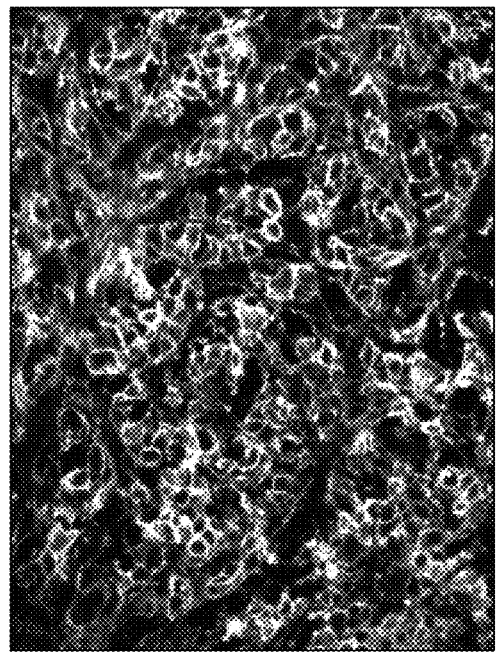

Experimental confirmation of the amplified three-step staining procedure is provided in FIGS. 8A and 8B. In this experiment, a triple-positive (ER+, HER2+, and PR+) breast cancer tissue section was separately labeled with either a rabbit anti-HER2 antibody (A) or a rabbit anti-ER antibody (B). The sections were next labeled with a PEP1-coupled anti-rabbit antibody (A). Finally, the sections were stained with a Dy650-labeled high-affinity anti-PEP6 antibody. The bright staining demonstrates the effectiveness of the technique.

Immunoreagent Panels for Tissue Profiling

The simultaneous staining of a triple-positive breast cancer tissue section using a panel of anti-ER, anti-HER2, and anti-Ki-67 immunoreagent pairs was described above and displayed in FIGS. 6A-6D. The following examples provide further support for the use of defined panels of the instant immunoreagents in the multiplexed staining of diseased tissues. Such panels thus comprise a plurality of immunoreagents, wherein the immunoreagents comprise a primary antibody and a bridging antigen, wherein the primary antibody and the bridging antigen are coupled, and wherein the bridging antigen is recognized by a detectable secondary antibody with high affinity.

For example, FIG. 9A-FIG. 9D demonstrate the use of a panel of the instant immunoreagents for the labeling of a melanoma tissue section. Specifically, CD4, CD20, and CD68 targets on malignant melanoma tissue slides (ILS34116; purchased from ILSBio (www.ilsbio.com)) were simultaneously detected using a panel of peptide-coupled primary antibodies and fluorescent high-affinity anti-peptide secondary antibodies. The primary antibodies and secondary antibodies are described in Table 3. Staining and imaging protocols are as described above.

TABLE 3

| Primary antibody | Target cell | Supplier | Clone | Secondary antibody-fluorophore |
|---|---|---|---|---|
| anti-CD4 | T-cells | Epitomics | EP204 | Anti-PEP7-Dy549P1 |
| anti-CD20 | B-cells | Epitomics | EP7 | Anti-PEP6-Dy649P1 |
| anti-CD68 | Macrophages | Neo Bio | C68/684 | Anti-PEP1-Dy749 |

Figure 9D:
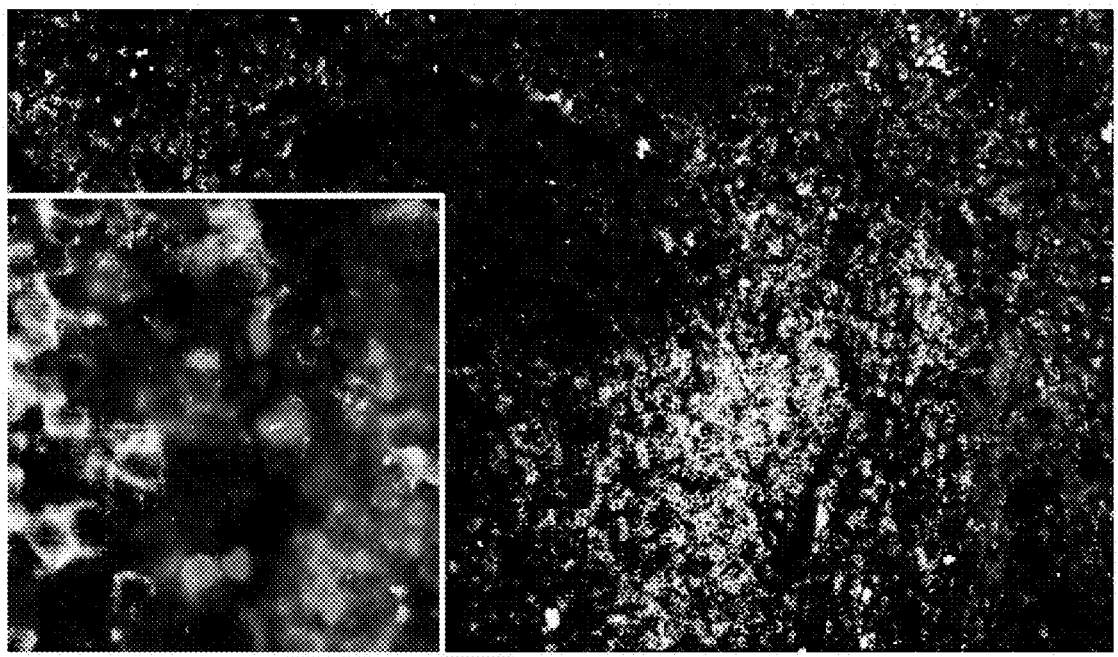
FIG. 9A-FIG. 9D: Multiplexed staining of a melanoma tissue section with three different pairs of peptide-coupled primary and fluorescent high-affinity anti-peptide secondary antibodies. (A) Emission from the anti-CD4 pair; (B) Emission from the anti-CD20 pair; (C) Emission from the anti-CD68 pair; and (D) Overlay of emissions from the anti-CD4, anti-CD20, and anti-CD68 pairs. Insets in FIGS. 9A, 9B, and 9C are zoomed-in views of each section.
Figure 9B:
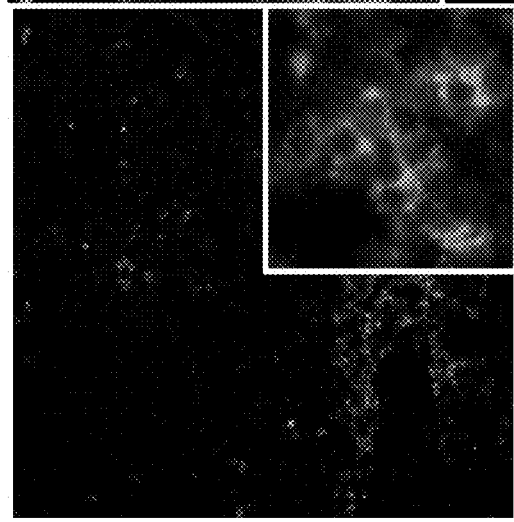
Figure 9A:
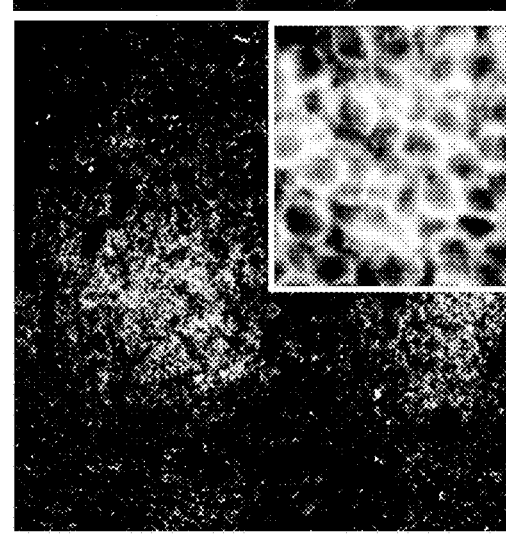
Figure 9C:
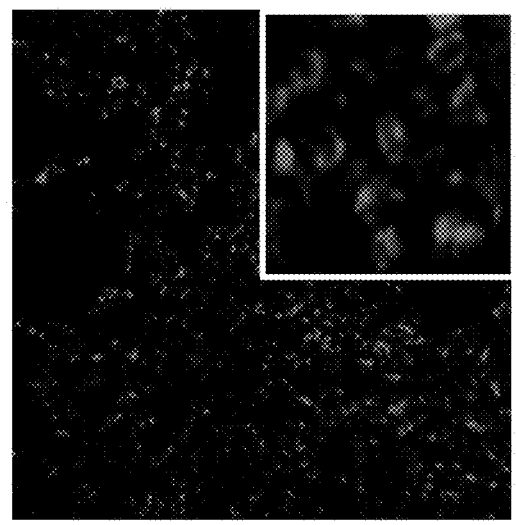

Slides were incubated with a cocktail of primary antibodies conjugated to specific peptide antigens at 5 ug/mL for each antibody. FIG. 9A shows fluorescence of the anti-CD4 immunoreagent staining T cells. FIG. 9B shows fluorescence of the anti-CD20 immunoreagent staining B cells. FIG. 9C shows fluorescence of the anti-CD68 immunoreagent staining macrophages. FIG. 9D shows the combined fluorescence from all three immunoreagents. The insets in each panel represent a zoomed-in region of the slide.

FIG. 10A-FIG. 10D show the simultaneous staining of a triple-negative breast cancer tissue section labeled with a panel of immunoreagents targeting cytokeratin 5 (CK5), cytokeratin 6 (CK6), and Ki-67. The immunoreagents were prepared from the primary antibodies and bridging peptide antigens listed in Table 4. The primary antibodies were detected using fluorescently-labeled, high affinity anti-peptide secondary antibodies. Staining and imaging protocols are as described above.

TABLE 4

| Primary antibody | Clone | Source | Bridging antigen |
|---|---|---|---|
| rabbit monoclonal anti-CK5 | EP24 | Epitomics | PEP5 |
| mouse monoclonal anti-Ki-67 | B56 | BD Pharmingen | PEP1 |
| rabbit monoclonal anti-CK6 | EP67 | Epitomics | PEP7 |

Figure 10A:
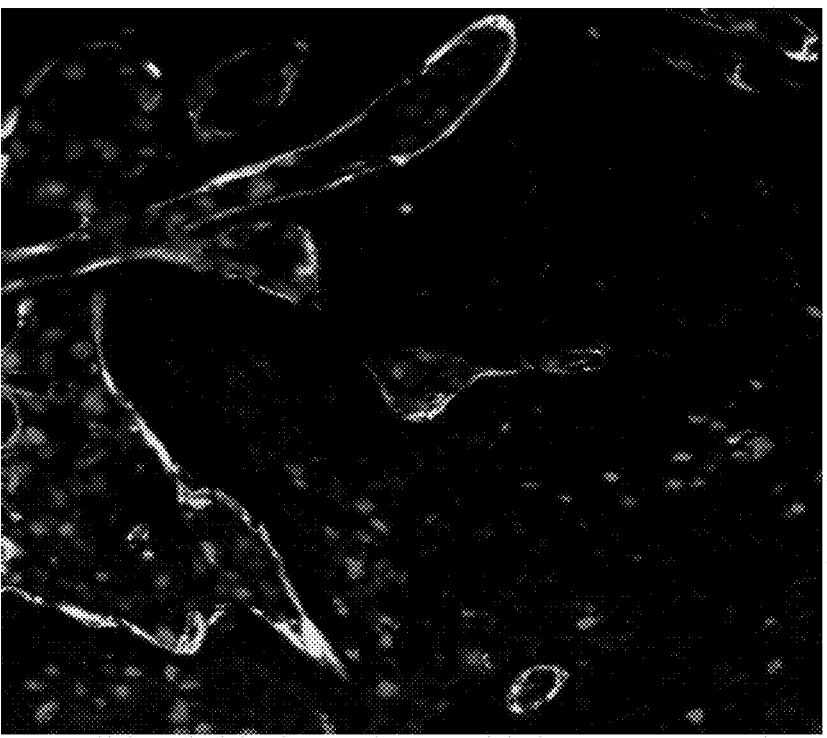
FIG. 10A-FIG. 10D: Multiplexed staining of a triple-negative breast cancer tissue section with three different pairs of peptide-coupled primary and fluorescent high-affinity anti-peptide secondary antibodies. (A) Emission from the anti-CK5 pair; (B) Emission from the anti-CK6 pair; (C) Emission from the anti-Ki-67 pair; and (D) Overlay of emissions from the anti-CK5, anti-CK6, and anti-Ki-67 pairs.
Figure 10B:
Figure 10C:
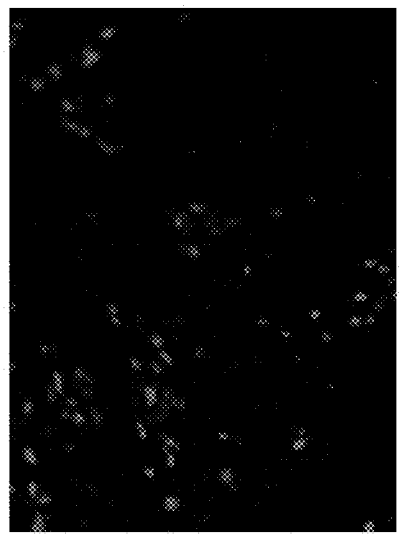
Figure 10D:
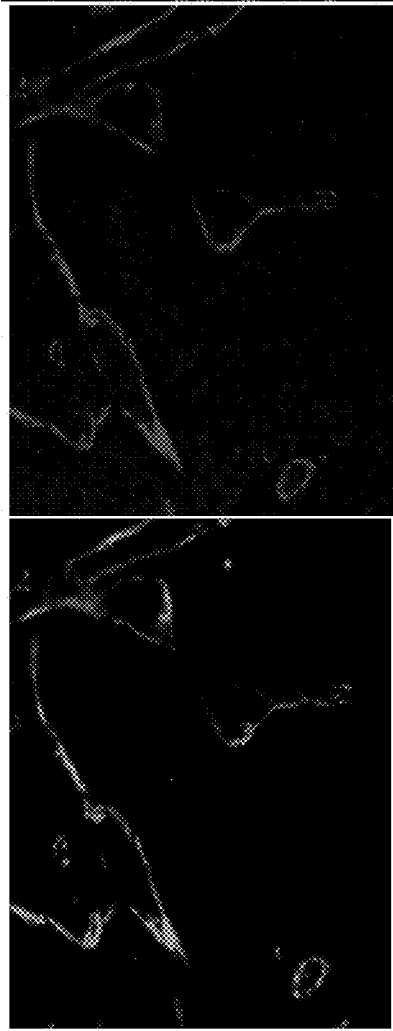

FIG. 10A shows fluorescence from the anti-CK5 immunoreagent pair. FIG. 10B shows fluorescence from the anti-CK6 immunoreagent pair. FIG. 10C shows fluorescence from the anti-Ki67 immunoreagent pair. FIG. 10D shows an overlay of the fluorescence from all three labels.

Figure 11E:
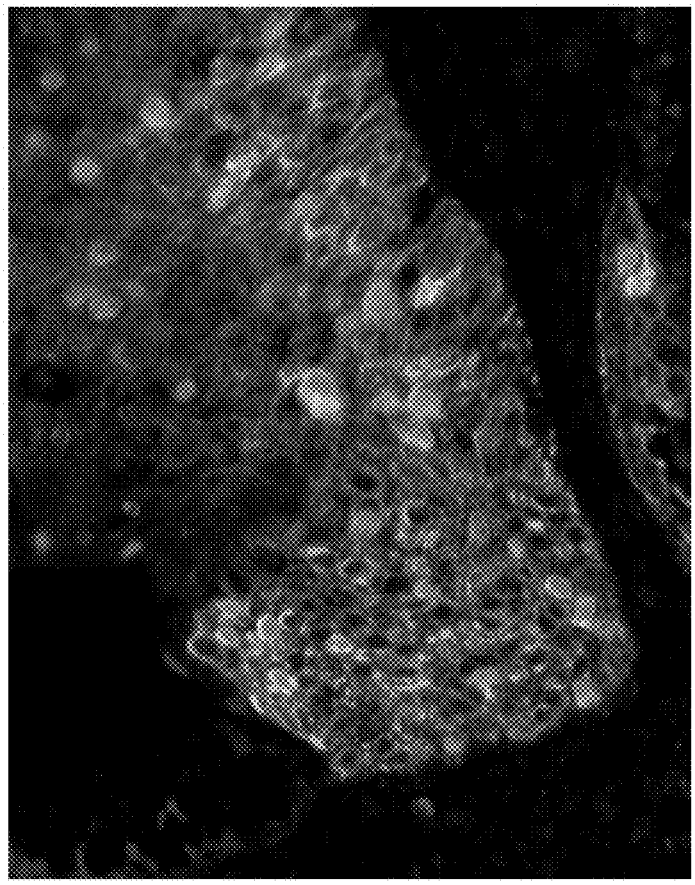
FIG. 11A-FIG. 11E: Multiplexed staining of a squamous cell cervical cancer tissue section with four different pairs of peptide-coupled primary and fluorescent high-affinity anti-peptide secondary antibodies. (A) Emission from the anti-CK5 pair; (B) Emission from the anti-EGFR pair; (C) Emission from the anti-p40 pair; (D) Emission from the anti-Ki-67 pair; and (E) Overlay of emissions from the anti-CK5, anti-EGFR, anti-p40, and anti-Ki-67 pairs.
Figure 11B:
Figure 11D:
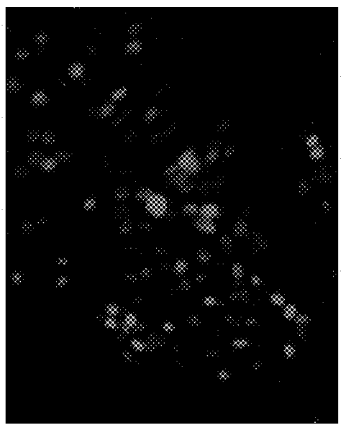
Figure 11A:
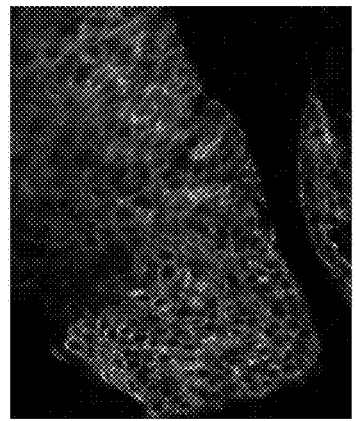
Figure 11C:
Figure 13B:
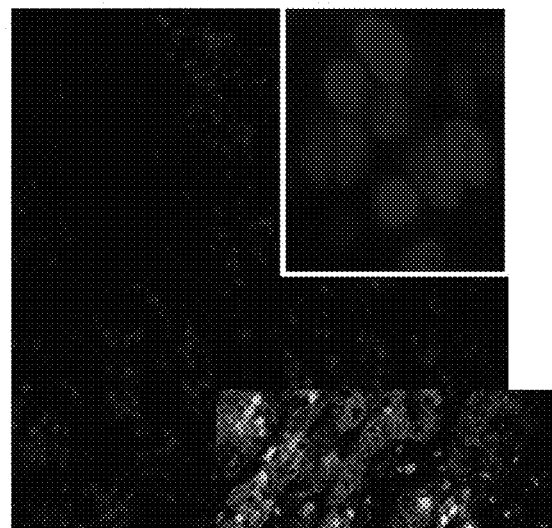
FIG. 13A-FIG. 13E: Four-plex staining of triple-positive breast cancer markers in a single tissue section: (A) HER2, (B) ER, (C) PR, (D) Ki-67, and (E) an overlay of the four images.
Figure 13D:
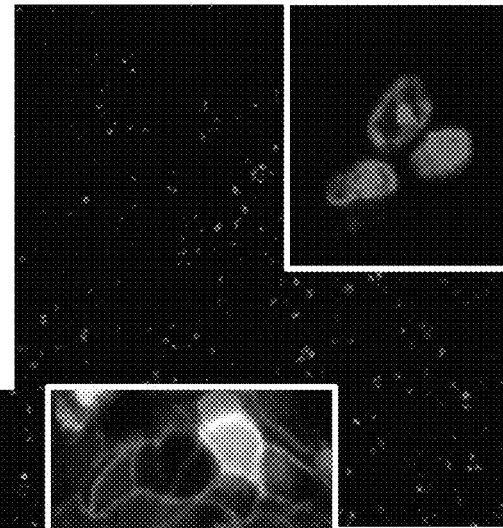
Figure 13E:
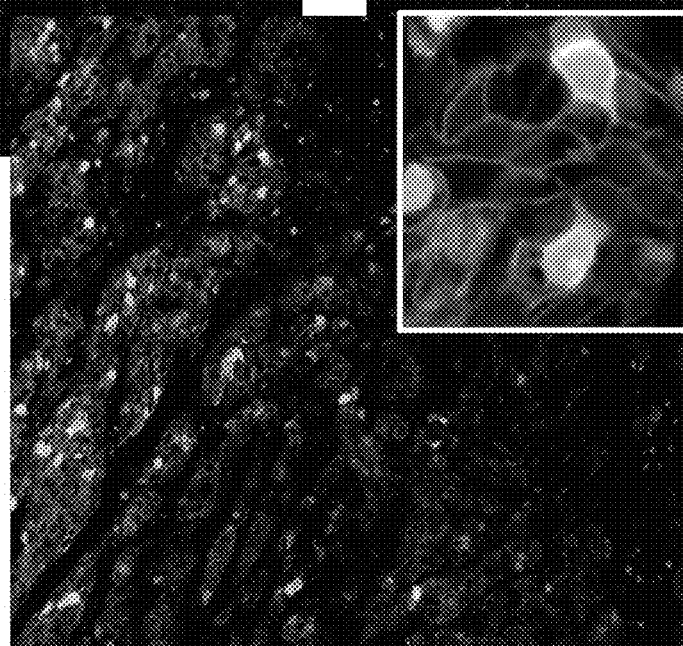
Figure 13A:
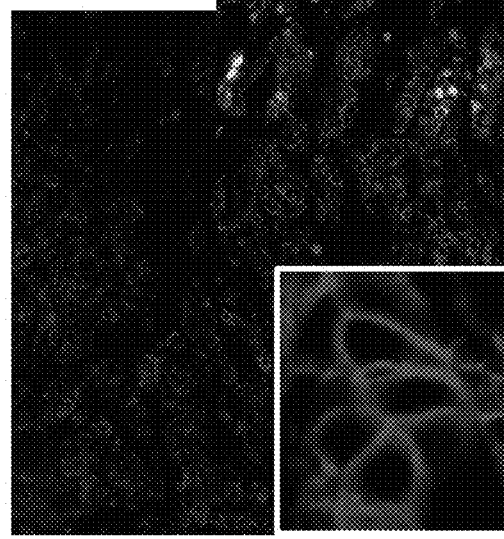
Figure 13C:
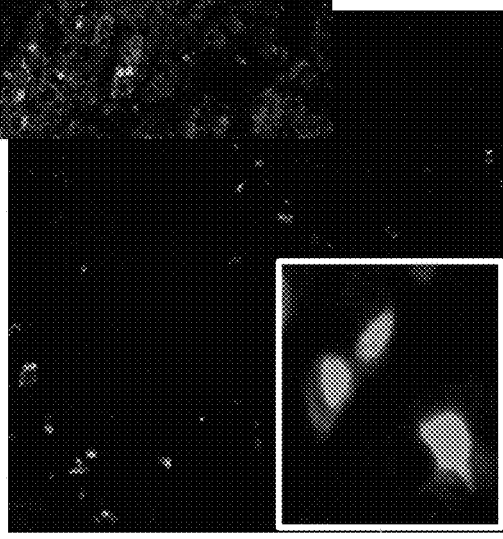

FIG. 11A-FIG. 11E show four-plex labeling of a squamous cell cervical cancer tissue section. Fluorescence specific for CK5 is shown in FIG. 11A, for EGFR is shown in FIG. 11B, for p40 is shown in FIG. 11C, for Ki-67 is shown in FIG. 11D, and an overlay of the fluorescence from all four labels is shown in FIG. 11E. The immunoreagents were prepared from the primary antibodies and bridging antigens listed in Table 5. Staining and imaging protocols are as described above.

TABLE 5

| Primary antibody | Clone | Source | Bridging antigen |
|---|---|---|---|
| rabbit monoclonal anti-CK5 | EP24 | Epitomics | PEP5 |
| mouse monoclonal anti-Ki-67 | B56 | BD Pharmingen | PEP1 |
| mouse monoclonal anti-p40 | 11F12.1 | Millipore | PEP7 |
| rabbit monoclonal anti-EGFR | EP22 | Epitomics | PEP6 |

FIG. 12A-FIG. 12D show the simultaneous labeling of IgA (A), C3c (B), COL4A5 (C), and IgG (D) in glomerulonephtitis cores. The immunoreagents were prepared from the primary antibodies and bridging antigens listed in Table 6. The fluorescence from each of the immunoreagent pairs is shown separately. Staining and imaging protocols are as described above.

TABLE 6

| Primary antibody | Clone | Source | Bridging antigen |
|---|---|---|---|
| rabbit anti-human IgA | polyclonal | Aviva Biosys | PEP5 |
| rabbit anti-human IgG | polyclonal | Aviva Biosys | PEP1 |
| sheep anti-human Complement 3c (C3c) | polyclonal | Aviva Biosys | PEP7 |
| rabbit anti-human Collagen IV alpha chain 5 (COL4A5) | polyclonal | Aviva Biosys | PEP6 |

Multiplex Staining of Serial Tissue Sections with Fluorescent Immunoreagent Panels In any tissue, normal or diseased, there are many types of cells, including immune cells, interacting with one another within the tissue. There is thus a need to identify, quantify, and determine the density and relative location of the cells within a tissue of interest. Such characterization of cells within a tissue is particularly important in cancer tissues as it has recently been discovered that tumors produce signals on their surfaces to block immune cells from attacking and clearing the tumor. Checkpoint inhibitor drugs such as pembrolizumab (Keytruda) and nivolumab (Opdivo) inhibit this blocking, thus allowing T cells and other lymphocytes to clear tumors. Such treatments can therefore lead to durable cures in certain percentages of patients in a variety of tumors including melanoma, non-small cell lung cancer (NSCLC), breast and bladder cancers. Tumeh et al. (2014) Nature 515: 568-571 (DOI:10.1038/nature13954). There is, however, no diagnostic test currently available that can pre-determine whether the checkpoint inhibitor drug will be effective. Identification of the many different cells present in the stroma, and determination of the correlation between infiltration of tumor infiltrating lymphocytes (TILs) and therapeutic outcome will therefore have a major impact in identifying factors that can lead to directed therapies.

To further expand the number of immune and other important cell types that can be identified in a diseased tissue, it is demonstrated here using the described immunoreagents directed at markers on immune cells that multiple cellular biomarkers can be detected simultaneously. Further it has been demonstrated here using serial tissue specimens and multiple panels of immunoreagents that signals from each serial tissue can be overlaid to detect, for example, 8 and 11 target markers simultaneously. In one example (described below), four triple-positive breast cancer markers (ER, PR, HER2, and Ki-67) were overlain with four immune cell markers (CD3, CD4, CD8, and CD20), leading to an image with 8 total target markers. In a second example (also shown below) four triple-negative breast cancer markers (EGFR, CK5, vimentin, and Ki-67) were overlain with the same panel of immune cell markers (CD3, CD4, CD8, and CD20) to produce another 8-plex image.

In yet another example (also described below), three panels of immunoreagents were used to detect multiple markers on three serial tissues. In this example, three serial triple-negative breast cancer tissue specimens were labeled with immunoreagents targeting the above four triple-negative cancer markers (CK5, EGFR, vimentin, and Ki-67), a set of four immune markers on a second serial tissue (CD4, CD8, CD68, and FoxP3), and a second set of three immune markers on a third serial tissue (CD3, PD-1, and PD-L) to produce an 11-plex image. These images demonstrate the ability to visualize multiple immune markers in sections of tumor tissue.

Specifically, FIG. 13A-FIG. 13E show the simultaneous labeling of ER, PR, HER2, and Ki-67 on triple-positive breast cancer tissue (ILS32707; ILSBio, Chestertown, MD). The immunoreagents were prepared from the primary antibodies and bridging antigens listed in Table 7. The fluorescence from each of the immunoreagent pairs is shown separately. Staining and imaging protocols are as described above.

TABLE 7

| Primary antibody | Clone | Source | Bridging antigen |
|---|---|---|---|
| rabbit monoclonal anti-ER | EP1 | Epitomics | PEP7 |
| rabbit monoclonal anti-PR | EP2 | Epitomics | PEP6 |

TABLE 7-continued

| Primary antibody | Clone | Source | Bridging antigen |
|---|---|---|---|
| mouse monoclonal anti-HER2 | EP3 | Epitomics | PEP5 |
| mouse monoclonal anti-Ki-67 | B56 | BD Pharmingen | PEP1 |

FIG. 14A-FIG. 14E show the simultaneous labeling of CD3, CD4, CD8, and CD20 on a serial tissue with respect to tissue data presented in FIG. 13 for triple-positive breast cancer tissue (ILS32707; ILSBio, Chestertown, MD). The immunoreagents were prepared from the primary antibodies and bridging antigens listed in Table 8. The fluorescence from each of the immunoreagent pairs is shown separately. Staining and imaging protocols are as described above.

TABLE 8

| Primary antibody | Clone | Source | Bridging antigen |
|---|---|---|---|
| rabbit monoclonal anti-CD4 | EP204 | Epitomics | PEP7 |
| rabbit monoclonal anti-CD8 | EP334 | Epitomics | PEP5 |
| rabbit monoclonal anti-CD20 | EP7 | Epitomics | PEP6 |
| rabbit monoclonal anti-CD3 | EP177 | Epitomics | PEP1 |

Figure 15:
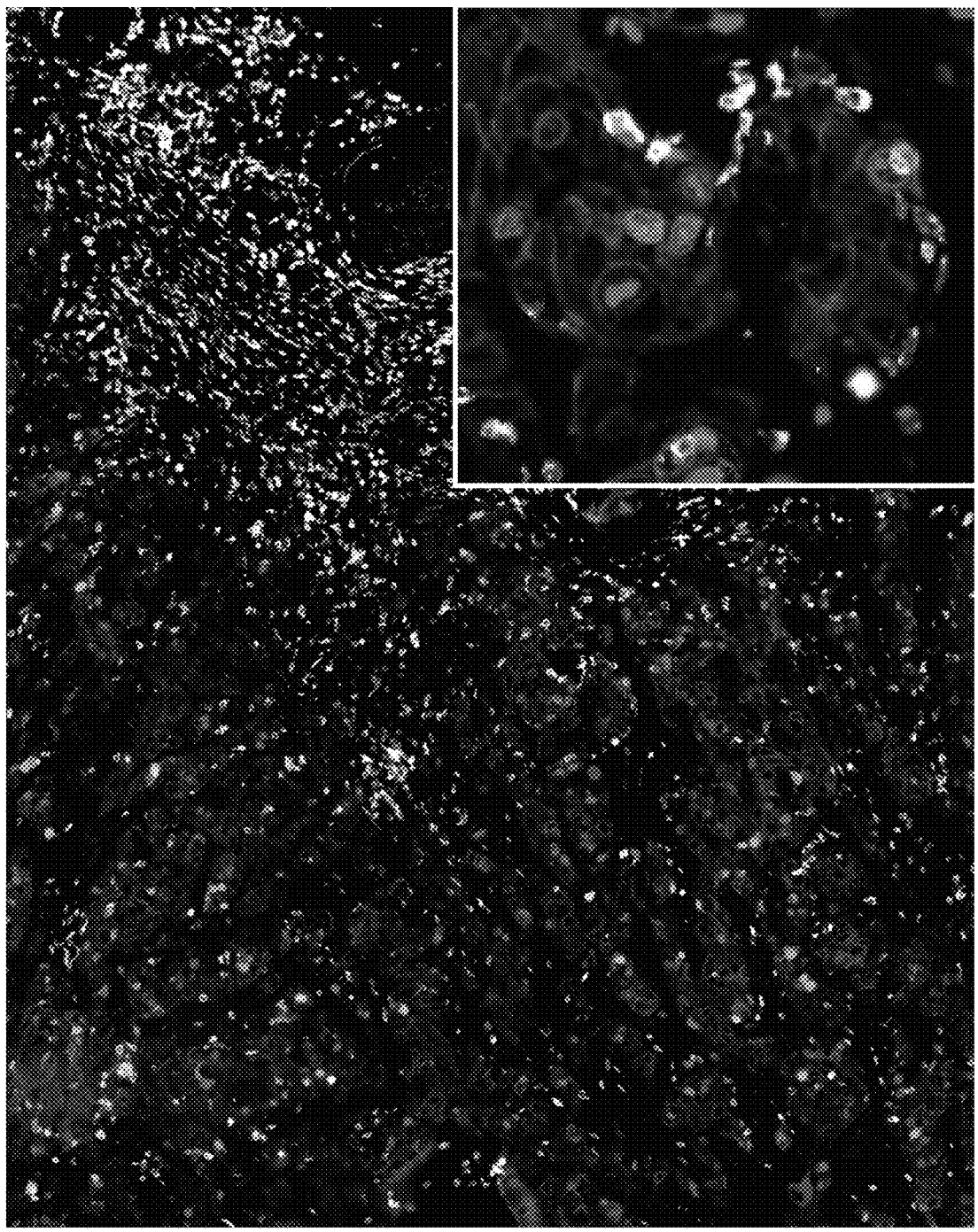
FIG. 15: Overlay of serial tissue staining results from four-plex staining with triple-positive breast cancer panel (FIG. 14) and four-plex immune marker panel (FIG. 15), showing HER2, ER, PR, Ki-67, CD3, CD4, and CD8.

FIG. 15 shows the overlay of serial tissue staining results from four-plex staining with triple positive breast cancer panel (FIG. 13) and four-plex immune marker panel (FIG. 14). HER2 (red in original), ER (blue in original), PR (green in original), Ki-67 (magenta in original), CD3 (cyan in original), CD4 (thallium in original), and CD8 (orange in original). Note that CD20 is not shown due to limitations in the imaging software.

FIG. 16A-FIG. 16E show the simultaneous labeling of EGFR, CK5, vimentin, and Ki-67 on triple-negative breast cancer tissue (ILS36851; ILSBio, Chestertown, MD). The immunoreagents were prepared from the primary antibodies and bridging antigens listed in Table 9. The fluorescence from each of the immunoreagent pairs is shown separately. Staining and imaging protocols are as described above.

TABLE 9

| Primary antibody | Clone | Source | Bridging antigen |
|---|---|---|---|
| rabbit monoclonal anti-CK5 | EP24 | Epitomics | PEP5 |
| rabbit monoclonal anti-EGFR | EP22 | Epitomics | PEP6 |
| rabbit monoclonal anti-vimentin | EP21 | Epitomics | PEP7 |
| rabbit monoclonal anti-Ki-67 | B56 | BD Biosciences | PEP1 |

FIG. 17A-FIG. 17E show the simultaneous labeling of CD3, CD4, CD8 and CD20 on a serial tissue with respect to tissue data presented in FIG. 14 triple negative breast cancer tissue (ILS36851; ILSBio, Chestertown, MD). The immunoreagents were prepared from the primary antibodies and bridging antigens listed in Table 8. The fluorescence from each of the immunoreagent pairs is shown separately. Staining and imaging protocols are as described above.

Figure 18:
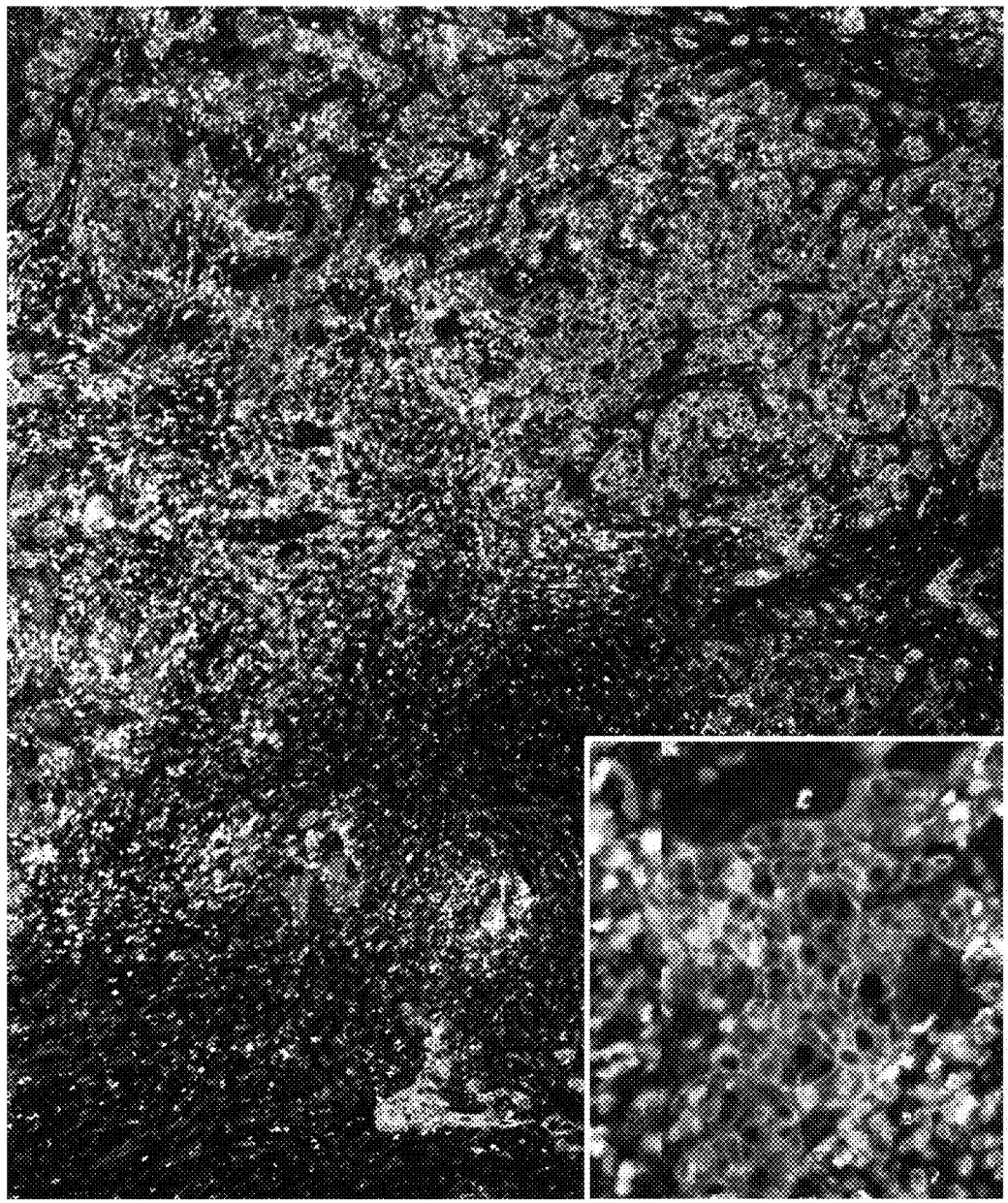
FIG. 18: Overlay of serial tissue staining results from four-plex staining with triple-negative breast cancer panel (FIG. 16) and four-plex immune marker panel (FIG. 17), showing EGFR, vimentin, CK5, Ki-67, CD3, CD4, and CD8. (CD20 not shown due to software limitations.)

FIG. 18 shows the overlay of serial tissue staining results from four-plex staining with triple-negative breast cancer panel (FIG. 16) and four-plex immune marker panel (FIG. 17). EGFR (red in original), vimentin (blue in original), CK5 (green in original), Ki-67 (magenta in original), CD3 (cyan in original), CD4 (thallium in original) and CD8 (orange in original). Note that CD20 is not shown due to limitations in the imaging software.

Figure 19:
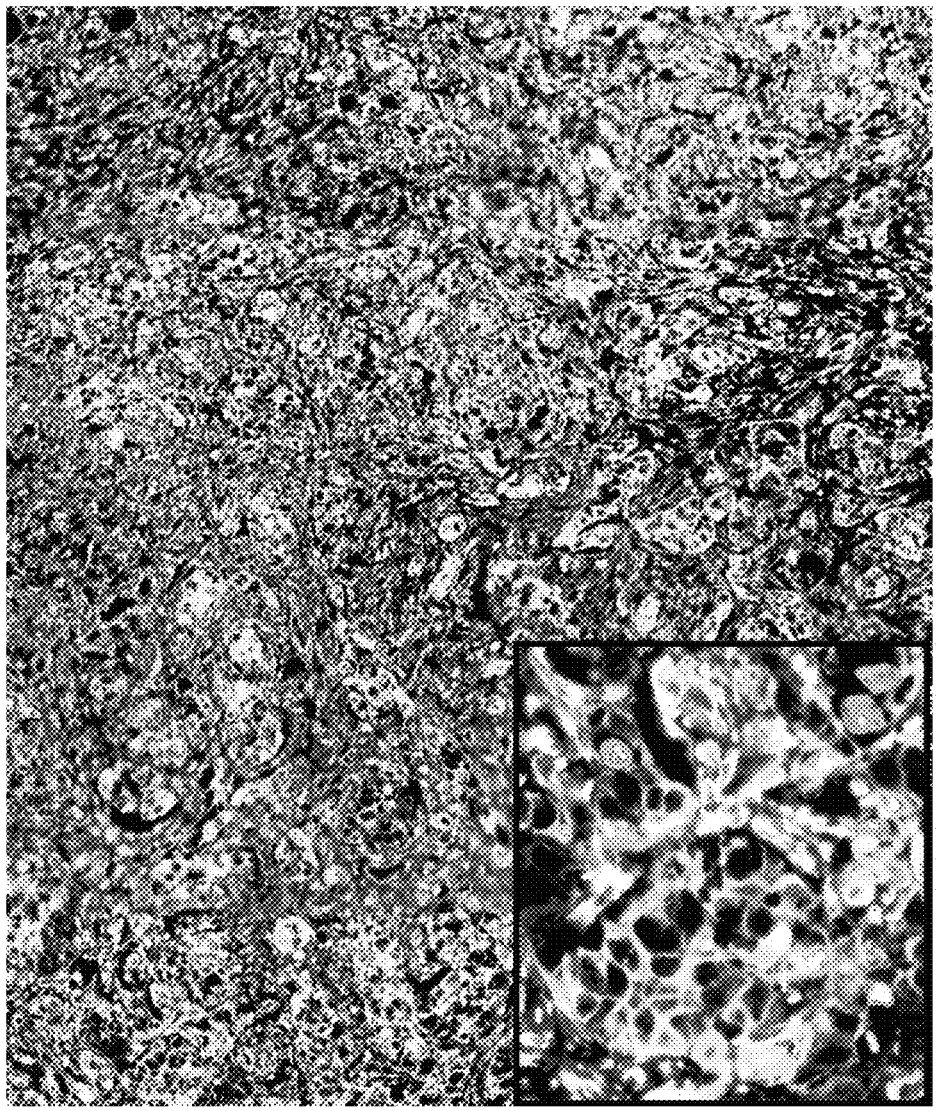
FIG. 19: Overlay of four-plex staining of triple negative-breast cancer tissue detecting CK5, vimentin, EGFR, and Ki-67.

FIG. 19 shows the simultaneous labeling of EGFR, CK5, vimentin and Ki-67 on triple-negative breast cancer tissue (ILS36851; ILSBio, Chestertown, MD). The immunoreagents were prepared from the primary antibodies and bridging antigens listed in Table 9. The fluorescence from each of the immunoreagent pairs is shown separately. Staining and imaging protocols are as described above. CK5 (yellow in original), vimentin (silver in original), EGFR (turquoise in original), and Ki-67 (rainbow in original).

Figures 20A, 20B:
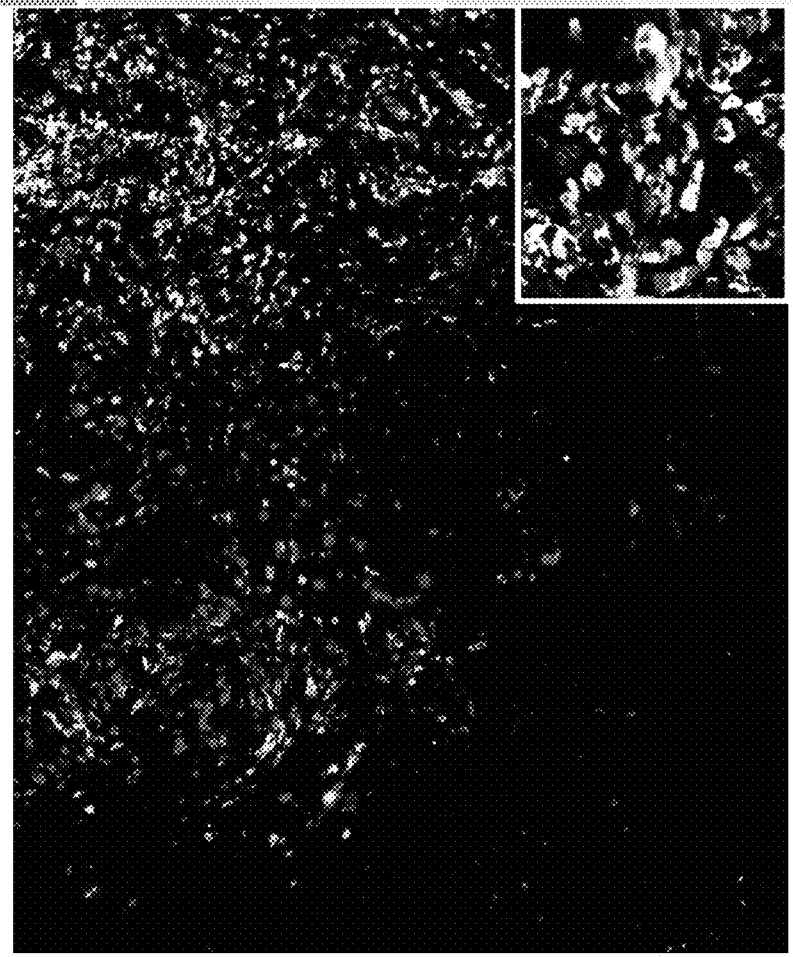
FIG. 20A: Overlay of four-plex staining of triple-negative breast cancer tissue detecting CD4, CD8, CD68, and FoxP3.
FIG. 20B: Exemplary single-cell images, showing marker phenotypes (and predicted cell type) and total counts of each phenotype within a representative view from the section of FIG. 20A.

FIG. 20A shows the simultaneous labeling of CD4, CD8, CD68, and FoxP3 on a serial tissue with respect to tissue data presented in FIG. 19 triple negative breast cancer tissue (ILS36851; ILSBio, Chestertown, MD). The immunoreagents were prepared from the primary antibodies and bridging antigens listed in Table 10. The fluorescence from each of the immunoreagent pairs is shown separately. Staining and imaging protocols are as described above. CD4 (thallium in original), CD8 (orange in original), CD68 (magenta in original), and FoxP3 (red in original).

TABLE 10

| Primary antibody | Clone | Source | Bridging antigen |
|---|---|---|---|
| rabbit monoclonal anti-CD4 | EP204 | Epitomics | PEP7 |
| rabbit monoclonal anti-CD8 | EP334 | Epitomics | PEP5 |
| rabbit monoclonal anti-CD68 | C68/684 | Neobio-technologies | PEP1 |
| rabbit monoclonal anti-FoxP3 | EP340 | Epitomics | PEP6 |

FIG. 20B shows separate exemplary close-up cellular images taken from the view of FIG. 20A. The marker phenotype for each cell image is shown (as well as the predicted cell type). Also shown is the quantitation of cell counts for each cell type in the original section. CyteSeer software (Vala Sciences, San Diego, CA) was used to determine phenotype count.

Figure 21:
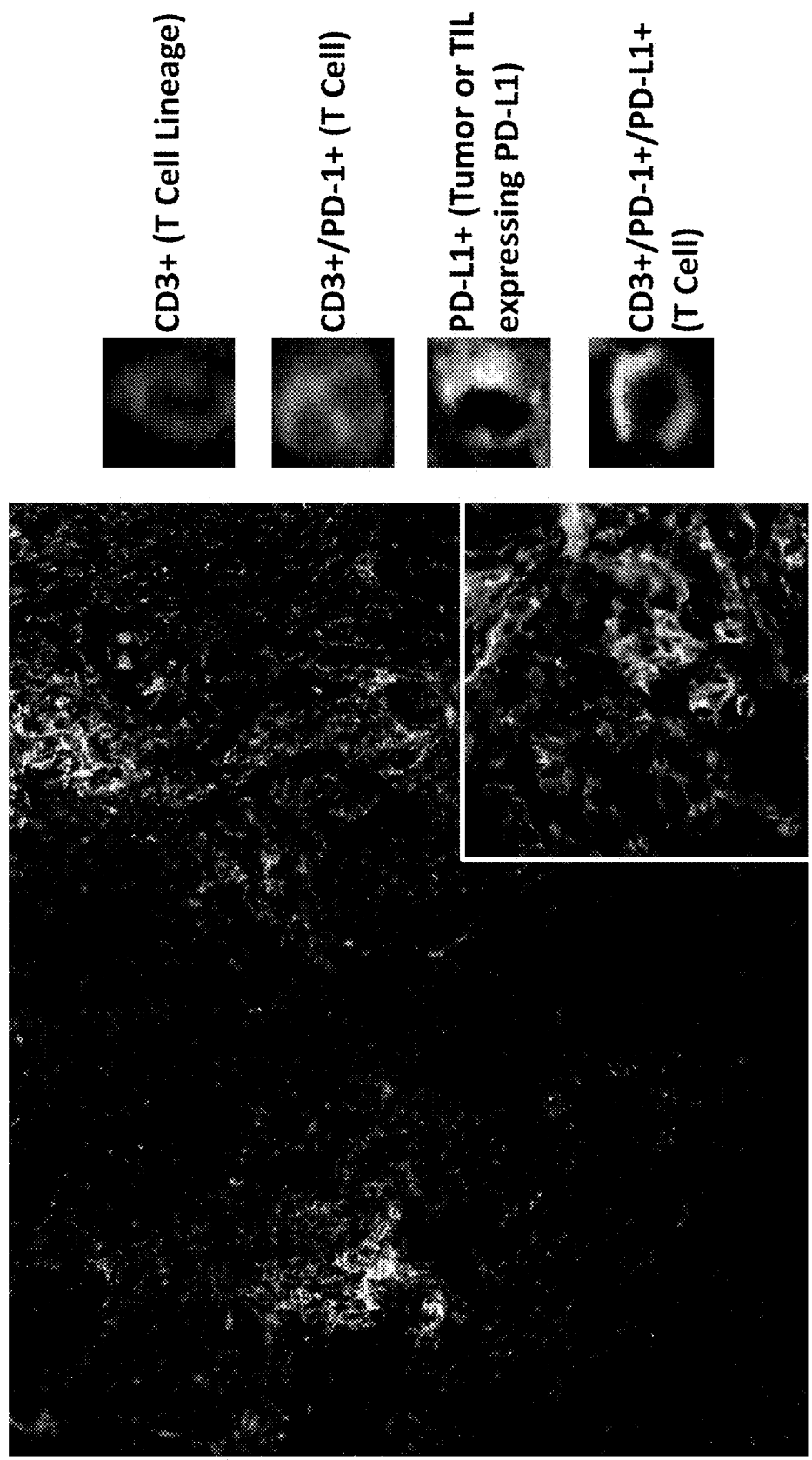
FIG. 21: Overlay of three-plex staining of triple-negative breast cancer tissue detecting CD3, PD-1, and PD-L1. Representative single-cell images and their phenotypes are also shown. (TIL=Tumor infiltrating lymphocytes).

FIG. 21 shows the simultaneous labeling of CD3, PD-1, and PD-L1 on a serial tissue with respect to tissue data presented in FIG. 20 for triple-negative breast cancer tissue (ILS36851; ILSBio, Chestertown, MD). The immunoreagents were prepared from the primary antibodies and bridging antigens listed in Table 11. The fluorescence from each of the immunoreagent pairs is shown separately. Staining and imaging protocols are as described above. CD3 (red in original), PD-1 (green in original), and PD-L1 (cyan in original). Also shown are exemplary close-up cellular images with their marker phenotypes and predicted cell types.

TABLE 11

| Primary antibody | Clone | Source | Bridging antigen |
|---|---|---|---|
| rabbit monoclonal anti-CD3 | EP177 | Epitomics | PEP1 |
| rabbit monoclonal anti-PD-1 | EP239 | Epitomics | PEP6 |
| rabbit monoclonal anti-PD-L1 | CAL10 | Calico Bio | PEP5 |

Figure 22:
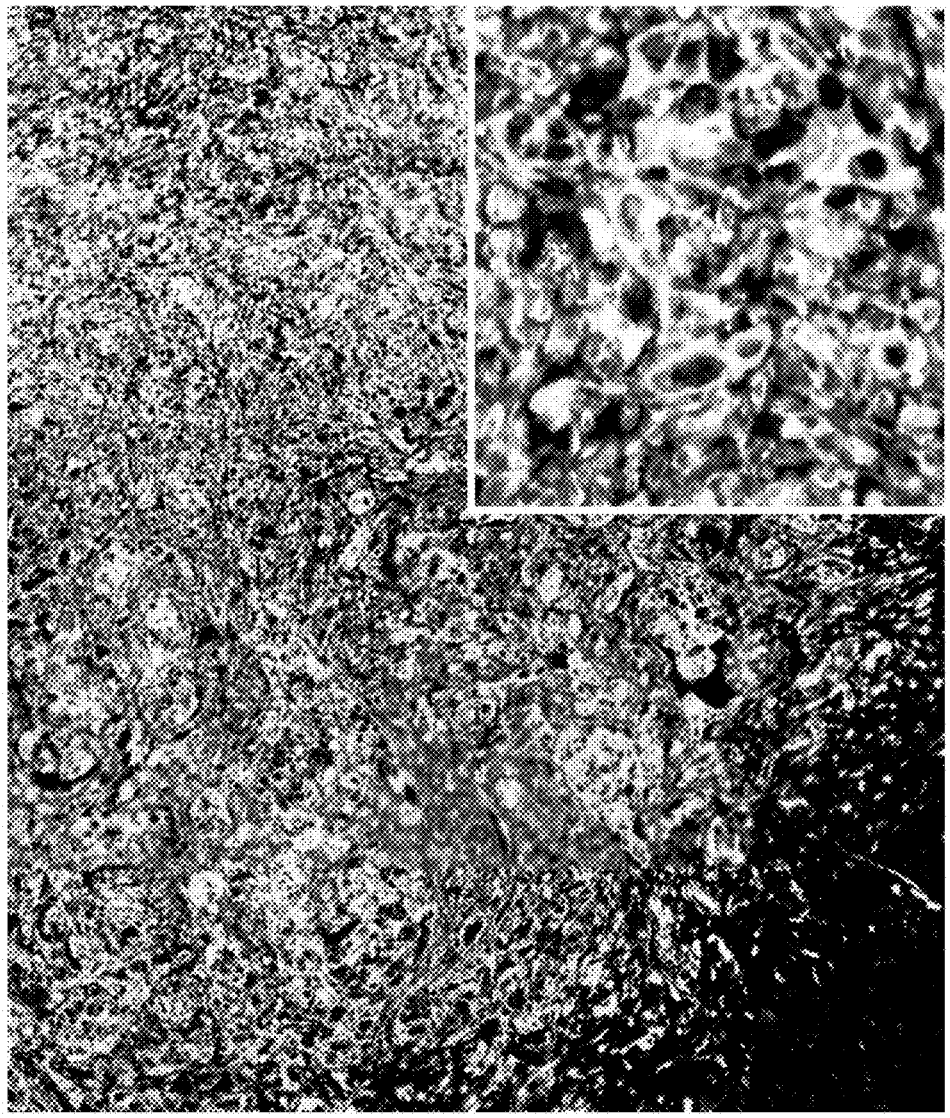
FIG. 22: Overlay of three serial tissues of multiplex staining with a triple-negative breast cancer panel (FIG. 19), a four-plex immune marker panel (FIG. 20A), and a three-plex immune marker panel (FIG. 21).

FIG. 22 shows the overlay of three serial tissue staining results using the four-plex triple-negative breast cancer panel (FIG. 19), the four-plex immune marker panel (FIG. 20), and the three-plex immune marker panel (FIG. 21). CK5 (yellow in original), EGFR (turquoise in original), vimentin (Thai in original), Ki-67 (rainbow in original), FoxP3 (red in original), CD68 (magenta in original), CD4 (thallium in original), CD8 (orange in original), CD3 (blue in original), PD-1 (green in original), and PD-L1 (cyan in original).

Selective Stripping of Immunoreagents Using Soluble Peptide

The ability to stain and strip both Western blot and immunohistochemistry assays to identify more than a single marker on a sample surface typically requires harsh conditions. For example, in immunofluorescence assays to detect more than three markers, such as described in the Opal tyramide signal amplification (TSA)-based assay from PerkinElmer (www.perkinelmer.com), a 15 min microwave treatment of the tissue in a mild acidic buffer is required to strip the primary antibody/secondary antibody-HRP conjugate. A second reported method employs a sodium azide/sodium peroxidase treatment to inactive the HRP. Ortiz de Montellano et al. (1988) *Biochemistry* 27:5470-5476 (DOI: 10.1021/bi00415a013). Others have developed a method to strip primary antibodies from tissues that requires relatively high temperatures and the use of a denaturing detergent. Pirici et al. (2009) *J. Histochem. Cytochem.* 57:567-575 (DOI: 10.1369/jhc.2009.953240).

Figure 23:
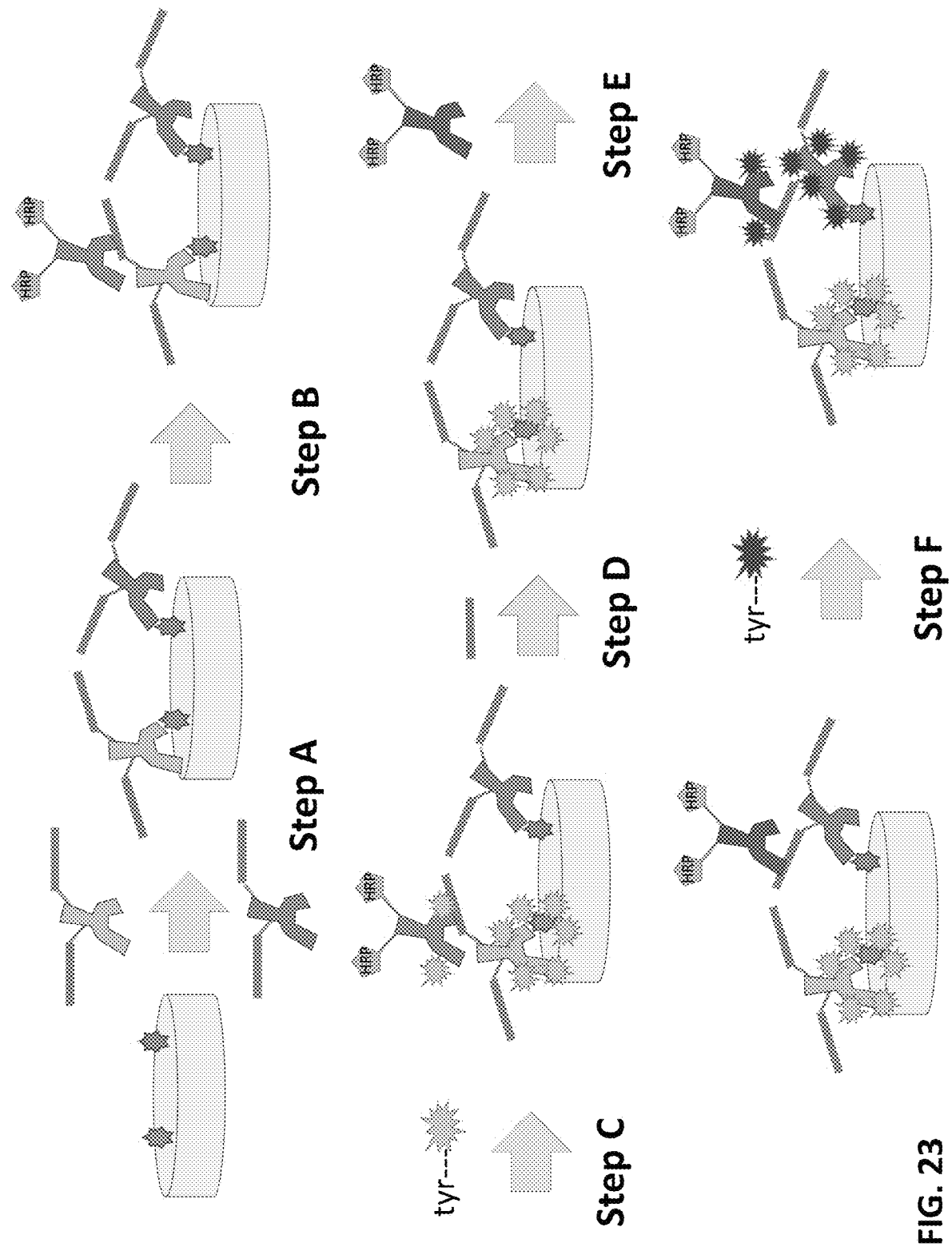
FIG. 23: Schematic representation of an exemplary sequential tyramide staining amplification protocol with two targets on the same tissue sample. The first detectable secondary antibody is selectively stripped from the sample by treatment with an excess of a soluble form of the bridging antigen in step D.

As described and demonstrated herein, the instant immunoreagents can be selectively stripped from a tissue sample under mild conditions by treatment of the sample with an excess of a soluble form of the bridging antigen. In particular, FIG. 23 schematically illustrates an exemplary version of the procedure, where two target antigens are labeled in step A with two specific immunoreagents having different bridging antigens. In step B, the sample is reacted with a first reactive secondary antibody that is specific for the bridging antigen of the first immunoreagent with high affinity. In this example, the reactive secondary antibody carries a horse radish peroxidase as the reactive group. The sample is treated with a fluorescently-labeled tryamide reagent in step C, thus modifying sample proteins, including the first immunoreagent, in proximity to the first target antigen.

The first reactive secondary antibody is next selectively dissociated from the sample, as shown in step D, by treatment with a soluble form of the bridging antigen. Because the soluble bridging antigen is an effective competitor for the binding site of the secondary antibody, and because the soluble bridging antigen can be provided at a relatively high effective concentrations, this step can be performed under mild conditions, thus minimizing damage to the sample. Steps E and F of the procedure are the same as steps B and C, except that the second reactive secondary antibody used in step E is specific for the bridging antigen of the second immunoreagent, and the fluorescently-labeled tyramide reagent of step F carries a detectably distinct fluorophore from tyramide reagent used in step C. After the reaction of step F, the sample can be imaged to detect the location of the first and second detectable reagents and thus the locations of the first and second target antigens.

It should be understood that the above process can readily be modified to detect as many target antigens as desired, simply by treating the sample with additional immunoreagents of the instant invention, wherein the immunoreagents are specific for the additional antigens. The additional immunoreagents are sequentially labeled by repeating steps B, C, and D of FIG. 23 as many times as necessary with the appropriate reactive secondary antibodies, fluorescently-labeled tyramide reagents, and soluble bridging antigens, as would be understood by those of ordinary skill in the art.

In the above described and demonstrated method of selectively dissociating reactive secondary antibodies from a sample, the primary antibodies and associated bridging antigens remain bound to the sample throughout the process, thus limiting further rounds of labeling to reactive secondary antibodies that are specific for different bridging antigens. In a variation of the above technique, the bridging antigen may be coupled to the primary antibody using a cleavable linker, thus allowing selective dissociation of the reactive secondary antibody by cleavage of the linker, either alone, or in combination with the addition of an excess of the soluble bridging antigen. Cleavable linkers are known in the art that are cleavable by, for example, enzymes, nucleophilic/basic reagents, reducing agents, photo-irradiation, electrophilic/acidic reagents, organometallic and metal reagents, and oxidizing reagents (see, e.g., Leriche et al. (2012) *Bioorg. Med. Chem.* 20:571-582 (doi:10.1016/j.bmc.2011.07.048)). By cleavage of the bridging antigen from the primary antibody during each labeling cycle, subsequently-added primary antibodies can be labeled using the same bridging antigen. Use of primary antibodies labeled with the same bridging antigen in each cycle simplifies the process, as the same reactive secondary antibody (e.g., an HRP-labeled secondary antibody) can also be used in each cycle. As was true in the above-described method, differences in labeling of the different target antigens are achieved by the use of different detectable reagents (e.g., tyramide reagents labeled with different fluorophores).

FIG. 24A-FIG. 24C illustrates the staining of HER2 and ER on a single triple-positive breast cancer tissue using the described method with further details provided below. FIG. 24A shows the staining of HER2 using a PEP5-labeled primary antibody, an HRP-labeled anti-PEP5 secondary antibody, and a tyramide-Dy490 fluorescent reagent. The anti-PEP5 secondary antibody was stripped using an excess of PEP5 peptide. FIG. 24B shows the subsequent staining of ER on the same tissue section using a PEP7-labeled primary antibody, an HRP-labeled anti-PEP7 secondary antibody, and a tyramide-Dy550 fluorescent reagent. FIG. 24C shows an overlay of the two images (HER2, red in original; ER, blue in original).

Benefits of this method include: (1) all primary antibodies can be added simultaneously unlike prior art methods, where stringent stripping conditions do not allow the simultaneous addition of primary antibodies; (2) fluorescent labels are not exposed to heat or harsh chemicals, thus damaging their signal output; and (3) imaging needs to be performed only once, at the end of the staining steps.

Experimental

The selective stripping method used to obtain the images of FIG. 24A-FIG. 24C was performed on triple positive breast cancer tissue follows:
1) incubation with a cocktail of anti-HER2-PEP5 and anti-ER-PEP7 for one hour.
2) tissue was washed 3× with PBS
3) incubation with anti-PEP5-antibody-HRP conjugate for 30 minutes,
4) washed 3× wash buffer (PBS/2% tween20)
5) treated with tyramide-Dy-490 for 10 min.
6) washed 3× with wash buffer
7) tissue was incubated with a 150 µM solution of PEP5 peptide in PBS followed by washing for 10 min.
8) washed 3× with wash buffer
9) incubation with anti-PEP7-antibody-HRP conjugate for 30 min
10) washed 3× with wash buffer
11) incubated with tyramide-Dy550
12) added Fluoroshield with DAPI (SigmaAldrich, St. Louis, MO)
13) covered with a cover slip
14) image Bridging Antigens with Multiple Antigenic Determinants It is recognized that consecutive affinity peptide repeats, i.e. tandem repeats, incorporated into proteins produce a significantly higher signal on the binding of fluorescently-labeled anti-peptide antibodies. For example, it has been shown that the incorporation of repetitive GCN4 peptide epitopes within a protein sequence can significantly increase the detectability of the labeled protein using a fluorescent anti-GCN4-antibody derivative. Tanenbaum et al. (2014) *Cell* 159:635-646.

Figure 25:
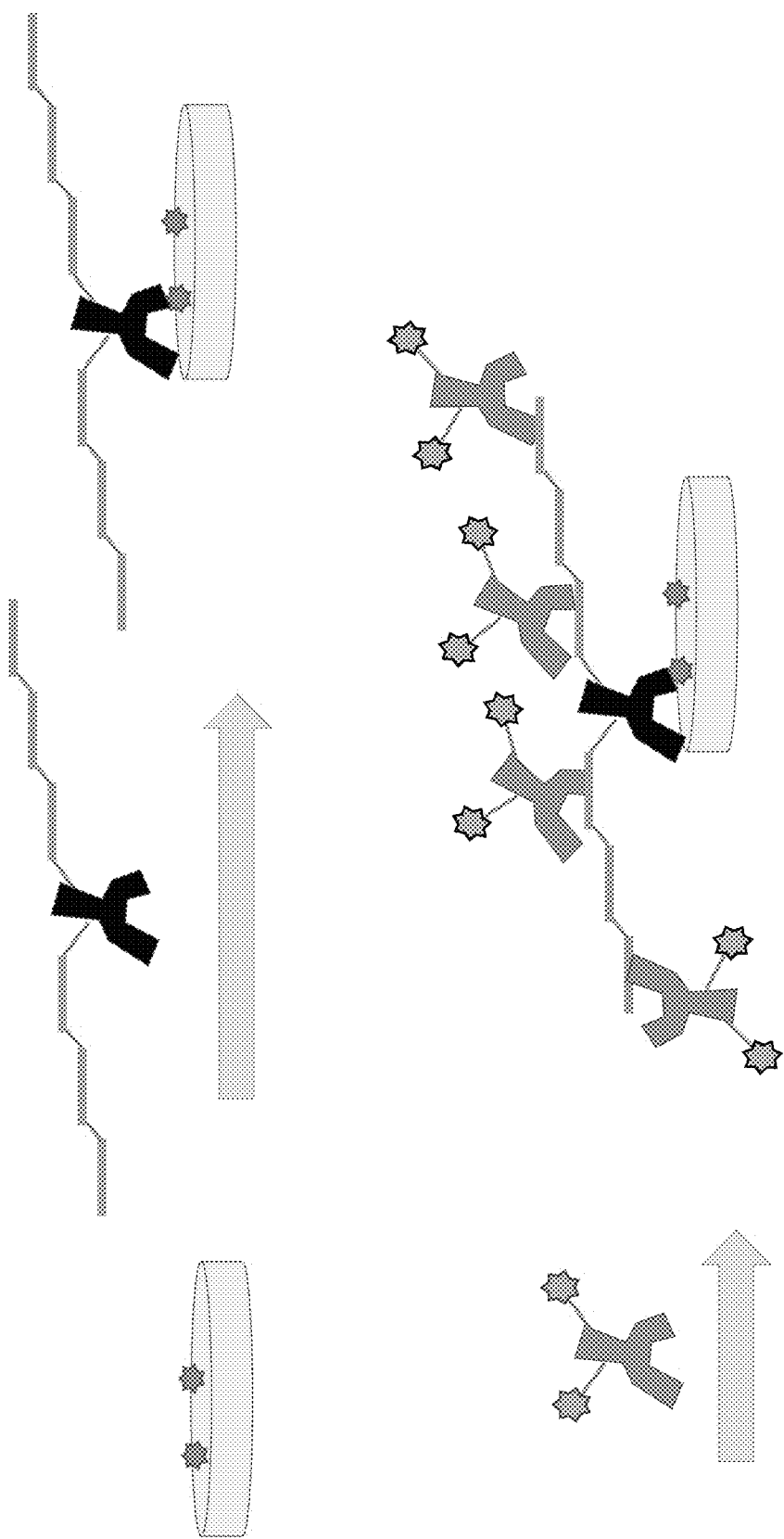
FIG. 25: Schematic representation of staining with primary antibodies comprising tandem repeat peptide bridging antigens to increase the number of antigenic determinants for reaction with a detectable anti-peptide secondary antibody.

As described herein, a linkable 3X tandem repeat peptide has been synthesized by solid-phase techniques and used to demonstrate improved detectability with anti-peptide antibodies. The tandem repeat peptide, with sequence AOA-(SGLQEQRNHLQ)$_3$-NH2 (PEP6'; SEQ ID NO:8) is a truncated version of the above-referenced PEP6 sequence. The AOA-3X-PEP6' peptide was conjugated to rabbit anti-PR and the staining intensity of this conjugate was compared to standard two-step staining with fluorescently-labeled secondary antibody. This protocol is schematically represented in FIG. 25, where the primary antibody shown is modified with two of the 3X tandem repeat peptides, thus providing binding sites for multiple detectable anti-peptide secondary antibodies.

Figure 26B:
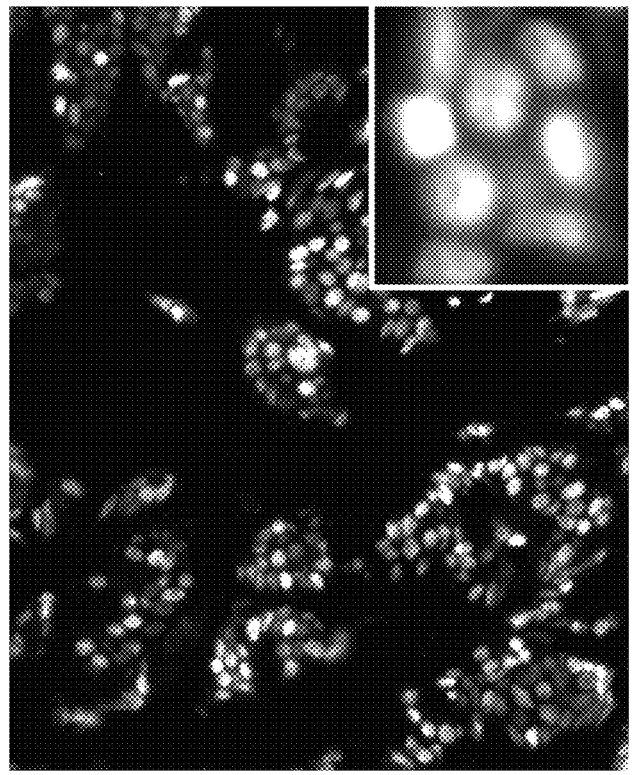
FIG. 26A-FIG. 26B: Staining of triple-positive breast cancer tissue with secondary antibodies (A) and with tandem repeat-conjugated primary antibodies (B). Here triple-positive breast cancer tissue (ILS30380) was stained with rabbit anti-HER2/Dy490-anti-rabbit-IgG (A) and tandem-repeat-3x-peptide (PEP6') conjugated-anti-HER2/Dy650-anti-PEP6.
Figure 26A:
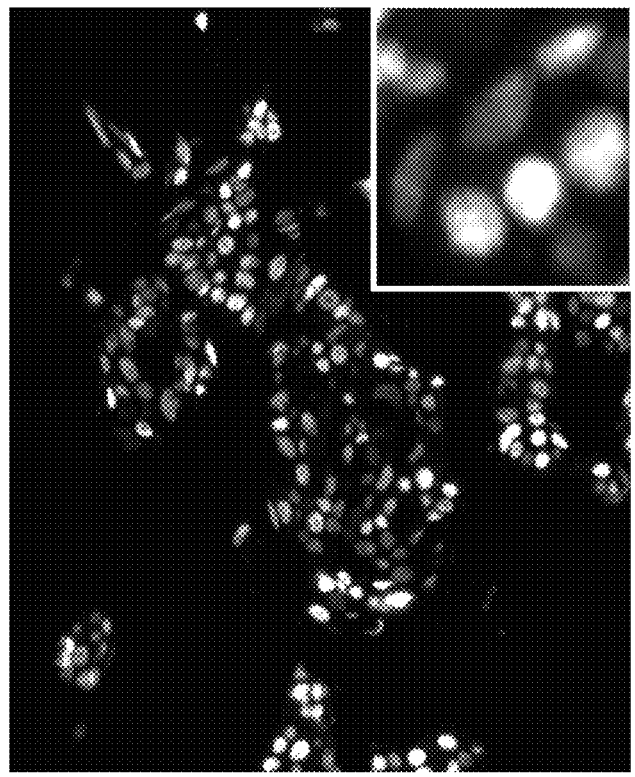

FIG. 26A illustrates the traditional staining of a triple-positive breast cancer tissue (ILS30380) using a rabbit anti-human PR primary antibody with a Dy650-labeled anti-rabbit secondary antibody. FIG. 26B illustrates the staining of the same tissue sample using a rabbit anti-human PR primary antibody coupled to the 3× tandem repeat PEP6' peptide with a Dy650-labeled anti-PEP6 secondary antibody. These results demonstrate that the staining intensity of the tandem repeat conjugate was 15% greater than the traditional fluorescently-labeled secondary antibody.

Bridging Antigens with Fluorescent Labels

The intensity of signal generation from fluorescently-labeled antibodies is dependent on the number of fluorophores at the binding site. The number of fluorophores on an antibody is, however, limited to roughly 4-6 fluorophores, as increasing the number of labels above that level may lead to the quenching of fluorescence by Forster energy resonance transfer (FRET). It is recognized that direct-labeled monoclonal antibodies produce very weak signals, as there is a limited number of fluorophores on the single fluorescently-labeled monoclonal antibody. It is also understood, however, that fluorescently-labeled secondary antibodies produce significantly stronger signals, as multiple (i.e., 2-4) secondary antibodies can bind to each primary antibody that is bound to the target.

Figure 27:
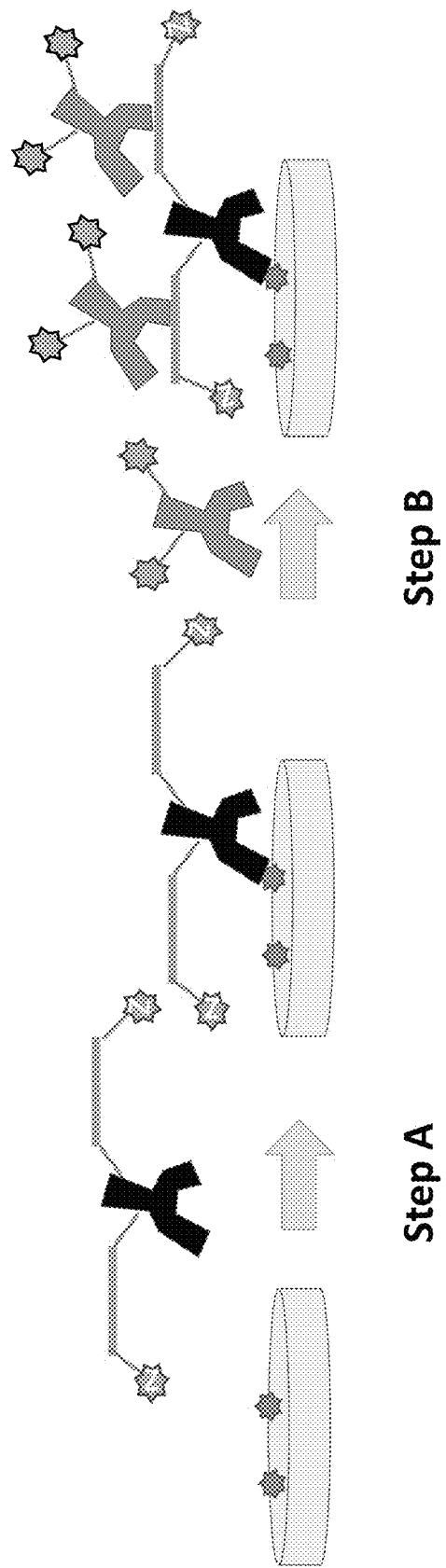
FIG. 27: Schematic representation of staining with immunoreagents comprising primary antibodies coupled to fluorophore-labeled bridging antigens.
Figure 28B:
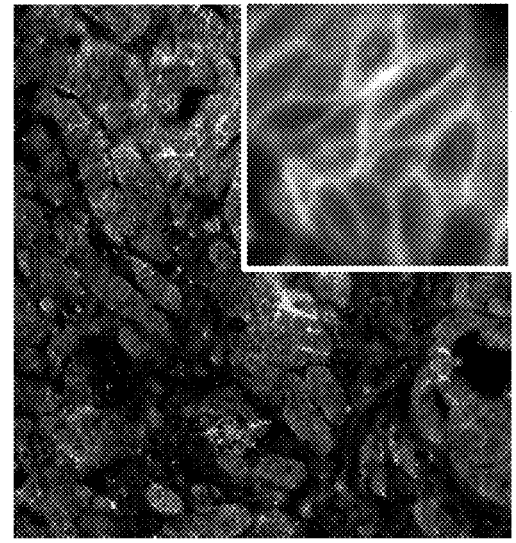
FIG. 28A-FIG. 28D: Staining results on triple-positive breast cancer tissue comparing rabbit anti-HER2/anti-rabbit-FITC to HER2-PEP7-FITC modified at three increasing levels of fluorescent labeling.
Figure 28D:
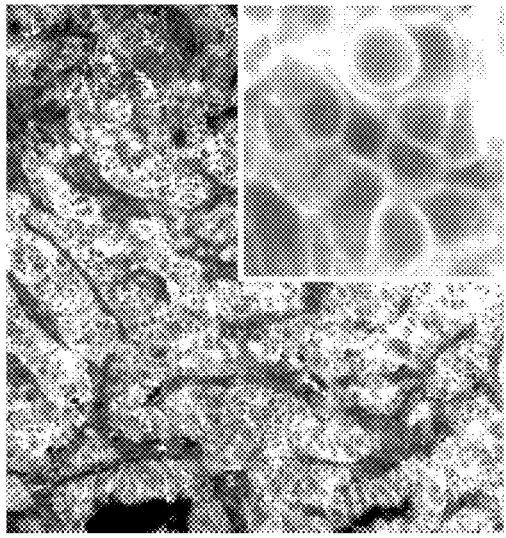
Figure 28A:
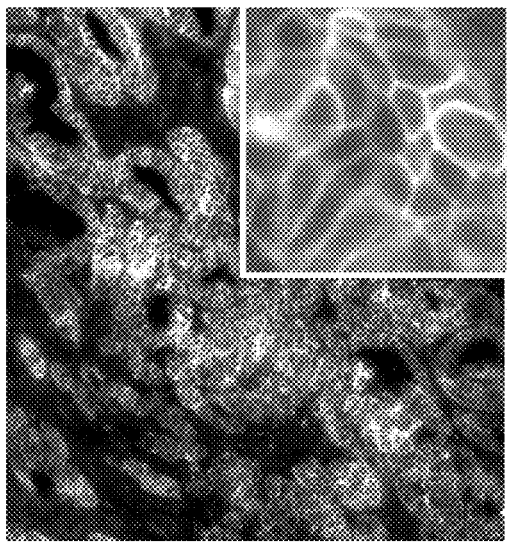
Figure 28C:
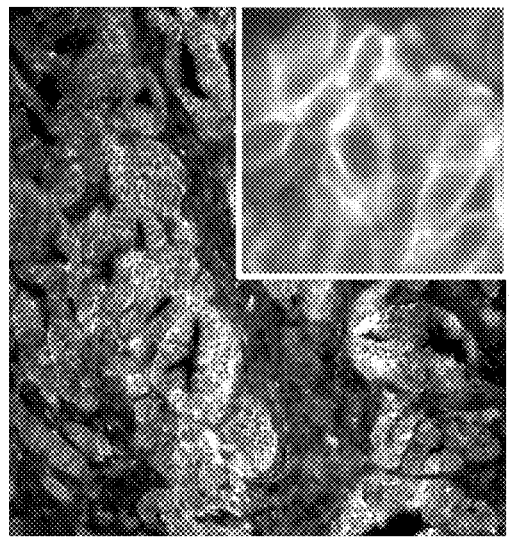

In an effort to increase the signal of the immunoreagents of the instant invention, for example as illustrated schematically in FIG. 27, a linkable bridging antigen comprising a fluorescent label conjugated to the distal end of a peptide bridging antigen was synthesized. The fluorophore-labeled bridging antigen was conjugated to a primary antibody, and the labeled antibody was incubated with the tissue containing an antigen targeted by the labeled primary antibody (FIG. 27, step A, where the fluorescent label is designated as "Z"). A fluorescently-labeled anti-peptide secondary antibody was next added to the sample (FIG. 27, step B), and the so-labeled sample was subsequently imaged.

Using triple-positive breast cancer tissue and an anti-HER2 antibody as the primary antibody, it was demonstrated that fluorescently-labeled primary antibodies, together with a fluorescently-labeled secondary antibody, provide a stronger signal than obtained in assays where the primary antibody does not contain a fluorophore (FIGS. 28A-28D).

Experimental

The linkable fluorescent peptide, AOA-ETSGLQEQRNHLQGK(FITC)-NH2 (PEP6-FITC), was synthesized by solid-phase peptide synthesis at Innopep (www.innopep.com). The peptide was linked to HER2 using the above procedure with the following inputs: HER2 @ 5 mg/mL, sulfo-S4FB (25 equiv.), peptide, 10, 20 and 30 equiv. Following conjugation, the number of peptides was determined by A490/A280 ratio following subtraction of the contribution of FITC to the A280. It was determined that 5, 6, and 7 peptides were incorporated on HER2, respectively. Tissues were stained using the procedure described above.

FIG. 28A-FIG. 28D show staining results on triple-positive breast cancer tissue (ILS25092) comparing rabbit anti-HER2/anti-rabbit-FITC to HER2-PEP6-FITC modified at three increasing levels, i.e. degree of labeling (DOL), 5×, 6×, and 7×, demonstrating that the highest level of PEP6-FITC modification of HER2 followed by FITC-anti-PEP6 gave a stronger signal than FITC-anti-rabbit secondary antibody. Quantitative results are presented in Table 12.

TABLE 12

| Sample | Average Pixel Intensity (API) |
|---|---|
| FITC-Secondary | 4175 |
| PEP6-FITC-5X | 3377 |
| PEP6-FITC-6X | 4053 |
| PEP6-FITC-7X | 4642 |

Heat Stripping of Immunoreagents

As an alternative to the selective stripping of immunoreagents using soluble bridging antigen peptides or cleavable conjugation moieties (see above), samples stained with immunoreagents of the invention have also been dissociated from tissue samples using a heat treatment. Specifically, following the initial four-plex staining and imaging with a cocktail of immunoreagents, CD3, CD4, CD8, and CD20, the slide was incubated in wash buffer overnight to remove coverslips without harming the tissue. Slides were then placed in citrate buffer, pH 6, and microwaved at 100% power (4×45 sec) to bring to a boiling point. Slides were microwaved for another 15 min at 20% power and then allowed to cool to room temperature for 20 min. Slides were washed in distilled water for 2 min and then in wash buffer for 2 min. Tissue was stained and imaged with immunoreagents HER2, ER, PR, and Ki-67.

Figure 29B:
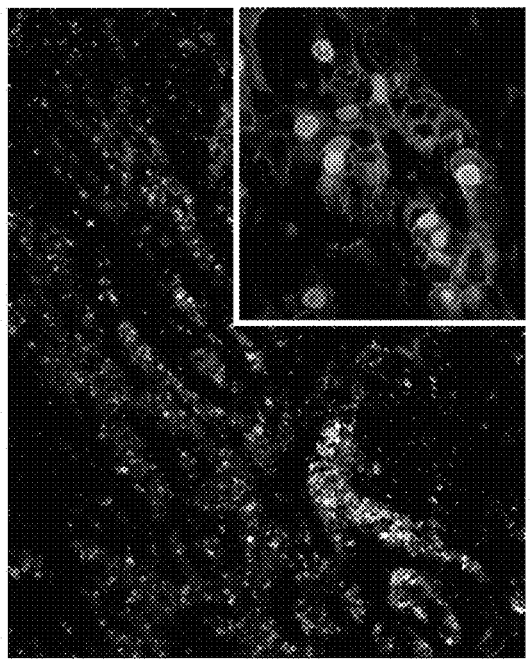
FIG. 29A-FIG. 29B: Serial staining of triple-positive breast cancer tissue with a heat step to strip the immunoreagent after the initial staining.
Figure 29A:
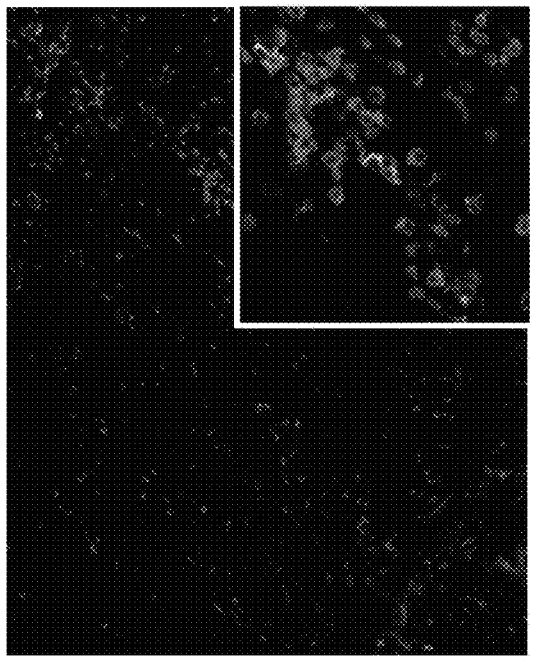

FIG. 29A and FIG. 29B show the results of the heat-stripping experiment, where the same tissue section is shown in each image. The tissue section was a triple-positive breast cancer tissue (ILS 32707), stained with a cocktail of immunoreagents specific for CD8, CD4, CD20, and CD3 (FIG. 29A). Following the stripping by microwave heating, the same tissue section was stained with a panet of immunoreagents to breast cancer markers HER2, ER, PR, and Ki-67 (FIG. 29B). Signals were normalized to the first round of antibody incubation for each slide.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. An immunoreagent composition comprising:
a primary antibody coupled to a bridging antigen, said bridging antigen comprising a peptide consisting of a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8; and
a detectable secondary antibody;
wherein the detectable secondary antibody is a rabbit monoclonal antibody specific for said peptide.

2. The immunoreagent composition of claim 1, wherein the bridging antigen comprises a plurality of copies of said peptide.

3. The immunoreagent composition of claim 2, wherein the plurality of copies of said peptides are arranged in a linear repeating structure.

4. The immunoreagent composition of claim 2, wherein the bridging antigen comprises a branched structure.

5. The immunoreagent composition of claim 1, wherein the primary antibody and the bridging antigen are coupled by a chemical coupling reaction through a conjugation moiety.

6. The immunoreagent of claim 5, wherein the primary antibody and the bridging antigen are coupled through a high-efficiency conjugation moiety that is at least 50% efficient in coupling the primary antibody and the bridging agent.

7. The immunoreagent composition of claim 6, wherein the high-efficiency conjugation moiety is a Schiff base.

8. The immunoreagent composition of claim 7, wherein the Schiff base is a hydrazone or an oxime.

9. The immunoreagent composition of claim 6, wherein the high-efficiency conjugation moiety is formed by a click reaction.

10. The immunoreagent composition of claim 5, wherein the conjugation moiety comprises a cleavable linker.

11. The immunoreagent composition of claim 1, wherein the primary antibody is specific for a cellular marker.

12. The immunoreagent composition of claim 11, wherein the cellular marker is selected from the group consisting of: 4-1BB, AFP, ALK1, Amyloid A, Amyloid P, Androgen Receptor, Annexin Al, ASMA, BCA225, BCL-1, BCL-2, BCL-6, BerEP4, Beta-Catenin, Beta-HCG, BG-8, BOB-1, CA19-9, CA125, Calcitonin, Caldesmon, Calponin-1, Calretinin, CAM 5.2, CD1a, CD2, CD3, CD4, CD5, CD7, CD8, CD10, CD15, CD19, CD20, CD21, CD22, CD23, CD25, CD30, CD31, CD33, CD34, CD38, CD42b, CD43, CD45 LCA, CD45RO, CD56, CD57, CD61, CD68, CD79a, CD99, CD117, CD138, CD163, CDX2, CEA, Chromogranin A, CMV, c-kit, c-MET, c-MYC, Collagen Type IV, Complement 3c (C3c), COX-2, CXCR5, CK1, CK5, CK6, CK7, CK8, CK14, CK18, CK17, CK19, CK20, CK903, CK AE1, CK AE1/AE3, D2-40, Desmin, DOG-1, E-Cadherin, EGFR, EMA, ER, ERCC1, Factor VIII-RA, Factor XIIIa, Fascin, FoxP1, FoxP3, Galectin-3, GATA-3, GCDFP-15, GCET1, GFAP, Glycophorin A, Glypican 3, Granzyme B, HBME-1, *Helicobacter Pylori*, Hemoglobin A, Hep Par 1, HER2, HMB-45, HSV I/II, ICOS, IFNgamma, IgA, IgD, IgG, IgM, IL17, IL4, Inhibin, iNOS, Kappa Ig Light Chain, Ki67, LAG-3, Lambda Ig Light Chain, Lysozyme, Mammaglobin A, MART-1/Melan A, Mast Cell Tryptase, MLH1, MOC-31, MPO, MSA, MSH2, MSH6, MUC1, MUC2, MUM1, MyoD1, Myogenin, Myoglobin, Napsin A, Nestin, NSE, Oct-2, OX40, OX40L, p16, p21, p27, p40, p53, p63, p504s, PAX-5, PAX-8, PD-1, PD-L1, PHH3, PIN-4, PLAP, PMS2, *Pneumocystis jiroveci* (*carinii*), PR, PSA, PSAP, RCC, S-100, SMA, SMM, Smoothelin, SOX10, SOX11, Surfactant Apoprotein A, Synaptophysin, TAG 72, TdT, Thrombomodulin, Thyroglobulin, TIA-1, TIM3, TRAcP, TTF-1, Tyrosinase, Uroplakin, VEGFR-2, Villin, Vimentin, and WT-1.

13. The immunoreagent composition of claim 1, wherein the primary antibody is specific for an immunoglobulin from a different species.

14. The immunoreagent composition of claim 1, wherein the detectable secondary antibody comprises a detectable label.

15. The immunoreagent composition of claim 14, wherein the detectable label is a fluorophore, an enzyme, an upconverting nanoparticle, a quantum dot, or a detectable hapten.

16. The immunoreagent composition of claim 15, wherein the detectable label is a fluorophore.

17. The immunoreagent composition of claim 15, wherein the enzyme is a peroxidase, an alkaline phosphatase, or a glucose oxidase.

18. The immunoreagent composition of claim 17, wherein the peroxidase is a horseradish peroxidase or a soybean peroxidase.

19. The immunoreagent composition of claim 1, wherein the bridging antigen comprises a detectable label.

20. The immunoreagent composition of claim 19, wherein the detectable label of the bridging antigen is a fluorophore.

21. The immunoreagent composition of claim 19, wherein the detectable secondary antibody comprises a detectable label.

22. The immunoreagent composition of claim 21, wherein the detectable label of the bridging antigen and the detectable label of the secondary antibody are both detectable by fluorescence at the same wavelength.

23. The immunoreagent composition of claim 1, wherein the detectable secondary antibody is specific for the bridging antigen with a dissociation constant of at most 1 nM.

24. The immunoreagent composition of claim 1, said secondary antibody having a dissociation constant of at most 10 nM.

25. A multiplexed immunoreagent composition comprising a plurality of the immunoreagent compositions of claim 1.

26. The multiplexed immunoreagent composition of claim 25, wherein the composition comprises at least three of the immunoreagent compositions.

27. The multiplexed immunoreagent composition of claim 25, wherein the composition comprises at least five of the immunoreagent compositions.

28. The multiplexed immunoreagent composition of claim 25, wherein the composition comprises eight of the immunoreagent compositions.

* * * * *

```
                        SEQUENCE LISTING

<160> NUMBER OF SEQ ID NOS: 8

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with aminooxyacetamide

<400> SEQUENCE: 1

Leu Ala Leu Gln Ala Gln Pro Val Pro Asp Glu Leu Val Thr Lys
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with aminooxyacetamide

<400> SEQUENCE: 2
```

```
Asp Ile Thr Ser Asp Thr Ser Gly Asp Phe Arg
1               5                   10

<210> SEQ ID NO 3
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with aminooxyacetamide

<400> SEQUENCE: 3

Asp Ala Thr Asn Val Gly Asp Glu Gly Gly Phe Ala Pro Asn Ile Leu
1               5                   10                  15

Glu Asn Lys

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with aminooxyacetamide

<400> SEQUENCE: 4

Gly Leu Glu Pro Gly Gln Glu Tyr Asn Val Leu Leu Thr Ala Glu Lys
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with aminooxyacetamide
<220> FEATURE:
<221> NAME/KEY: MOD_RES
<222> LOCATION: (8)..(8)
<223> OTHER INFORMATION: Phosporylated tyrosine

<400> SEQUENCE: 5

Arg Pro His Phe Pro Gln Phe Tyr Ser Ala Ser Gly Thr Ala
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with aminooxyacetamide

<400> SEQUENCE: 6

Glu Thr Ser Gly Leu Gln Glu Gln Arg Asn His Leu Gln Gly Lys
1               5                   10                  15

<210> SEQ ID NO 7
```

```
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with aminooxyacetamide

<400> SEQUENCE: 7

Gly Ala Pro Gly Lys Lys Arg Asp Met Ser Ser Asp Leu Glu Arg Asp
1               5                   10                  15

<210> SEQ ID NO 8
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminus modified with aminooxyacetamide
<220> FEATURE:
<221> NAME/KEY: MOD_RES
<222> LOCATION: (33)..(33)
<223> OTHER INFORMATION: AMIDATION

<400> SEQUENCE: 8

Ser Gly Leu Gln Glu Gln Arg Asn His Leu Gln Ser Gly Leu Gln Glu
1               5                   10                  15

Gln Arg Asn His Leu Gln Ser Gly Leu Gln Glu Gln Arg Asn His Leu
            20                  25                  30

Gln
```